US011299726B2

(12) United States Patent
Lai et al.

(10) Patent No.: US 11,299,726 B2
(45) Date of Patent: Apr. 12, 2022

(54) METHODS FOR DNA AND RNA EXTRACTION FROM FIXED PARAFFIN-EMBEDDED TISSUE SAMPLES

(71) Applicant: Cepheid, Sunnyvale, CA (US)

(72) Inventors: Edwin Wei-Lung Lai, Santa Clara, CA (US); Reuel Van Atta, Sunnyvale, CA (US); Kenneth E. Ho, Sunnyvale, CA (US)

(73) Assignee: CEPHEID, Sunnyvale, CA (US)

( * ) Notice: Subject to any disclaimer, the term of this patent is extended or adjusted under 35 U.S.C. 154(b) by 103 days.

(21) Appl. No.: 16/255,659

(22) Filed: Jan. 23, 2019

(65) Prior Publication Data

US 2019/0225959 A1     Jul. 25, 2019

Related U.S. Application Data

(62) Division of application No. 14/431,243, filed as application No. PCT/US2013/061863 on Sep. 26, 2013, now Pat. No. 10,233,440.

(60) Provisional application No. 61/846,037, filed on Jul. 14, 2013, provisional application No. 61/780,525, filed on Mar. 13, 2013, provisional application No. 61/707,654, filed on Sep. 28, 2012.

(51) Int. Cl.
| C12Q 1/68 | (2018.01) |
| C12N 15/10 | (2006.01) |
| G16B 25/00 | (2019.01) |
| G16B 25/10 | (2019.01) |
| C12Q 1/6806 | (2018.01) |
| C12Q 1/6886 | (2018.01) |
| G01N 1/06 | (2006.01) |

(52) U.S. Cl.
CPC ....... *C12N 15/1003* (2013.01); *C12Q 1/6806* (2013.01); *C12Q 1/6886* (2013.01); *G16B 25/00* (2019.02); *G16B 25/10* (2019.02); *C12Q 2600/118* (2013.01); *C12Q 2600/158* (2013.01); *C12Q 2600/16* (2013.01); *G01N 1/06* (2013.01)

(58) Field of Classification Search
None
See application file for complete search history.

(56) References Cited

U.S. PATENT DOCUMENTS

| 6,423,488 B1 | 7/2002 | Harvey |
| 6,469,159 B1 | 10/2002 | Belly et al. |
| 9,863,006 B2 | 1/2018 | Dobbelaer et al. |
| 10,233,440 B2 | 3/2019 | Lai et al. |
| 10,465,182 B2 | 11/2019 | Ho |
| 2002/0009794 A1 | 1/2002 | Danenberg et al. |
| 2005/0042656 A1 | 2/2005 | Davis et al. |
| 2006/0199197 A1 | 9/2006 | Danenberg et al. |
| 2008/0050746 A1 | 2/2008 | McMaster et al. |
| 2009/0047724 A1 | 2/2009 | Hillebrand |
| 2010/0063268 A1 | 3/2010 | Kanehara et al. |
| 2011/0065906 A1 | 3/2011 | Liu et al. |
| 2011/0244468 A1* | 10/2011 | Hollander .......... C12N 15/1003 435/6.12 |
| 2013/0171615 A1 | 7/2013 | Van Meerbergen et al. |
| 2013/0338350 A1 | 12/2013 | Hurt et al. |
| 2014/0087366 A1 | 3/2014 | Srinivasan et al. |
| 2014/0377854 A1* | 12/2014 | Zhou ..................... C12Q 1/6806 435/289.1 |
| 2015/0002523 A1 | 9/2015 | Lai et al. |
| 2016/0047821 A1 | 2/2016 | Baud et al. |
| 2017/0022493 A1 | 1/2017 | Ho |

FOREIGN PATENT DOCUMENTS

| CN | 101085799 A | 12/2007 |
| CN | 102725407 A | 10/2012 |
| CN | 102822339 A | 12/2012 |
| EP | 1870462 A1 | 12/2007 |
| EP | 2267127 A1 | 12/2010 |
| EP | 2793026 A1 | 10/2014 |
| EP | 2510123 B2 | 1/2019 |
| EP | 2718713 | 7/2019 |
| JP | 2008-529516 A | 8/2008 |
| JP | 2013-504330 A | 2/2013 |
| JP | 2013-530697 A | 8/2013 |
| JP | 2014-526255 A | 10/2014 |
| JP | 2015-518720 A | 7/2015 |
| JP | 2015-528313 A | 9/2015 |
| JP | 2016-520293 A | 7/2016 |
| WO | WO 2006/085104 A1 | 8/2006 |

(Continued)

OTHER PUBLICATIONS

Bohmann et al. (Clinical Chemistry, 2009, 55:9, p. 1719-1727) (Year: 2009).*
U.S. Office Action dated Sep. 20, 2017 issued in U.S. Appl. No. 14/431,243.
U.S. Final Office Action dated Apr. 6, 2018 issued in U.S. Appl. No. 14/431,243.
U.S. Office Action [Advisory Action] dated Aug. 10, 2018 issued U.S. Appl. No. 14/431,243.
U.S. Notice of Allowance dated Oct. 23, 2018 issued in U.S. Appl. No. 14/431,243.
U.S. Notice of Allowance [Supplemental] dated Dec. 3, 2018 in U.S. Appl. No. 14/431,243.
U.S. Office Action dated Dec. 28, 2017 issued in U.S. Appl. No. 15/208,525.

(Continued)

*Primary Examiner* — Stephanie K Mummert
(74) *Attorney, Agent, or Firm* — Emily M. Haliday; Weaver Austin Villeneuve & Sampson LLP

(57) ABSTRACT

Methods and reagents are provided for the rapid extraction of nucleic acids from a fixed paraffin embedded sample (e.g., a FFPET sample). In some embodiments, the methods comprise incubating one or more sections of said tissue sample in a lysis solution comprising a buffer sufficient to maintain the pH of said solution at a pH ranging from about pH 4 to about pH 9; a chaotropic agent; a chelating agent; and a detergent; where the incubating is at a temperature ranging from about 50° C. to about 100° C.; and recovering the nucleic acid from said lysis solution.

19 Claims, 8 Drawing Sheets

(56) References Cited

FOREIGN PATENT DOCUMENTS

| WO | WO 2008/035991 A2 | 3/2008 |
|---|---|---|
| WO | WO 2009/127350 A1 | 10/2009 |
| WO | WO 2010/123908 A1 | 10/2010 |
| WO | WO 2011/070507 A1 | 6/2011 |
| WO | WO 2011/083429 A1 | 7/2011 |
| WO | WO 2011/104027 A1 | 9/2011 |
| WO | WO 2011/124708 A1 | 10/2011 |
| WO | WO 2011/157683 A1 | 12/2011 |
| WO | WO 2012/168003 A1 | 12/2012 |
| WO | WO 2013/037401 A1 | 3/2013 |
| WO | WO 2013/175188 A1 | 11/2013 |
| WO | WO 2014/047141 A1 | 3/2014 |
| WO | WO 2014/052551 A1 | 4/2014 |
| WO | WO 2014/146780 A1 | 9/2014 |
| WO | WO 2016/205233 A2 | 12/2016 |
| WO | WO 2017/019293 A1 | 2/2017 |

OTHER PUBLICATIONS

U.S. Final Office Action dated Jun. 6, 2018 issued in U.S. Appl. No. 15/208,525.
U.S. Office Action dated Dec. 4, 2018 issued in U.S. Appl. No. 15/208,525.
PCT International Search Report and Written Opinion dated Dec. 26, 2013 issued in PCT/US2013/061863.
PCT International Preliminary Report on Patentability dated Mar. 31, 2015 issued in PCT/US2013/061863.
PCT International Search Report and Written Opinion dated Dec. 4, 2013 issued in PCT/US2013/061654.
PCT International Search Report and Written Opinion dated Sep. 27, 2016 issued in PCT/US2016/041917.
PCT International Preliminary Report on Patentability dated Feb. 8, 2018 issued in PCT/US2016/041917.
Australian Examination report No. 1 dated Jul. 10, 2018 issued in AU 2013323586.
EP Extended Search Report dated Apr. 11, 2016 issued in EP 13842384.3.
EP Office Action dated May 12, 2017 issued in EP 13842384.3.
EP Office Action dated Jun. 22, 2018 issued in EP 13842384.3.
EP Office Action dated Jan. 30, 2019 issued in EP 16742522.2.
Alvarez-Aldana, et al. (Feb. 2015) "Comparison of five protocols to extract DNA from paraffin-embedded tissues for the detection of human papillomavirus", *Pathology Research and Practice*, 211(2): 150-155.
Anonymous, (Apr. 22, 2015) "Solution FP7 Safety Data Sheet", *Mo Bio Laboratories Inc.*, 5 pages, XP055261385, Retrieved from the Internet: URL: https://mobio.com/media/wysiwyg/pdfs/sds/12250-7.pdf [retrieved on Mar. 30, 2016].
Anonymous, (Apr. 22, 2015) "Solution FP8 Safety Data Sheet", *Mo Bio Laboratories Inc.*, 5 pages, XP055261388, Retrieved from the Internet: URL: https://mobio.com/media/wysiwyg/pdfs/sds/12250-8.pdf [retrieved on Mar. 30, 2016].
Anonymous, (Apr. 27, 2015) "Solution FP1 Safety Data Sheet", *Mo Bio Laboratories Inc.*, 5 pages, XP055261376, Retrieved from the Internet: URL: https://mobio.com/media/wysiwyg/pdfs/sds/12250-1.pdf [retrieved Mar. 30, 2016].
Anonymous, (Apr. 28, 2009) "Bi0stic(TM) FFPE Tissue DNA Isolation Kit", *Mo Bio Laboratories Inc.*, 16 pages, XP055261373. Retrieved fron Internet: URL: http://www.biotechniques.com/multimedia/archive/00074/MO_BIO-FP-FFPE_74612a.pdf [retrieved Mar. 30, 2016].
Anonymous, (Apr. 3, 2015) "Solution FP5 Safety Data Sheet", *Mo Bio Laboratories Inc.*, 5 pages, XP055261382, Retrieved from the Internet: URL: https://mobio.com/media/wysiwyg/pdfs/sds/12250-5.pdf [retrieved Mar. 30, 2016].
Anonymous, (Apr. 9, 2015) "Solution FP4 Safety Data Sheet", *Mo Bio Laboratories Inc.*, 5 pages, XP055261380, Retrieved from the Internet: URL: https://mobio.com/media/wysiwyg/pdfs/sds/12250-4.pdf [retrieved Mar. 30, 2016].
Anonymous, (Apr. 9, 2015) "Solution FP6 Safety Data Sheet", *Mo Bio Laboratories Inc.*, 5 pages, XP055261384, Retrieved from the Internet: URL: https://mobio.com/media/wysiwyg/pdfs/sds/12250-6.pdf [retrieved Mar. 30, 2016].
Anonymous, (May 8, 2015) "Solution FP3 Safety Data Sheet", *Mo Bio Laboratories Inc.*, 5 pages, XP055261381, Retrieved from the Internet: URL: https://mobio.com/media/wysiwyg/pdfs/sds/12250-3.pdf [retrieved Mar. 30, 2016].
Anoymous, (Apr. 27, 2015) "Solution FP2 Safety Data Sheet", *Mo Bio Laboratories Inc.*, 5 pages, XP055261377, Retrieved from the Internet: URL: https://mobio.com/media/wysiwyg/pdfs/sds/12250-2.pdf [retrieved Mar. 30, 2016].
Bohmann, et al. (Sep. 2009) "RNA extraction from archival formalin-fixed paraffin-embedded tissue: A comparison of manual, semiautomated, and fully automated purification methods" *Clinical Chemistry*, 55(9): 1719-1727.
Butkus, (Sep. 27, 2012) "Cepheid Plans 1,000-Target PCR, Protein Detection, FFPE Analysis, Other Upgrades to GeneXpert", 6 pages, XP055261180. Retrieved from the Internet: URL: https://www.genomeweb.com/pcrsample-prepjcepheid-plans-1000-target-per-protein-detection-ffpe-analysis-other-upgrades-gen [retrieved Mar. 29, 2016].
Dedhia, et al. (2007) "Evaluation of DNA extraction methods and real time PCR optimization formalin-fixed paraffin-embedded tissues" *Asian Pacific Journal of Cancer Prevention*, 8(1): 55-59.
Gilbert, et al. (Jun. 2007) "The Isolation of Nucleic Acids from Fixed, Paraffin-Embedded Tissues—Which Methods Are Useful When?" *PLOS one*, 2(6): e537 (12 pages).
Gouveia, et al. (Jan. 2014) "Comparison of Two Methods of RNA Extraction from Formalin-Fixed Paraffin-Embedded Tissue Specimens", *BioMed Research International*, 47(5): 541-5.
Hennig, et al. (Oct. 14, 2010) "Automated Extraction of DNA and RNA from a Single Formalin-Fixed Paraffin-Embedded Tissue Section for Analysis of Both Single-Nucleotide Polymorphisms and mRNA Expression." *Clinical Chemistry*, 56(12): 1845-1853.
Kennedy, Suzanne (Nov. 2009) "Isolation of DNA from FFPE samples without paraffin removal", *BioTechniques*, 3 pages; XP055261394, retrieved from the Internet: URL: http://www.biotechniques.com/protocols/DNA_RNA_Isolation_and_Purificat/From_FFPE_Archival_Tissues/lsolation-of-DNA-from-FFPE-samples-without-paraffin-removal/biotechniques-181192.html [retrieved Mar. 30, 2016].
Oberli, et al. (Apr. 19, 2008) "Expression profiling with RNA from formalin-fixed, paraffin-embedded material" *BMC Medical Genomics*, 1(1): 9 (15 pages).
Park, et al. (Nov. 1996 ) "Detection of Hepatitis C Virus RNA using Ligation-Dependent Polymerase Chain Reaction in Formalin-Fixed, Paraffin-Embedded Liver Tissues", *American Journal Of Pathology*, 149(5): 1485-1491.
Shi, et al. (2004) "DNA extraction from archival formalin-fixed, paraffin-embedded tissues: heat-induced retrieval in alkaline solution", *Histochem Cell Biol*, 122:211-218.
Tang, et al. (2009) "DNA Extraction from Formalin-Fixed, Paraffin-Embedded Tissue" *Cold Spring Harb Protoc*, 4(2) (5 pages) doi: 10.1101/pdb.prot5138.
Thermo Fisher Scientific—AU (Nov. 19, 2011) "RNA Stabilization and Storage—RNAlater®", Thermo Fisher Scientific—AU [Retrieved from internet on Sep. 29, 2011] Viewed on internet. <URL: https://www.thermofisher.com/au/en/home/brands/product-brand/malater.html> published on Nov. 19, 2011 as per Wayback Machine. 4 pages.
Qiagen (Feb. 8, 2008) "FAQ—What is the recommended solution in which to store RNA samples that will be used as templates for cDNA synthesis?" (FAQ ID-2659) [Retrieved from internet on Sep. 29, 2011] Viewed on internet. <URL: https://www.qiagen.com/au/resources/faq?id=7402936b-e4d7-417c-a338-5dd555e26f82&lang=en >. Published on Feb. 8, 2008 as per Wayback Machine.
Stratagene (1988) Catalog "Gene Characterization Kits" p. 39.
Weiss, et al. (2011) "Efficient and Cost-Effective Extraction of Genomic DNA From Formalin-Fixed and Paraffin-Embedded tissues" *Veterinary Pathology Online*, 4(4) :834-838.
U.S. Notice of Allowance dated Jun. 20, 2019 issued in U.S. Appl. No. 15/208,525.

(56) References Cited

OTHER PUBLICATIONS

Canadian Office Action dated Sep. 21, 2020 issued in CA 2,886,389.
EP Office Action dated Jul. 30, 2019 issued in EP 13842384.3.
EP Extended Search Report dated Jul. 23, 2020 issued in EP 20157569.3.
JP Office Action dated Jul. 27, 2020 issued in JP 2018-503555.
Grepin et al. (Nov. 20, 2012) "Measurement of Hemoglobin" Bio-protocol, 2(22): e291 [2 pages], [online], URL: https://bio-protocol.org/e291 (publication showing well-known technology).
Kume, Kazuhiko, The University of Tokyo, Faculty of Medicine, Department of Biochemistry and Molecular Biology (Division of Cellular Information) Lab Manual, [online], Oct. 28, 2014, URL: https://web.archive.org/web/20141028104050/http://square.umin.ac.jp/biochem2/contents/Manuals/manual18.html [2 pages].
Sigma-Aldrich "Antifoam Y-30 Emulsion", [online], [searched on Jul. 17, 2020], URL: https://www.sigmaaldrich.com/catalog/product/sigma/a5758?lang=en&region=CA&cm_sp=Insite-_-hpRecs_personalizedRecs_recommendedFyCtr-_-personalizedRecs5-1 [4 pages].
Australian Examination report No. 1 dated Mar. 25, 2021 issued in AU 2019204059.
Chinese Office Action dated Jan. 22, 2021 issued in CN 201680055819.5.
Chirgwin, John M., et al. (1979) "Isolation of biologically active ribonucleic acid from sources enriched in ribonuclease." *Biochemistry* 18(24): 5294-5299.
Willis, Melissa Swope, et al. (2005) "Investigation of protein refolding using a fractional factorial screen: a study of reagent effects and interactions." *Protein science* 14(7): 1818-1826.
EP Extended Search Report dated May 6, 2021 issued in EP 20204053.1.
AU Office Action dated Sep. 27, 2021 issued in AU 2016298048.
Chinese 2nd Office Action dated Aug. 18, 2021 issued in CN 201680055819.5.
JP 2nd Office Action dated Jul. 5, 2021 issued in JP 2018-503555.
Banerjee et al. (1995) "Microwave-based DNA extraction from paraffin-embedded tissue for PCR Amplification" Biotechniques 18(5): pp. 768, 770, 772/773.

\* cited by examiner

METHODS FOR DNA AND RNA EXTRACTION FROM FIXED PARAFFIN-EMBEDDED TISSUE SAMPLES

CROSS-REFERENCE TO RELATED APPLICATIONS

This application is a divisional of U.S. Ser. No. 14/431,243, filed on Mar. 25, 2015, which is a U.S. 371 National Phase of PCT/US2013/061863, filed on Sep. 26, 2013, which claims benefit of and priority to U.S. Ser. No. 61/846,037, filed on Jul. 14, 2013, to U.S. Ser. No. 61/780,525, filed on Mar. 13, 2013, and to U.S. Ser. No. 61/707,654, filed on Sep. 28, 2012, all of which are incorporated herein by reference in their entirety for all purposes.

STATEMENT OF GOVERNMENTAL SUPPORT

[Not Applicable]

BACKGROUND

The use of gene expression profiling is not only prevalent in various research applications, but is rapidly becoming part of many therapeutic regimes. For example, the determination of gene expression levels in tissues is of great importance for accurately diagnosing human disease and is increasingly used to determine a patient's course of treatment. Pharmacogenomic methods can identify patients likely to respond to a particular drug and can lead the way to new therapeutic approaches For example, thymidylate synthase (TS) is an integral enzyme in DNA biosynthesis where it catalyzes the reductive methylation of deoxyuridine monophosphate (dUMP) to deoxythymidine monophosphate (dTMP) and provides a route for de novo synthesis of pyrimidine nucleotides within the cell (Johnston et al. (1995) *Cancer Res.*, 55: 1407-1412). Thymidylate synthase is a target for chemotherapeutic drugs, most commonly the antifolate agent 5-fluorouracil (5-FU). As an effective agent for the treatment of colon, head and neck and breast cancers, it is believed the primary action of 5-FU is to inhibit TS activity, resulting in depletion of intracellular thymine levels and subsequently leading to cell death.

Thymidylate synthase is also known to have clinical importance in the development of tumor resistance, as demonstrated by studies that have shown acute induction of TS protein and an increase in TS enzyme levels in neoplastic cells after exposure to 5-FU (Spears et al. (1982) *Cancer Res.* 42: 450-456; Swain et al. (1989) *J. Clin. Oncol.* 7: 890-899). The ability of a tumor to acutely overexpress TS in response to cytotoxic agents such as 5-FU may play a role in the development of fluorouracil resistance. the levels of TS protein appear to directly correlate with the effectiveness of 5-FU therapy, that there is a direct correlation between protein and RNA expression and TS expression is a powerful prognostic marker in colorectal and breast cancer (Jackman et al. (1985) *Experimental and Clinical Progress in Cancer Chemotherapy*, F. M. Muggia ed., Martinus et al. (1992) *Cancer Res.*, 52: 108-116). In advanced metastatic disease, both high TS mRNA, quantified by RT-PCR, and high TS protein expression, have been shown to predict a poor response to fluoropyrimidine-based therapy for colorectal (Johnston et al. (1995) supra.; Farrugia et al. (1997) *Proc. Annu. Meet Am. Assoc. Cancer Res.* 38: A4132; Leichman et al. (1997) *J. Clin. Oncol.* 15(10): 3223-3229), gastric (Lenz et al. (1998) *Clin. Cancer Res.*, 4(5): 1227-1234), and head and neck (Johnston et al. (1995) *Cancer Res.*, 55: 1407-1412; Leichman et al. (1997) *J. Clin. Oncol.* 15(10): 3223-3229) cancers.

Similarly, mutation of the KRAS oncogene is predictive of a very poor response to panitumumab (VECTIBIX®) and cetuximab (ERBITUX®) therapy in colorectal cancer (Lièvre et al. (2006) *Cancer Res.*, 66(8): 3992-3995). Currently, one of the most reliable ways to predict whether a colorectal cancer patient will respond to one of the EGFR-inhibiting drugs is to test for certain "activating" mutations in the gene that encodes KRAS, which occur in 40% of colorectal cancers. Studies show patients whose tumors express the mutated version of the KRAS gene will not respond to cetuximab or panitumumab.

One important source for this type of information comes in the form of formalin-fixed, paraffin-embedded tissue ("FFPET") samples, that are routinely created from biopsy specimens taken from patients undergoing a variety of diagnostic and/or therapeutic regimens for a variety of different diseases. These samples are usually associated with the corresponding clinical records and often play an important role in diagnosis and determination of treatment modality. For example, tumor biopsy FFPET samples are often linked with cancer stage classification, patient survival, and treatment regime, thereby providing a potential wealth of information that can be cross-referenced and correlated with gene expression patterns. However, the poor quality and quantity of nucleic acids isolated from FFPET samples has led to their underutilization in gene expression profiling studies.

It is known that RNA can be purified and analyzed from FFPET samples (Rupp and Locker (1988) *Biotechniques* 6: 56-60), however, RNA isolated from FFPET samples is often moderately to highly degraded and fragmented. In addition to being degraded and fragmented, chemical modification of RNA by formalin restricts the binding of oligo-dT primers to the polyadenylic acid tail and can impede the efficiency of reverse transcription.

In view of these difficulties, the analysis of nucleic acids from formalin fixed, paraffin embedded tissue (FFPET) has proven challenging due to the multiple steps required for generating PCR-amplifiable genetic material. The procedure to isolate nucleic acids from FFPET may include; removal of paraffin (deparaffinization), lysis of preserved sample (protease digestion), reversal of cross-links acquired during the fixation process and solid phase-based purification of nucleic acids. These protocols are typically complex and labor intensive.

SUMMARY

Methods and regents for the isolation of nucleic acids from fixed embedded tissue samples (e.g., FFPET samples) are provided. In some embodiments, the methods are simple, easily semi-automated or fully automated and typically require minimal hands-on time, while extracting nucleic acids of high yield and PCR-amplifiable quality.

Accordingly, in some embodiments, methods for extracting a nucleic acid from a fixed paraffin-embedded biological tissue sample are provided where the method comprises incubating one or more sections of the tissue sample in a lysis solution comprising: a buffer sufficient to maintain the pH of the solution at a pH ranging from about pH 3 to about pH 9; a chaotropic agent; an antioxidant and/or chelating agent; and a detergent; where the incubating is at a temperature ranging from about 50° C. to about 100° C. or from about 50° C. to about 110° C.; and recovering the nucleic acid from the lysis solution. In some embodiments, the tissue sample comprises a formalin fixed paraffin embedded sample. In some embodiments the nucleic acid is a deoxyribonucleic acid (DNA). In some embodiments the nucleic acid is a ribonucleic acid (RNA) (e.g., an mRNA, a non-coding RNA (e.g., microsatellite RNA), and the like). In some embodiments the buffer comprises a buffer selected from the group consisting of Tris, phosphate buffer, PBS, citrate buffer, TAPS, Bicine, Tricine, TAPSO, HEPES, TES, MOPS, PIPES, Cacodylate, SSC, and MES. In some embodiments the buffer comprises a TRIS buffer. In some embodiments the buffer comprises a citrate buffer. In some embodiments the pH of the lysis solution ranges from about pH 3 to about pH 8.5, or about pH 6 to about pH 8, or about pH 3 to about pH 6. In some embodiments the pH of the lysis solution is about pH 7. In some embodiments the pH of the lysis solution is about pH 3 or about pH 3.6. In some embodiments the chaotropic agent comprises an agent selected from the group consisting of a guanidinium compound, formamide, lithium perchlorate, magnesium chloride, urea, and thiourea. In some embodiments chaotropic agent comprises a guanidinium compound selected from the group consisting of guanidinium hydrochloride, and guanidinium isothiocyanate. In some embodiments the concentration of the chaotropic agent in the solution ranges from about 1 M to about 10 M, or from about 2 M to about 9 M, or from about 3 M to about 8 M, or from about 4 M to about 7 M. In some embodiments, the chaotrope is present at about 4M, or about 7 M in the lysis solution. In some embodiments the antioxidant and/or chelating agent comprises an agent selected from the group consisting of N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N, N',N'-tetraacetic acid (BAPTA), and a phosphonate chelating agent. In some embodiments the antioxidant and/or chelating agent comprises N-acetyl-L-cysteine. In some embodiments the antioxidant and/or chelating agent comprises ethylenediaminetetraacetic acid (EDTA). In certain embodiments the antioxidant and/or chelating agent comprise 0.5% to about 5% of said solution or about 0.5% to about 3% of said solution, or about 0.5% to about 2% of said solution or about 1% of said solution. In some embodiments the concentration of the antioxidant and/or chelating agent in the solution ranges from about 10 mM to about 100 mM. In some embodiments the antioxidant and/or chelating agent in the solution is about 50 mM. In some embodiments, the detergent is an ionic detergent or a non-ionic detergent. In some embodiments, the detergent comprises a detergent selected from the group consisting of N-lauroylsarcosine, sodium dodecyl sulfate (SDS), cetyl methyl ammonium bromide (CTAB), TRITON®-X-100, n-octyl-β-D-glucopyranoside, CHAPS, n-octanoylsucrose, n-octyl-β-D-maltopyranoside, n-octyl-β-D-thioglucopyranoside, PLURONIC® F-127, TWEEN® 20, and n-heptyl-β-D-glucopyranoside. In certain embodiments the detergent comprises N-lauroylsarcosine. In certain embodiments, the detergent comprises SDS. In certain embodiments, the concentration of the detergent in the solution ranges from about 10 mM up, or from about 20 mM, or from about 30 mM, to about 100 mM, or up to about 80 mM, or up to about 60 mM, or up to about 50 mM. In some embodiments, the concentration of the detergent in the solution ranges from about 30 mM up to about 40 mM. In some embodiments, the detergent comprises about 0.1% to about 2% of the lysis solution. In some embodiments, the detergent comprises about 0.1% to about 1% of the lysis solution. In some embodiments, the detergent comprises about 0.2% to about 0.8% of the lysis solution. In some embodiments, the detergent comprises about 0.4% the lysis solution. In some embodiments, the solution further comprises a second detergent (e.g., TWEEN 20). In some embodiments, the second detergent comprises about 0.5% to about 30% (v/v) of the lysis solution. In some embodiments, the lysis solution comprises a second chaotrope and/or reducing agent. In some embodiments, the second chaotrope comprise urea. In some embodiments the concentration of the second chaotropic agent in the solution ranges from about 1 M to about 10 M, or from about 2 M to about 9 M, or from about 3 M to about 8 M, or from about 4 M to about 7 M. In some embodiments, the second chaotrope is present at about 4M, or about 7 M in the lysis solution. In some embodiments, the lysis solution further comprises calcium chloride. In some embodiments, the concentration of the calcium chloride ranges from about 5 mM to about 30 mM. In some embodiments the lysis solution comprises tris buffer; EDTA; guanidine hydrochloride; SDS; Tween 20; urea; and calcium chloride. In some embodiments the Tris buffer is at about pH 7 and is present at a concentration of about 50 mM; the EDTA is present at a concentration of about 50 mM; the guanidine hydrochloride is present at a concentration of about 4 M; the SDS is present at a concentration of about 34.7 mM; the urea is present at a concentration of about 6 M; the Tween is present at about 10% (v/v); and the calcium chloride is present at a concentration of about 10 mM. In certain embodiments the lysis solution comprises guanidine thiocyanate, N-acetyl-L-cysteine, sodium citrate, N-Lauroylsarcosine; and the pH of said solution ranges from about pH 3.0 to about pH 5.5. In certain embodiments the pH of the solution is about pH 3.5. In certain embodiments the lysis solution comprises guanidine thiocyanate at about 4.5M, about 1% N-acetyl-L-cysteine, about 25 mM sodium citrate, and about 0.40% N-Lauroylsarcosine. In certain embodiments the solution further comprises Trizma base. In certain embodiments the pH of the solution is about pH 5.09. In certain embodiments the solution comprises guanidine thiocyanate at about 4.5M, about 1% N-acetyl-L-cysteine, about 25 mM sodium citrate; and about 50 mM Trizma base.

In some embodiments, the incubating is for a time period that ranges from about 15 minutes up to 24 hours. In some embodiments, the incubating is for a time period ranging from about 15 minutes, or from about 20 minutes, or from about 30 minutes up to about 24 hours, or up to about 18 hours, or up to about 12 hours, or up to about 8 hours, or up to about 6 hours, or up to about 3 hours, or up to about 90 minutes, or up to about 60 minutes, or up to about 30 minutes. In some embodiments, the time period ranges from about 30 minutes to about 60 minutes.

In some embodiments the incubating is at a temperature ranging from about 70° C. to about 95° C. In some embodiments the incubating is at a temperature ranging up to about 80° C. In some embodiments the incubation is for about 60 minutes at about 80° C. to provide an RNA extraction. In some embodiments the incubation is for about 30 minutes at about 90° C. to provide a DNA extraction.

In certain embodiments the recovering comprises the addition of an alcohol (e.g., a lower alcohol) to the solution. In some embodiments, the lower alcohol comprises a C1-C8, or a C1-C6 alcohol. In some embodiments, the lower alcohol comprises ethanol or isopropanol.

In some embodiments, the one or more sections range in thickness from about 1 µm to about 15 µm. In some embodiments, the one or more sections range in thickness from about 1 µm, or from about 2 µm, or from about 3 µm or from about 4 µm up to about 25 µm, or up to about 20 µm, or up to about 15 µm, or up to about 10 µm. In some embodiments, the one or more sections are about 5 µm or about 10 µm in thickness. In some embodiments, the one or more sections comprise a plurality of sections having a thickness of about 8 µm or less or a thickness or about 5 µm or less. In some embodiments, the one or more sections comprise sections from a tissue sample from a cancerous tissue. In some embodiments, the tissue sample comprises a sample from a cancer selected from the group consisting of ovarian cancer, pancreatic cancer, lung cancer, hepatocarcinoma, melanoma, retinoblastoma, breast cancer, colorectal cancer, testicular cancer, leukemia, lymphoma, brain tumor, cervical carcinoma, sarcoma, prostate tumor, bladder tumor, tumor of reticuloendothelial tissue, Wilm's tumor, astrocytoma, glioblastoma, neuroblastoma, ovarian carcinoma, osteosarcoma, renal cancer, and head and neck cancer. In some embodiments, the lysis solution further comprises a protease (e.g., proteinase K, trypsin, chymotrypsin, papain, and the like). In some embodiments, the method does not utilize a protease. In some embodiments, the method does not include further steps of deparaffinization and/or additional reagents for deparaffinization. In some embodiments, the method does not utilize an organic solvent for deparaffinization. In some embodiments, the incubating is not in the presence of an organic solvent. In some embodiments, the method further comprises amplifying all or a portion of the nucleic acid. In some embodiments, the method further comprising utilizing the nucleic acid as a template in a PCR amplification (e.g., RT-PCR, and the like). In some embodiments, the method further comprises amplifying the nucleic acid in a GeneXpert system. In some embodiments, the nucleic acid is used to determine the presence and/or expression level of expression of at least one target RNA that is an mRNA (e.g., KRT20, IGF2, ANXA10, CRH, ABL, ERBB1, ERBB2, ERBB3, ERBB4, ESR1, PGR, MPO, CDKN2A, MKI67, TOP2A, MCM5, BIRC5, MMP9, and MCM2 PTEN, APC, KRAS, GATA3, PIC3CA, MAP3K1, TP53, mutations of any of these, and the like).

In certain embodiments the nucleic acids are amplified from the original lysed samples two or more different times (e.g., over a period of at least 6 hours, or over a period of at least one day, or over a period of at least two days, or over a period of at least 4 days, or over a period of at least one week, or over a period of at least two weeks, or over a period of at least 4 weeks, or over a period of at least one month, or over a period of at least two months, or over a period of at least three months, or over a period of at least 6 months, or over a period of at least one year, or over a period of at least two years, or over a period of at least 5 years. In certain embodiments the second or later amplification comprises a repeat test. In certain embodiments the or later amplification comprise a reflex cartridge test.

In some embodiments, methods for quantitative measurement of gene expression of a target gene in a fixed paraffin embedded tissue sample are provided where the methods comprise: extracting an RNA from a formalin-fixed paraffin-embedded biological tissue sample according to any of the extraction methods described herein, subjecting the extracted nucleic acid to amplification using a pair of oligonucleotide primers capable of amplifying a region of a target gene mRNA, to obtain an amplified sample; and determining the presence and/or quantity of the target gene mRNA. In some embodiments, the quantity of the target gene mRNA is determined relative to the quantity of an internal control gene's (e.g., β-actin) mRNA from the isolated mRNA. In some embodiments, determining the relative gene expression level comprises using RT-PCR. In some embodiments, the target gene is selected from the group consisting of an ALK gene rearrangement, alpha-fetoprotein (AFP), Beta-2-microglobulin (B2M), beta-human chorionic gonadotropin (beta-hCG), BCR-ABL fusion gene, BRAF mutation V600E, CA15-3/CA27.29, CA19-9, CA-125, calcitonin, carcinoembryonic antigen (CEA), CD20, chromogranin A (CgA), chromosome 3, chromosome 7, chromosome 17, chromosome 9p21, chromosome 20q13, cytokeratin fragments 21-1, EGFR mutation analysis, estrogen receptor (ER), progesterone receptor (PR), fibrin/fibrinogen, HE4, HER4, HER2/neu, KIT, KRAS mutation analysis, lactate dehydrogenase, nuclear matrix protein 22, prostate-specific antigen (PSA), thyroglobulin, urokinase plasminogen activator (uPA), and plasminogen activator inhibitor (PAI-1).

In various aspects, the invention(s) contemplated herein may include, but need not be limited to, any one or more of the following embodiments:

Embodiment 1

A method for extracting a nucleic acid from a fixed paraffin-embedded biological tissue sample comprising: incubating one or more sections of the tissue sample in a lysis solution comprising: a buffer sufficient to maintain the pH of the solution at a pH ranging from about pH 3 to about pH 9; a chaotropic agent; an antioxidant and/or chelating agent; and a detergent; where the incubating is at a temperature ranging from about 50° C. to about 100° C.; and recovering the nucleic acid from the lysis solution.

Embodiment 2

The method of embodiment 1, where the tissue sample is a formalin fixed paraffin embedded sample.

Embodiment 3

The according to any one of embodiments 1-2, where the nucleic acid is a deoxyribonucleic acid (DNA).

Embodiment 4

The method of embodiment 1-2, where the nucleic acid is a ribonucleic acid (RNA).

Embodiment 5

The method of embodiment 4, where the RNA is an mRNA.

Embodiment 6

The method of embodiment 4, where the RNA is a non-coding RNA.

Embodiment 7

The method according to any one embodiments 1-6, where the buffer includes a buffer selected from the group consisting of Tris, phosphate buffer, PBS, citrate buffer, TAPS, Bicine, Tricine, TAPSO, HEPES, TES, MOPS, PIPES, Cacodylate, SSC, and MES.

Embodiment 8

The method of embodiment 7, where the buffer includes a citrate buffer.

Embodiment 9

The method of embodiment 7, where the buffer includes a TRIS buffer.

Embodiment 10

The method according to any one of embodiments 1-9, where the pH of the solution ranges from about pH 6 to about pH 8.

Embodiment 11

The method according to any one of embodiments 1-9, where the pH of the solution ranges from about pH 3 to about pH 6.

Embodiment 12

The method of embodiment 11, where the pH of the solution is about pH 7.

Embodiment 13

The method of embodiment 11, where the pH of the solution is about pH 3.5.

Embodiment 14

The method according to any one of embodiments 1-13, where the chaotropic agent includes an agent selected from the group consisting of a guanidinium compound, formamide, lithium perchlorate, magnesium chloride, urea, and thiourea.

Embodiment 15

The method of embodiment 14, where the chaotropic agent includes a guanidinium compound.

Embodiment 16

The method of embodiment 15, where the chaotropic agent includes a guanidinium compound selected from the group consisting of guanidinium hydrochloride, and guanidinium isothiocyanate.

Embodiment 17

The method according to any one of embodiments 1-16, where the concentration of the chaotropic agent in the solution ranges from about 1 M to about 10 M.

Embodiment 18

The method according to any one of embodiments 1-16, where the concentration of the chaotropic agent in the solution ranges from about 2 M to about 7 M.

Embodiment 19

The method according to any one of embodiments 1-18, where the antioxidant and/or chelating agent includes an agent selected from the group consisting of N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N,N',N'-tetraacetic acid (BAPTA), and a phosphonate chelating agent.

Embodiment 20

The method of embodiment 19, where the antioxidant and/or chelating agent includes N-acetyl-L-cysteine.

Embodiment 21

The method of embodiment 19, where the antioxidant and/or chelating agent includes EDTA.

Embodiment 22

The method according to any one of embodiments 1-21, where the concentration of the antioxidant and/or chelating agent in the solution ranges from about 10 mM to about 100 mM.

Embodiment 23

The method according to any one of embodiments 1-21, where the antioxidant and/or chelating agent includes about 0.5% to about 5% of the solution.

Embodiment 24

The method of embodiment 23, where the antioxidant and/or chelating agent includes about 0.5% to about 3% of the solution.

Embodiment 25

The method of embodiment 22, where the concentration of the antioxidant and/or chelating agent in the solution is about 50 mM.

Embodiment 26

The method according to any one of embodiments 1-25, where the detergent is an ionic detergent or a non-ionic detergent.

Embodiment 27

The method according to any one of embodiments 1-25, where the detergent includes a detergent selected from the group consisting of N-lauroylsarcosine, sodium dodecyl sulfate (SDS), cetyl methyl ammonium bromide (CTAB), TRITON®-X-100, n-octyl-β-D-glucopyranoside, CHAPS, n-octanoylsucrose, n-octyl-β-D-maltopyranoside, n-octyl-β-D-thioglucopyranoside, PLURONIC® F-127, TWEEN® 20, and n-heptyl-β-D-glucopyranoside.

Embodiment 28

The method of embodiment 27, where the detergent includes N-lauroylsarcosine.

Embodiment 29

The method of embodiment 27, where the detergent includes SDS.

Embodiment 30

The method according to any one of embodiments 1-29, where the detergent includes about 0.1% to about 2% of the solution.

Embodiment 31

The method of embodiment 30, where the detergent includes about 0.2% to about 1% of the solution.

Embodiment 32

The method according to any one of embodiments 1-29, where the concentration of the detergent in the solution ranges from about 10 mM up to about 100 mM.

Embodiment 33

The method of embodiment 32, where the concentration of the detergent in the solution ranges from about 20 mM up to about 50 mM.

Embodiment 34

The method of embodiment 32, where the concentration of the detergent in the solution ranges from about 30 mM up to about 40 mM.

Embodiment 35

The method according to any one of embodiments 1-34, where the solution further includes a second detergent.

Embodiment 36

The method of embodiment 35, where the second detergent includes TWEEN 20.

Embodiment 37

The method of embodiment 36, where the second detergent includes about 10 mM up to about 100 mM of the lysis solution.

Embodiment 38

The method according to any one of embodiments 1-37, where the solution includes a second chaotrope and/or reducing agent.

Embodiment 39

The method of embodiment 38, where the second chaotrope includes urea.

Embodiment 40

The method according to any one of embodiments 37-39, where the second chaotrope and/or reducing agent is present at a concentration ranging from about 1 M up to about 10 M.

Embodiment 41

The method according to any one of embodiments 37-39, where the second chaotrope and/or reducing agent is present at a concentration of about 7 M.

Embodiment 42

The method according to any one of embodiments 1-41, where the solution further includes calcium chloride.

Embodiment 43

The method of embodiment 42, where the concentration of the calcium chloride ranges from about 5 mM to about 30 mM.

Embodiment 44

The method according to any one of embodiments 1-43, where the solution includes: tris buffer; EDTA; guanidine hydrochloride; SDS; Tween 20; urea; and calcium chloride.

Embodiment 45

The method of embodiment 44, where the Tris buffer is at about pH 7 and is present at a concentration of about 50 mM; the EDTA is present at a concentration of about 50 mM; the guanidine hydrochloride is present at a concentration of about 4 M; the SDS is present at a concentration of about 34.7 mM; the urea is present at a concentration of about 6 M; the Tween is present at about 10% (v/v); and the calcium chloride is present at a concentration of about 10 mM.

Embodiment 46

The method according to any one of embodiments 1-43, where the solution includes: guanidine thiocyanate; N-acetyl-L-cysteine; sodium citrate; N-Lauroylsarcosine; and the pH of the solution ranges from about pH 3.0 to about pH 5.5.

Embodiment 47

The method of embodiment 46, where the pH of the solution is about pH 3.5.

Embodiment 48

The method according to any one of embodiments 46-47, where the solution includes: guanidine thiocyanate at about 4.5M; about 1% N-acetyl-L-cysteine; about 25 mM sodium citrate; and about 0.40% N-Lauroylsarcosine.

Embodiment 49

The method of embodiment 53, where the solution further includes Trizma base.

Embodiment 50

The method of embodiment 56, where the pH of the solution is about pH 5.09.

Embodiment 51

The method according to any one of embodiments 56-50, where the solution includes: guanidine thiocyanate at about 4.5M; about 1% N-acetyl-L-cysteine; about 25 mM sodium citrate; and about 50 mM Trizma base.

Embodiment 52

The method according to any one of embodiments 1-51, where the incubating is for a time period that ranges from about 15 minutes up to about 90 minutes.

Embodiment 53

The method of embodiment 52, where the time period ranges from about 30 minutes to about 60 minutes.

Embodiment 54

The method according to any one embodiments 1-53, where the incubating is at a temperature ranging from about 70° C. about 95° C.

Embodiment 55

The method according to any one embodiments 1-54, where the incubating is at a temperature ranging up to about 80° C.

Embodiment 56

The method according to any one of embodiments 1, 2, and 4-55, where the incubation is for about 60 minutes at about 80° C. to provide an RNA extraction.

Embodiment 57

The method according to any one of embodiments 1-3, and 7-56, where the incubation is for about 30 minutes at about 90° C. to provide a DNA extraction.

Embodiment 58

The method according to any one of embodiments 1-57, where the recovering includes the addition of a lower alcohol to the solution.

Embodiment 59

The method of embodiment 58, where the lower alcohol includes ethanol or isopropanol.

Embodiment 60

The method according to any one of embodiments 1-59, where the one or more sections range in thickness from about 1 μm to about 15 μm.

Embodiment 61

The method of embodiment 60, where the one or more sections comprise a plurality of sections having a thickness of about 8 μm or less.

Embodiment 62

The method according to any one of embodiments 60-61, where the one or more sections comprise sections from a tissue sample from a cancerous tissue.

Embodiment 63

The method of embodiment 62, where the tissue sample includes a sample from a cancer selected from the group consisting of ovarian cancer, pancreatic cancer, lung cancer, hepatocarcinoma, melanoma, retinoblastoma, breast cancer, colorectal cancer, testicular cancer, leukemia, lymphoma, brain tumor, cervical carcinoma, sarcoma, prostate tumor, bladder tumor, tumor of reticuloendothelial tissue, Wilm's tumor, astrocytoma, glioblastoma, neuroblastoma, ovarian carcinoma, osteosarcoma, renal cancer, and head and neck cancer.

Embodiment 64

The method according to any one of embodiments 1-63, where the lysis solution further includes a protease.

Embodiment 65

The method of embodiment 1, where the protease is selected from the group consisting of proteinase K, trypsin, chymotrypsin, and papain.

Embodiment 66

The method according to any one of embodiments 1-63, where the method does not utilize a protease.

Embodiment 67

The method according to any one of embodiments 1-66, where the method does not include further steps of deparaffinization and/or additional reagents for deparaffinization.

Embodiment 68

The method according to any one of embodiments 1-67, where the method does not utilize an organic solvent for deparaffinization.

Embodiment 69

The method according to any one of embodiments 1-68, where the incubating is not in the presence of an organic solvent.

Embodiment 70

The method according to any one of embodiments 1-69, where the method further includes amplifying all or a portion of the nucleic acid.

Embodiment 71

The method of embodiment 70, where the method further including utilizing the nucleic acid as a template in a PCR amplification.

Embodiment 72

The method of embodiment 70, where the method further including utilizing the nucleic acid in RT PCR.

Embodiment 73

The method of embodiment 70, where the method further including amplifying the nucleic acid in a GeneXpert system.

Embodiment 74

The method according to any one of embodiments 1-73, where the nucleic acid is used to determine the presence and/or expression level of expression of at least one target RNA that is an mRNA.

Embodiment 75

The method according to any one of embodiments 1-73, where the nucleic acid is used to determine the presence and/or expression level of expression of at least one target RNA selected from the group consisting of KRT20, IGF2, ANXA10, CRH, ABL, ERBB1, ERBB2, ERBB3, ERBB4, ESR1, PGR, MPO, CDKN2A, MKI67, TOP2A, MCM5, BIRC5, MMP9, and MCM2, PTEN, APC, KRAS, GATA3, PIC3CA, MAP3K1, TP53, and mutations of any of these.

Embodiment 76

The method according to any one of embodiments 1-75, where alcohol and/or PEG is added to the lysis solution containing nucleic acids.

Embodiment 77

The method of embodiment 76, where the lysis solution is stored.

Embodiment 78

The method of embodiment 77, where the lysis solution is stored at about room temperature or at a temperature of about −80°.

Embodiment 79

The method according to any one of embodiments 77-78, where the lysis solution is stored over a period of at least 6 hours, or over a period of at least one day, or over a period of at least two days, or over a period of at least 4 days, or over a period of at least one week, or over a period of at least two weeks, or over a period of at least one month, or over a period of at least two months, or over a period of at least three months, or over a period of at least 6 months, or over a period of at least one year, or over a period of at least two years, or over a period of at least 5 years.

Embodiment 80

The method according to any one of embodiments 1-79, where nucleic acids are amplified from the original lysed samples two or more different times.

Embodiment 81

The method of embodiment 80, where the two or more different times are over a period at least 6 hours, or over a period of at least one day, or over a period of at least two days, or over a period of at least 4 days, or over a period of at least one week, or over a period of at least two weeks, or over a period of at least one month, or over a period of at least two months, or over a period of at least three months, or over a period of at least 6 months, or over a period of at least one year, or over a period of at least two years, or over a period of at least 5 years.

Embodiment 82

The method according to any one of embodiments 80-81, where a second or later amplification comprises a repeat test.

Embodiment 83

The method according to any one of embodiments 80-81, where a second or later amplification comprise a reflex cartridge test.

Embodiment 84

The method according to any one of embodiments 1-83, where the tissue sample includes a stained tissue.

Embodiment 85

The method of embodiment 84, where the stained tissue includes a Hematoxylin-stained and/or Eosin-stained tissue.

Embodiment 86

A method for quantitative measurement of gene expression of a target gene in a fixed paraffin embedded tissue sample including: extracting an RNA from a formalin-fixed paraffin-embedded biological tissue sample according to the method of any one of embodiments 1, 2, and 4-83; subjecting the extracted nucleic acid to amplification using a pair of oligonucleotide primers capable of amplifying a region of a target gene mRNA, to obtain an amplified sample; and determining the presence and/or quantity of the target gene mRNA.

Embodiment 87

The method of embodiment 86, where the quantity of the target gene mRNA is determined relative to the quantity of an internal control gene's mRNA from the isolated mRNA.

Embodiment 88

The method according to any one of embodiments 86-87, where determining the relative gene expression level includes using RT-PCR.

Embodiment 89

The method according to any one of embodiments 86-88, where the internal control gene is β-actin.

Embodiment 90

The method according to any one of embodiments 86-89, where the target gene is selected from the group consisting of an ALK gene rearrangement, alpha-fetoprotein (AFP), Beta-2-microglobulin (B2M), beta-human chorionic gonadotropin (beta-hCG), BCR-ABL fusion gene, BRAF mutation V600E, CA15-3/CA27.29, CA19-9, CA-125, calcitonin, carcinoembryonic antigen (CEA), CD20, chromogranin A (CgA), chromosome 3, chromosome 7, chromosome 17, chromosome 9p21, chromosome 20q13, cytokeratin fragments 21-1, EGFR mutation analysis, estrogen receptor (ER), progesterone receptor (PR), fibrin/fibrinogen, HE4, HER4, HER2/neu, KIT, KRAS mutation analysis, lactate dehydrogenase, nuclear matrix protein 22, prostate-specific antigen (PSA), thyroglobulin, urokinase plasminogen activator (uPA), and plasminogen activator inhibitor (PAI-1).

Embodiment 91

The method according to any one of embodiments 86-90, where the tissue sample includes a stained tissue.

Embodiment 92

The method of embodiment 91, where the stained tissue includes a hematoxylin-stained and/or eosin-stained tissue.

BRIEF DESCRIPTION OF THE DRAWINGS

FIG. 2A shows an example of mutation detected in a colon cancer FFPET sample. FIG. 2B shows the melt curve analysis for cell lines containing KRAS mutations (reference cell line CRL-1469).

DETAILED DESCRIPTION

Formalin-fixed, paraffin-embedded tissue (FFPET) samples represent the most commonly collected and stored samples for use in the diagnosis and prognosis of diseases, including, but not limited to, cancer. Nevertheless, historically these samples have been underutilized for the purpose of gene expression profiling because of the poor quality and quantity of FFPET nucleic acids. The analysis of nucleic acids from formalin fixed, paraffin embedded tissue (FFPET) is challenging due to the multiple steps required for generating amplifiable (e.g., PCR-amplifiable) genetic material. The procedure to isolate nucleic acids from FFPET has typically involved removal of paraffin (deparaffinization), lysis of preserved sample (protease digestion), reversal of cross-links acquired during the fixation process, and solid phase-based purification of nucleic acids.

There are various sample-prep procedures for extracting PCR-ready DNA/RNA, but most are complex and labor intensive. The methods described herein overcome these and other problems and provide reagents and protocols that can be used to rapidly isolate amplifiable quality nucleic acid samples (e.g., DNA, RNA). The methods provided are simple method (easily semi- or fully-automated) requiring minimal hands-on time. The nucleic acids are extracted at high yield and are of PCR-amplifiable quality.

Figure 1:
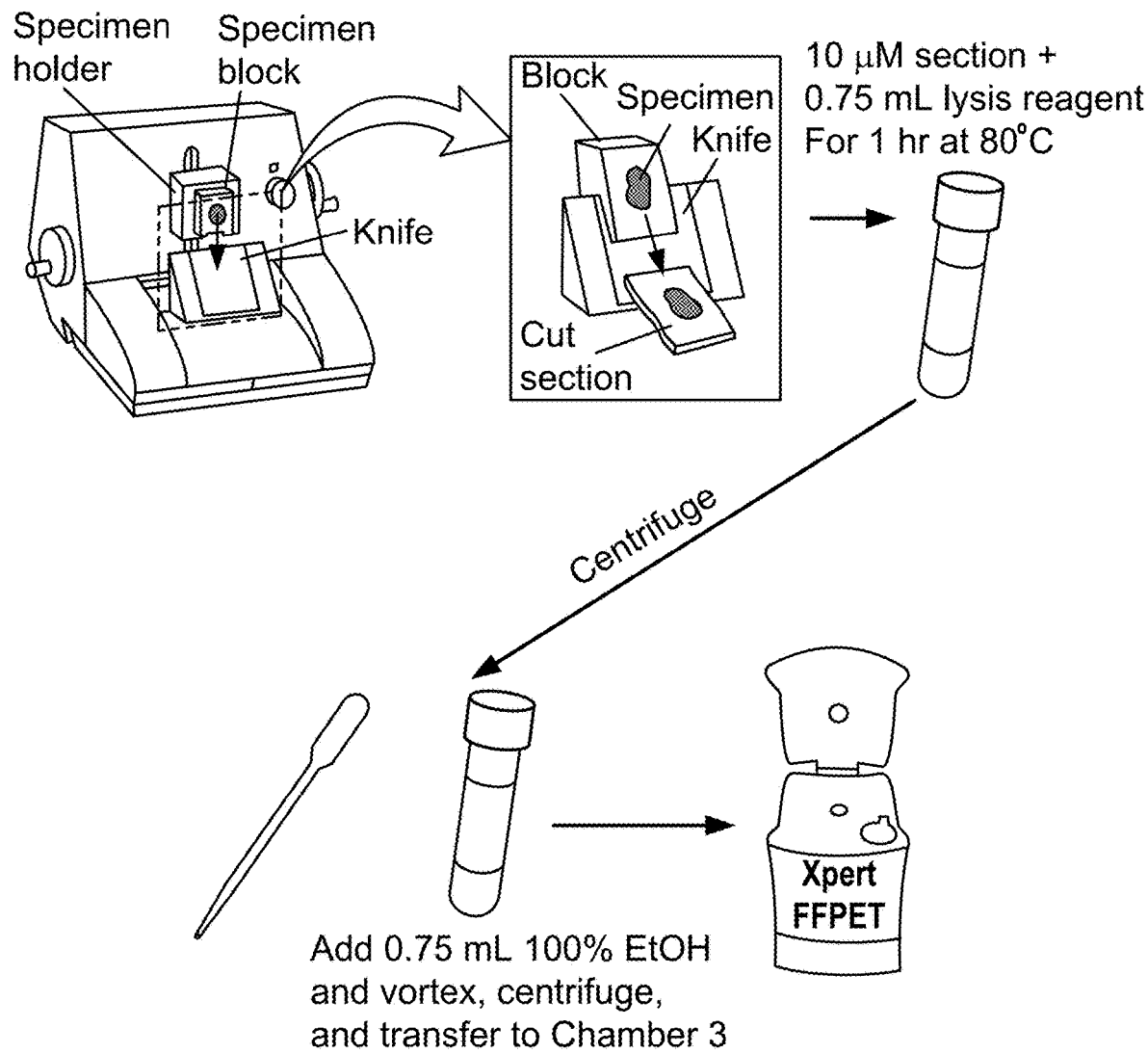
FIG. 1 schematically illustrates one embodiment of an FFPET GENEXPERT® workflow.

One embodiment of the methods is schematically illustrated in FIG. 1. As shown therein, one or more sections of a fixed, paraffin embedded, tissue sample, are incubated in a lysis solution at a temperature ranging from about 50° C. to about 110° C. The nucleic acids are then released from the lysis solution, e.g., using an alcohol extraction (e.g., an alcohol precipitation). The procedure results in a relatively high yield extraction and produces a nucleic acid (e.g., DNA, RNA) of sufficient quality for PCR amplification, detection, and/or quantification of a target nucleic acid sequence. In some embodiments the incubating is for a period of time up to about 3 hours. However, in typical embodiments, the incubating can range from about 15, 20, or 30 minutes up to about 1 hour. In some embodiments no protease is required. Similarly, in some embodiments, the does not include further steps of deparaffinization and/or additional reagents for deparaffinization. In some embodiments the method does not utilize an organic solvent for deparaffinization and/or the incubating is not in the presence of an organic solvent. According, the method is rapid, simple, and easily amenable to automation and high throughput methodologies.

The nucleic acids extracted using the methods and reagents described herein are of good quality and can readily be amplified to detect and/or quantify one or more target nucleic acid sequences in the sample. The nucleic acids are compatible with any of a number of amplification methods including, but not limited to polymerase chain reaction (PCR) (see. e.g., Innis, et al. (1990) *PCR Protocols. A guide to Methods and Application*. Academic Press, Inc. San Diego,) including RT-PCR, ligase chain reaction (LCR) (see, e.g., Wu and Wallace (1989) *Genomics* 4: 560; Landegren et al. (1988) *Science* 241: 1077; Barringer et al. (1990) *Gene* 89: 117), transcription amplification (see, e.g., Kwoh et al. (1989) *Proc. Natl. Acad. Sci. USA* 86: 1173), self-sustained sequence replication (see, e.g., Guatelli et al. (1990) *Proc. Nat. Acad. Sci. USA* 87: 1874), dot PCR, linker adapter PCR, and the like.

Moreover it was a surprising discovery that samples processed in accordance with the methods using the materials described herein, particularly using the CT-NG lysis solution(s) described herein, e.g., at pH ~3.50 (see, Table 14, below) gave much earlier Ct results, sometimes better than 4 Cts, as compared to the BCR-ABL lysis (see Table 11, below) samples. In addition, while the samples were in the CT/NG lysis reagent, particularly with PEG 200 added, they gave consistent results across time (e.g., 0 hr, 4 hr, day 3, and day 5) indicating that the samples were stable in this condition. It was thus possible to measure multiple pulls from the original lysed scroll to perform either a repeat test (if needed) or reflex cartridge test(s).

While in some embodiments, the extracted nucleic acids are used in amplification reactions, other uses are also contemplated. Thus, for example, the extracted nucleic acids (or their amplification product(s)) can be used in various hybridization protocols including, but not limited to nucleic acid based microarrays. In some embodiments any nucleic acid-based microarray can be used with the methods described herein. Such microarrays include but are not limited to, commercially available microarrays, for example microarrays available from Affymetrix, Incorporated, Agilent Technologies, Incorporated, Illumina, Incorporated (San Diego, Calif.), GE Healthcare (Piscataway, N.J.), NimbleGen Systems, Incorporated (Madison, Wis.), Invitrogen Corporation (Carlsbad, Calif.), and the like.

The methods and reagents described herein are thus applicable to basic research aimed at the discovery of gene expression profiles relevant to the diagnosis and prognosis of disease. The methods are also applicable to the diagnosis and/or prognosis of disease, the determination particular treatment regiments, monitoring of treatment effectiveness and the like. In some embodiments the methods are also applicable to other fields where the quality of nucleic acid is poor, such as forensics, archeology, medical history, paleontology, and the like. In view of the teachings and protocols provided herein, these and other applications will readily be recognized by those of skill in the art.

Samples

Using the methods described herein DNA and/or RNA can be isolated from any biological sample. The methods are particularly well suited for use with fixed paraffin-embedded tissue (e.g., FFPET) samples. While histological samples are typically fixed with an aldehyde fixative such as formalin (formaldehyde) and glutaraldehyde, it is believed the methods described herein additionally work with tissues fixed using other fixation techniques such as alcohol immersion, and the like.

Illustrative samples include, but are not limited to, FFPET samples from human tissues, laboratory animal tissues, companion animal tissues, or livestock animal tissues. Thus, for example, the samples include tissue samples from humans including, but not limited to samples from healthy humans (e.g., healthy human tissue samples), samples from a diseased subject and/or diseased tissue, samples used for diagnostic and/or prognostic assays and the like. Suitable samples also include samples from non-human animals. FFPET samples from, for example, a non-human primate, such as a chimpanzee, gorilla, orangutan, gibbon, monkey, macaque, baboon, mangabey, colobus, langur, marmoset, lemur, a mouse, rat, rabbit, guinea pig, hamster, cat dog, ferret, fish, cow, pig, sheep, goat, horse, donkey, chicken, goose, duck, turkey, amphibian, or reptile can be used in the methods described herein.

In addition, FFPET samples of any age can be used with the methods described herein including, but not limited to, FFPET samples that are fresh, less than one week old, less than two weeks old, less than one month old, less than two months old, less than three months old, less than six months old, less than 9 months old, less than one year old, at least one year old, at least two years old, at least three years old, at least four years old, at least five years old, at least six years old, at least seven years old, at least eight years old, at least nine years old, at least ten years old, at least fifteen years old, at least twenty years old, or older.

In some embodiments the methods described herein are performed on one or more sections taken from a fixed, embedded tissue sample (e.g., an FFPET sample). The sections can be of any desired thickness. Thus, in some embodiments, both thin sections or thick sections are contemplated, including, but not limited to, sections that are less than 1 micron thick, about 1 micron thick, about 2 microns thick, about 3 microns thick, about 4 microns thick, about 5 microns thick, about 6 microns thick, about 7 microns thick, about 8 microns thick, about 9 microns thick, about 10 microns thick, about 15 microns thick, or about 20 microns thick, depending upon the desired application. In certain applications, the sections can be, for example, up to about 1 micron thick, up to about 2 microns thick, up to about 3 microns thick, up to about 4 microns thick, up to about 5 microns thick, up to about 6 microns thick, up to about 7 microns thick, up to about 8 microns thick, up to about 9 microns thick, up to about 10 microns thick, up to about 15 microns thick, up to about 20 microns thick, or up to about 25 or 30 microns thick. In some embodiments, the sections can be defined by a range of sizes, including, but not limited to, between about 1 and about 5 microns thick, between about 1 and about 20 microns thick, between about 1 and about 10 microns thick, or between about 5 and about 10 microns thick.

In many cases, the fixed embedded tissue samples (e.g., FFPET samples) comprise an area of diseased tissue, for example a tumor or other cancerous tissue. While such FFPET samples find utility in the methods described herein, FFPET samples that do not comprise an area of diseased tissue, for example FFPET samples from normal, untreated, placebo-treated, or healthy tissues, also can be used in the methods described herein. In some embodiments of the methods described herein, a desired diseased area or tissue, or an area containing a particular region, feature or structure within a particular tissue, is identified in a FFPET sample, or a section or sections thereof, prior to isolation of nucleic acids as described herein, in order to increase the percentage of nucleic acids obtained from the desired region. Such regions or areas can be identified using any method known to those of skill in the art, including, but not limited to, visual identification, staining, for example hematoxylin and eosin staining, immunohistochemical labeling, and the like. In any event, in some embodiments, the desired area of the tissue sample, or sections thereof, can be dissected, either by macrodissection or microdissection, to obtain the starting material for the isolation of a nucleic acid sample using the methods described herein.

In certain illustrative, but non-limiting embodiments, the sample comprises a diseased area or tissue comprising cells from a cancer. In some embodiments the cancer comprises a cancer selected from the group consisting of acute lymphoblastic leukemia (ALL), acute myeloid leukemia (AML), Adrenocortical carcinoma, AIDS-related cancers (e.g., kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sezary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sezary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, Wilm's tumor, and the like.

It will be recognized that the methods described herein are believed to be compatible with essentially any fixed (e.g., formalin fixed, glutaraldehyde fixed, etc.) paraffin embedded tissue sample. Such samples include, but are not limited to biopsies and fine needle aspirates and archived samples (e.g. tissue microarrays), and the like.

Lysis Solution

As indicated above, in some embodiments, the methods comprise incubating one or more paraffin embedded fixed tissue samples in a lysis solution at a desired temperature (e.g., about 50° C. to about 100° C.) for a desired time (e.g., about 30 minutes to about 60 or about 90 minutes). In some embodiments, the lysis solution comprises a buffer sufficient to maintain the pH of the solution at a pH ranging from about pH 3 or about pH 4 to about pH 6, or about pH 7, or about pH 8, or about pH 9. In some embodiments the solution additionally comprises one or more a chaotropic agent(s), and/or one or more chelating agents, and/or one or more detergents. In some embodiments the lysis solution additionally contains one or more of the following: a second chaotrope/denaturing agent, and/or a second detergent, and/or calcium chloride or equivalent salt. One illustrative, but non-limiting lysis solution is shown in Table 1.

TABLE 1

Illustrating, but non-limiting lysis solution.

| Component | Concentration in Buffer | U/M |
|---|---|---|
| Water, Molecular Biology Grade | n/a | n/a |
| Buffer e.g., Tris, 1M, pH 7.0 | 50 | mM |
| Chaotrope e.g, Guanidine Hydrochloride | 4 | M |
| Antioxidant and/or Chelating agent e.g., EDTA | 50 | mM |
| Detergent e.g., Sodium Dodecyl Sulphate (SDS) (1% (v/v) | 34.7 | mM |

Another illustrative, but non-limiting (CT/NG) lysis solution is shown in Table 2.

TABLE 2

CT/NG lysis solution pH 3.5.
CT/NG Lysis Reagent (PN 500-1511)

| Chaotrope e.g, Guanidine Thiocyanate | 4.5M |
|---|---|
| Antioxidant and/or Chelating agent N-acetyl-L-cysteine | 1% |
| Buffer e.g, sodium citrate | 25 mM |
| Detergent e.g, N-Lauroylsarcosine | 0.40% |
| final pH | ~3.5 |

Buffer

In some embodiments, the lysis solution comprises a buffer that buffers the solution at a pH ranging from about pH 3 up to about pH 9. In some embodiments the buffer buffers the solution at a pH ranging from about pH 4 or pH 5 up to about pH 8. In some embodiments the buffer buffers the solution at a pH ranging from about pH 3, or about pH 3.5, about pH 4, or about pH 4.5, or about pH 5, or about pH 5.5, or about pH 6 up to about pH 8, or up to about pH 7. In some embodiments the solution is buffered at about pH 7. In some embodiments, the solution is buffered at about pH 3 to about pH 4, and in some embodiments, the solution is buffered at about pH 3 or at about pH 3.5.

Any of a number of buffers used in biology are suitable. Such buffers are well known and include, but are not limited to buffers such as citrate buffer, Tris, phosphate, PBS, citrate, TAPS, Bicine, Tricine, TAPSO, HEPES, TES, MOPS, PIPES, Cacodylate, SSC, MES, and the like. An illustrative, but non-limiting list of buffer compounds is provided in Table 3.

TABLE 3

Common buffers that can be used in a lysis solution.

| Common Name | $pK_a$ at 25° C. | Buffer Range | Temp Effect dpH/dT in (1/K) ** | Mol. Weight | Full Compound Name |
|---|---|---|---|---|---|
| TAPS | 8.43 | 7.7-9.1 | −0.018 | 243.3 | 3-{[tris(hydroxymethyl)methyl]amino}propanesulfonic acid |
| Bicine | 8.35 | 7.6-9.0 | −0.018 | 163.2 | N,N-bis(2-hydroxyethyl)glycine |
| Tris | 8.06 | 7.5-9.0 | −0.028 | 121.14 | tris(hydroxymethyl)methylamine |
| Tricine | 8.05 | 7.4-8.8 | −0.021 | 179.2 | N-tris(hydroxymethyl)methylglycine |
| TAPSO | 7.635 | 7.0-8.2 | | 259.3 | 3-[N-Tris(hydroxymethyl)methylamino]-2-hydroxypropanesulfonic Acid |

TABLE 3-continued

Common buffers that can be used in a lysis solution.

| Common Name | pK$_a$ at 25° C. | Buffer Range | Temp Effect dpH/dT in (1/K) ** | Mol. Weight | Full Compound Name |
|---|---|---|---|---|---|
| HEPES | 7.48 | 6.8-8.2 | −0.014 | 238.3 | 4-2-hydroxyethyl-1-piperazineethanesulfonic acid |
| TES | 7.40 | 6.8-8.2 | −0.020 | 229.20 | 2-{[tris(hydroxymethyl)methyl]amino}ethanesulfonic acid |
| MOPS | 7.20 | 6.5-7.9 | −0.015 | 209.3 | 3-(N-morpholino)propanesulfonic acid |
| PIPES | 6.76 | 6.1-7.5 | −0.008 | 302.4 | piperazine-N,N'-bis(2-ethanesulfonic acid) |
| Cacodylate | 6.27 | 5.0-7.4 | | 138.0 | dimethylarsinic acid |
| SSC | 7.0 | 6.5-7.5 | | 189.1 | saline sodium citrate |
| MES | 6.15 | 5.5-6.7 | −0.011 | 195.2 | 2-(N-morpholino)ethanesulfonic acid |
| Citrate | | | | | Sodium citrate |

** Values are approximate.

In one illustrative, but non-limiting embodiment, the buffer is a Tris buffer at pH 7 and a concentration of 50 mM. In another illustrative, but non-limiting embodiment, the buffer is a citrate buffer (e.g., sodium citrate at about 10 mM to about 100 mM, or about 15 mM to about 50 mM, or at about 20 mM to about 40 mM, or at about 25 mM).

The various buffers described above are intended to be illustrative and not limiting. Using the teaching and examples provided herein, numerous other buffers for use in a lysis solution in accordance with the methods described herein will be available to one of skill in the art.

Chaotrope

As indicated above, in some embodiments, the lysis solution comprises one or more chaotropes (chaotropic agent(s)). Chaotropic agents are well known to those of skill in the art and include, but are not limited to, 1-octanesulfonic acid sodium salt, ammonium sulfate, butanol, dithiothreitol, ethanol, guanidinium hydrochloride, guanidinium thiocyanate, lithium chloride, lithium perchlorate, magnesium chloride, phenol, propanol, sodium dodecyl sulfate, thiourea, tributyl phosphate, urea, and the like. In some embodiments the chaotropic agent comprises a chaotropic salt (lithium perchlorate, magnesium chloride, guanidinium salts, lithium chloride, and the like). In some embodiments, the chaotropic agent comprises a guanidinium compound. In some embodiments, the guanidinium compound comprises guanidinium hydrochloride and/or guanidinium thiocyanate. In some embodiments the chaotropic agent(s) do not include an alcohol and/or an organic solvent. In some embodiments, the chaotropic agent(s) do not include organic solvents that dissolve/solubilize paraffin.

In some embodiments, when present the chaotropic agent(s) are present in the lysis solution at a concentration ranging from about 1 M up to about 10 M, or from about 2 M, or from about 2.5 M, or from about 3 M, up to about 7 M, or up to about 8 M or up to about 9 M. In some embodiments, the chaotropic agents are present at a concentration of about 1 M, or about 1.5 M, or about 2 M, or about 2.5 M, or about 3 M, or about 3.5 M, or about 4 M, or about 4.5 M, or about 5 M, or about 5.5 M, or about 6 M, or about 6.5 M, or about 7 M, or about 7.5 M, or about 8 M, or about 8.5 M, or about 9 M, or about 9.5 M, or about 10 M, or in some embodiments at even higher concentrations. In some embodiments the chaotropic agent is present at a concentration of about 4 M, or about 4.5 M. In some embodiments, the chaotropic agent is present in the lysis solution at a concentration of about 7 M.

In some embodiments, the lysis solutions in the methods described herein need not be limited to the use of the chaotropic agents described above. Using the teaching and examples provided herein, other chaotropic agents will be available to one of skill in the art.

Antioxidant and/or Chelating Agent

As indicated above, in some embodiments, the lysis solution comprises one or more antioxidant and/or chelating agents. Antioxidant and/or chelating agents are well known to those of skill in the art and include, but are not limited to N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N,N',N'-tetraacetic acid (BAPTA), and phosphonate chelating agents (e.g., including, but not limited to nitrilotris(methylene)phosphonic acid (NTMP), ethylenediamine tetra(methylene phosphonic acid) (EDTMP), diethylenetriamine penta(methylene phosphonic acid (DTPMP), 1-hydroxy ethylidene-1,1-diphosphonic acid (HEDP), and the like). In some embodiments the chelating agent comprises EDTA, or DTAP. In some embodiments, the chelating agent comprises EDTA. In some embodiments, the chelating agent comprises N-acetyl-L-cysteine.

In some embodiments, when present, the antioxidant and/or chelating agent is present in the lysis solution at a concentration ranging from about 5 mM up to about 200 mM, or from about 10 mM up to about 100 mM. In some embodiments, the antioxidant and/or chelating agent is present at a concentration ranging from about 10 mM, or from about 20 mM, or from about 30 mM, or from about 40 mM up to about 60 mM, or up to about 70 mM, or up to about 80 mM, or up to about 90 mM, or up to about 100 mM. In some embodiments, the antioxidant and/or chelating agent is present at a concentration of about 50 mM. In some embodiments, the antioxidant and/or chelating agent comprises 0.5% to about 5% of the lysis solution. In some embodiments, the antioxidant and/or chelating agent comprises 0.5% to about 3%, or to about 2%, or to about 1.5% of the lysis solution. In some embodiments, the antioxidant and/or chelating agent comprises 1% of the lysis solution.

In some embodiments the chelating agent EDTA, or DTAP at a concentration of about 4 M. In some embodiments, the chelating agent comprises EDTA at a concentration of about 4 M.

In some embodiments the chelating agent comprises EDTA, or DTAP at a concentration of about 35 mM. In some embodiments, the chelating agent comprises EDTA at a concentration of about 35 mM.

In some embodiments, the antioxidant and/or chelating agent is N-acetyl-L-cysteine comprising 0.5% to about 3%, or to about 2%, or to about 1.5% of the lysis solution. In some embodiments, the antioxidant and/or chelating agent is N-acetyl-L-cysteine comprising about 1% of the lysis solution.

In some embodiments, the lysis solutions in the methods described herein need not be limited to the use of the chelating agents described above. Using the teaching and examples provided herein, other chelating agents will be available to one of skill in the art.

Detergent

As indicated above, in some embodiments, the lysis solution comprises one or more detergents. In some embodiments, the detergent comprises an ionic detergent or a non-ionic detergent. In some embodiments, the detergent includes one or more detergents shown in Table 4.

TABLE 4

Illustrative, but non-limiting detergents for use in some embodiments of the lysis solution described herein.

| Description | M | Formula | Class |
|---|---|---|---|
| Benzethonium chloride | 448.08 | $C_{27}H_{42}ClNO_2$ | cationic |
| Brij ® 35 | 1198.56 | $C_{58}H_{118}O_{24}$ | nonionic |
| Brij ® 58 | 1123.51 | $C_{56}H_{114}O_{21}$ | nonionic |
| Cetylpyridinium chloride monohydrate | 358.01 | $C_{21}H_{38}ClN \cdot H2O$ | cationic |
| Cetyltrimethylammonium bromide | 364.46 | $C_{19}H_{42}BrN$ | cationic |
| CHAPS | 614.89 | $C_{32}H_{58}N2O7S$ | zwitterionic |
| CHAPSO | 630.87 | $C_{32}H_{58}N2O8S$ | zwitterionic |
| 1-Decanesulfonic acid sodium salt | 244.33 | $C_{10}H_{21}NaO3S$ | anionic |
| n-Decyl-β-D-glucopyranoside | 320.43 | $C_{16}H_{32}O_6$ | nonionic |
| n-Decyl-β-D-maltoside | 482.57 | $C_{22}H_{42}O_{11}$ | nonionic |
| Deoxy-BIGCHAP | 862.07 | $C_{42}H_{75}N_3O_{16}$ | nonionic |
| Digitonin | 1229.34 | $C_{56}H_{92}O_{29}$ | nonionic |
| 1-Dodecanesulfonic acid sodium salt | 272.38 | $C_{12}H_{35}NaO_3S$ | anionic |
| n-Dodecyl-β-D-glucopyranoside | 348.48 | $C_{18}H_{36}O_6$ | nonionic |
| Dodecyl-β-D-maltoside | 510.63 | $C_{24}H_{46}O_{11}$ | nonionic |
| Dodecyltrimethylammonium bromide | 308.35 | $C_{15}H_{34}BrN$ | cationic |
| HECAMEG | 335.39 | $C_{15}H_{29}NO_7$ | nonionic |
| 1-Heptanesulfonic acid sodium salt anhydrous | 202.25 | $C_7H_{15}NaO_3S$ | anionic |
| 1-Heptanesulfonic acid sodium salt monohydrate | 220.27 | $C_7H_{15}NaO_3S \cdot H2O$ | anionic |
| 1-Hexanesulfonic acid sodium salt anhydrous | 188.22 | $C_6H13NaO_3S$ | anionic |
| 1-Hexanesulfonic acid sodium salt monohydrate | 206.24 | $C_6H_{13}NaO_3S \cdot H2O$ | anionic |
| n-Lauroylsarcosine sodium salt | 293.39 | $C_{15}H_{28}NNaO3$ | anionic |
| Lithium dodecylsulfate (LiDS) | 272.33 | $C_{12}H_{25}LiO_4S$ | anionic |
| MEGA-8 | 321.42 | $C_{15}H_{31}NO_6$ | nonionic |
| MEGA-9 | 335.44 | $C_{16}H_{33}NO_6$ | nonionic |
| 1-Nonanesulfonic acid sodium salt | 230.30 | $C_9H_{19}NaO_3S$ | anionic |
| n-Nonyl-β-D-glucopyranoside | 306.40 | $C_{15}H_{30}O_6$ | nonionic |
| n-Nonyl-β-D-maltoside | 468.41 | $C_{21}H_{40}O_{11}$ | nonionic |
| 1-Octanesulfonic acid sodium salt | 216.28 | $C_8H_{17}NaO_3S$ | anionic |
| n-Octyl-β-D-glucopyranoside | 292.38 | C14H28O6 | nonionic |
| n-Octyl-β-D-thioglucopyranoside | 308.44 | $C_{14}H_{28}O_5S$ | nonionic |
| Octyl-D-glucopyranoside | 292.38 | $C_{14}H_{28}O6$ | nonionic |
| 1-Pentanesulfonic acid sodium salt anhydrous | 174.20 | $C_5H_{11}NaO_3S$ | anionic |
| 1-Pentanesulfonic acid sodium salt monohydrate | 192.12 | $C_5H_{11}NaO_3S \cdot H2O$ | anionic |
| Pluronic ® F-68 | ~8350 | | nonionic |
| Saponin | | | nonionic |
| SDS (Sodium dodecylsulfate) | 288.38 | $C_{12}H_{25}NaO_4S$ | anionic |
| Sodium cholate | 430.57 | $C_{24}H_{39}NaO_5$ | anionic |
| Sodium deoxycholate | 414.57 | $C_{24}H_{39}NaO_4$ | anionic |
| Sucrose monolaurate | 524.60 | $C_{24}H_{44}O_{12}$ | nonionic |

TABLE 4-continued

Illustrative, but non-limiting detergents for use in some
embodiments of the lysis solution described herein.

| Description | M | Formula | Class |
|---|---|---|---|
| Sulfobetaine SB 12 | 335.55 | $C_{17}H_{37}NO_3S$ | zwitterionic |
| Sulfobetaine SB 14 | 363.60 | $C_{19}H_{41}NO_3S$ | zwitterionic |
| n-Tetradecyl-β-D-maltoside | 538.63 | $C_{26}H_{50}O_{11}$ | nonionic |
| n-Tridecyl-β-D-maltoside | 524.64 | $C_{25}H_{48}O_{11}$ | nonionic |
| Triton ® X-100 | 646.85 | $C_{34}H_{62}O_{11}$ | nonionic |
| Triton ® X-114 | 558.75 | $C_{30}H_{54}O_9$ | nonionic |
| Tween ® 20 | 1227.72 | $C_{58}H_{114}O_{26}$ | nonionic |
| Tween ® 80 | 1310 | | nonionic |
| n-Undecyl-β-D-maltoside | 496.59 | $C_{23}H_{44}O_{11}$ | Nonionic |
| N-Lauroylsarcosine | | $CH_3(CH_2)_{10}CON(CH_3)CH_2COOH$ | anionic |

In some embodiments the detergent comprises sodium dodecylsulfate (SDS) and/or Tween. In some embodiments, the detergent comprises SDS. In some embodiments, the detergent comprises N-Lauroylsarcosine.

In some embodiments, when present, the detergent is present in the lysis solution at a concentration ranging from about 5 mM up to about 200 mM, or from about 10 mM up to about 100 mM, or from about 20 mM up to about 50 mM, or from about 30 mM up to about 40 mM. In some embodiments the detergent ranges from about 5 mM, or from about 10 mM, or from about 15 mM or from about 20 mM or from about 25 mM up to about 200 mM or up to about 150 mM, or up to about 100 mM, or up to about 75 mM, or up to about 50 mM, or up to about 40 mM. In some embodiments, the detergent is present at a concentration of about 35 mM. In some embodiments, the detergent is present at a percentage ranging from about 0.5% (v/v) up to about 30% (v/v), or from about 1% (v/v) up to about 20% (v/v) or from about 5% up to about 15% (v/v). In some embodiments the detergent is present at about 10% (v/v). In some embodiments the detergent comprises from about 0.1%, or from about 0.2% up to about 3% or up to about 2%, or up to about 1% of the lysis solution. In certain embodiments the detergent comprises about 0.2% to about 09.4% of the lysis solution. In certain embodiments the detergent comprises N-lauroylsarcosine at about 0.4% of the lysis solution.

In some embodiments, the detergents used in the lysis solutions described herein need not be limited to the detergents described above. Using the teaching and examples provided herein, other detergents will be available to one of skill in the art.

Additional Components

In some embodiments, the lysis solution additionally comprises one or more of the following: a second detergent, a second chaotrope and/or reducing agent, calcium chloride or other salt, and/or a protease.

Second Detergent

As indicated above, in some embodiments, the lysis solution additionally comprises a second detergent (different than the first detergent(s)). In some embodiments, the second detergent comprises an ionic detergent or a non-ionic detergent. In some embodiments, the second detergent includes one or more detergents shown in Table 4. In some embodiments, the second detergent comprises TWEEN® 20.

In some embodiments, when present, the second detergent is present in the lysis solution at a concentration ranging from about 5 mM up to about 200 mM, or from about 10 mM up to about 100 mM, or from about 20 mM up to about 50 mM, or from about 30 mM up to about 40 mM. In some embodiments the detergent ranges from about 5 mM, or from about 10 mM, or from about 15 mM or from about 20 mM or from about 25 mM up to about 200 mM or up to about 150 mM, or up to about 100 mM, or up to about 75 mM, or up to about 50 mM, or up to about 40 mM. In some embodiments, the second detergent is present at a concentration of about 34 mM. In some embodiments, the detergent is present at a percentage ranging from about 0.5% (v/v) up to about 30% (v/v), or from about 1% (v/v) up to about 20% (v/v) or from about 5% up to about 15% (v/v). In some embodiments the detergent is present at about 10% (v/v).

In some embodiments, the second detergent comprises TWEEN® 20 at about 10% (v/v) in the lysis solution.

In some embodiments, second detergents that can be used in the lysis solutions described herein need not be limited to the detergents described above. Using the teaching and examples provided herein, other second detergents will be available to one of skill in the art.

Second Chaotrope and/or Reducing Agent

In some embodiments, the lysis solution additionally comprises a second chaotrope and/or reducing agent different than the first chaotrope. Suitable second chaotropes and/or reducing agents include, but are not limited to, 1-octanesulfonic acid sodium salt, ammonium sulfate, butanol, dithiothreitol, ethanol, guanidinium hydrochloride, guanidinium thiocyanate, lithium chloride, lithium perchlorate, magnesium chloride, phenol, propanol, sodium dodecyl sulfate, thiourea, tributyl phosphate, urea, and the like. In some embodiments the chaotropic agent comprises a chaotropic salt (lithium perchlorate, magnesium chloride, guanidinium salts, lithium chloride, and the like). In some embodiments, the chaotropic agent comprises a guanidinium compound. In some embodiments, the guanidinium compound comprises guanidinium hydrochloride and/or guanidinium thiocyanate. In some embodiments the chaotropic agent(s) do not include an alcohol and/or an organic solvent. In some embodiments, the chaotropic agent(s) do not include organic solvents that dissolve/solubilize paraffin.

In some embodiments, the second chaotrope comprises urea or thiourea. In some embodiments, the second chaotrope comprises urea.

In some embodiments, when present the second chaotropic agent(s) and/or reducing agent is present in the lysis solution at a concentration ranging from about 1 M up to about 10 M, or from about 2 M or from about 3 M up to about 7 M, or up to about 8 M or up to about 9 M. In some embodiments, the chaotropic agents are present at a concentration of about 1 M, or about 2 M, or about 3 M, or about 4 M, or about 5 M, or about 6 M, or about 7 M, or about 8 M, or about 9 M, or about 10 M, or in some embodiments at even higher concentrations. In some embodiments the second chaotropic agent is present at a concentration of about 6 M.

In some embodiments, the second chaotrope comprises urea or thiourea at a concentration of about 6 M. In some embodiments, the second chaotrope comprises urea at a concentration of about 6 M.

In some embodiments, the lysis solutions in the methods described herein need not be limited to the use of the chaotropic agents described above. Using the teaching and examples provided herein, other chaotropic agents will be available to one of skill in the art.

Calcium Chloride or Other Salt

In some embodiments, the lysis solution additionally includes calcium chloride or equivalent salts.

When present the calcium chloride (or other salt) is present in the lysis solution at a concentration ranging from about 1 mM up to about 50 mM, or from about 2 mM up to about 40 mM, or up to about 30 mM. In some embodiments, the salt is present at a concentration ranging from about 1 mM, or about 2 mM or about 5 mM, or about 8 mM up to about 50 mM, or up to about 40 mM, or up to about 30 mM, or up to about 20 mM, or up to about 15 mM, or up to about 10 mM. In some embodiments, the salt is present at a concentration of about 10 mM.

Protease

In some embodiments the lysis solution additionally includes one or more proteases. Suitable proteases include, but are not limited to serine proteases, threonine proteases, cysteine proteases, aspartate proteases, metalloproteases, glutamic acid proteases, metalloproteases, and combinations thereof. Illustrative suitable proteases include, but are not limited to proteinase k (a broad-spectrum serine protease), subtilysin trypsin, chymotrypsin, pepsin, papain, and the like.

In some embodiments, when present in the lysis solution the protease is present at an amount that provides an activity that ranges from 1 U/ml up to about 200 U/ml of lysis solution. In some embodiments, the amount provides an activity ranging from about 1 U/ml, or from about 5 U/ml, or from about 10 U/ml, or from about 15 U/ml, up to about 200 U/ml, or up to about 100 U/ml, or up to about 80 U/ml, or up to about 60 U/ml, or up to about 40 U/ml, or up to about 30 U/ml of lysis solution. In some embodiments, the amount of protease ranges from about 0.05 to about 5 mg/ml. In some embodiments, the amount of protease ranges from about 0.1 mg/mL, or about 0.2 mg/mL, or about 0.3 mg/mL, or about 0.4 mg/mL, or about 0.5 mg/mL, or about 0.6 mg/mL, or about 0.7 mg/mL, or about 0.8 mg/mL up to about 5 mg/mL, or up to about 4 mg/mL, or up to about 3 mg/mL, or up about 2 mg/Ml, or up to about 1 mg/mL.

In some embodiments, the lysis solutions in the methods described herein need not be limited to the use of the proteases described above. Using the teaching and examples provided herein, other proteases will be available to one of skill in the art.

Lysis Solutions for Both DNA and RNA

In some embodiments the protocols and lysis solutions described herein are well suited for either RNA or DNA extraction. Accordingly, in such embodiments a single lysis solution and extraction protocol can be used to extract essentially any nucleic acid (e.g., DNA, mRNA, non-coding RNA, and the like).

One illustrative, but non-limiting embodiment of a lysis solution well suited for the extraction of either DNA or RNA is shown below in Table 5.

TABLE 5

Illustrative formulation for a lysis solution suited for the extraction of DNA and/or RNA.

| Component | Concentration in Buffer | U/M |
|---|---|---|
| Water, Molecular Biology Grade | n/a | n/a |
| Buffer e.g, Tris, 1M, pH 7.0 | 50 | mM |
| Chaotropic agent e.g, Guanidine Hydrochloride | 4 | M |
| Chelating agent e.g., EDTA | 50 | mM |
| Detergent e.g., Sodium Dodecyl Sulphate (SDS) | 34.7 | mM |
| Second detergent e.g., Tween 20 | 10.0 | %(v/v) |
| Second Chaotrope e.g., Urea | 6 | M |
| Salt e.g., Calcium Chloride | 10 | mM |

This formulation is intended to be illustrative and non-limiting. Using the teachings provided herein, numerous substitutions for any of the components listed in Table 5 will be available to one of skill in the art as will formulations omitting one or more of the listed components.

In certain embodiments polyethylene glycol (e.g., PEG 200) is added to the lysis solution before exposure to the tissue sections or after exposure to the tissue sections. In certain embodiments the lysis solution containing extracted nucleic acid(s), and optionally PEG, can be stored, and/or repeatedly used, e.g., for up to about 4 hrs, or up to about 8 hours, or up to about 1 day, or up to about 2 days, or up to about 3 days, or up to about 4 days, or up to about 1 week, or up to about 2 weeks, or up to about one month, or up to about two months, or up to about 3 months, or up to about 6 months, or up to about one year, or up to about 2 years, or up to about 3 years, or up to about 4 years, or up to about 5 years, or longer.

Heating

In some embodiments, one or more tissue sections are heated in the lysis solution. In this regard, it is noted that where thinner sections are used it is possible and can be desirable to utilize a plurality of sections (e.g., at least 2 sections, or at least 3 sections, or at least 4 sections, or at least 5 sections, or at least 6 sections, or at least 7 sections, or at least 8 sections, or at least 9 sections, or at least 10 sections). Particularly where the section is 5 μm thick or smaller multiple sections can be desirable.

In some embodiments, the sections are heated in the lysis solution at a temperature of about 40° C. up to about 110° C. In some embodiments the sections are heated at a temperature ranging from about 40° C., or from about 45° C., or from about 50° C., or from about 55° C., or from about 60° C., or from about 65° C., or from about 70° C., or from about 74° C. up to about 110° C., or up to about 100° C., or up to about 95° C., or up to about 90° C. In some embodiments, the sections are heated at a temperature ranging from about 80° C. to about 90° C.

In some embodiments, the incubation time ranges from about 10 minutes up to about 4 hours. In some embodiments, the incubation time ranges from about 10 minutes, or from about 15 minutes, or from about 20 minutes, or from about 25 minutes, or from about 30 minutes up to about 24 hours, or up to about 12 hours, or up to about 6 hours, or up to about 4 hours, or up to about 3.5 hours, or up to about 3 hours, or up to about 2.5 hours, or up to about 2 hours, or up to about 1.5 hours, or up to about 1 hour. In some embodiments, the incubation time ranges from about 30 minutes up to about 1 hour.

In one illustrative, but non-limiting, embodiment the one or more sections are incubated (heated) in the lysis solution (e.g., a solution as shown in Table 5) for about 60 minutes at a temperature of about 80° C. In another illustrative, but non-limiting, embodiment the one or more sections are incubated (heated) in the lysis solution (e.g., a solution as shown in Table 5) for about 30 minutes at a temperature of about 90° C.

These heating temperatures and periods are illustrative and not intended to be limiting. Using the teaching provided herein, one of skill may optimized the protocol for a particular sample type at a particular time and temperature.

Nucleic Acid Recovery

After the tissue section(s) are heated in the lysis solution the extracted nucleic acid (e.g., DNA, RNA) is recovered. Numerous methods for DNA and/or RNA recovery are known to those of skill in the art.

In some embodiments, the nucleic acid is precipitated and/or bound to a solid substrate. Precipitation and/or binding to a substrate is readily accomplished by use of an alcohol, for example a lower alcohol (e.g., a $C_1$-$C_6$ alcohol). In some embodiments the alcohol is ethanol or isopropanol. In some embodiment the alcohol is ethanol. It will be recognized that in some embodiments, dry alcohols can be used.

In some embodiments the alcohol is used to simply precipitate the nucleic acid(s). In some embodiments, the alcohol is used to precipitate the nucleic acids in the present of compatible solid phase that results in binding of the nucleic acid to that solid phase.

For example, in some embodiments, the alcohol treatment is performed in the present of a glass or cellulose substrate resulting in the binding of the nuclei acid(s) to that substrate. Remaining contaminants can be washed away while retaining the recovered nucleic acids that are then ready for amplification or other uses.

In some embodiments the solid phase comprises glass, silica, or cellulose. The solid phase can be provided by the walls of a container, as a fiber (e.g., glass fiber), as a membrane (e.g., cellulose membrane), in the form of beads (e.g., microparticles, or nanoparticles, etc.), and the like.

Illustrative, but non-limiting methods for recovery of the nucleic acids are illustrated herein in the Examples. These methods are intended to be illustrative and not limiting. Using the teachings provided herein, numerous recovery methods and extraction protocols will be available to one of skill in the art.

Illustrative Uses of Extracted DNA and/or RNA

The nucleic acids extracted using the methods and reagents described herein are of good quality and can readily be amplified to detect and/or quantify one or more target nucleic acid sequences in the sample. The nucleic acids are particular well suited to PCR amplification reactions including, but not limited to RT-PCR. While in some embodiments, the extracted nucleic acids are used in amplification reactions, other uses are also contemplated. Thus, for example, the extracted nucleic acids (or their amplification product(s)) can be used in various hybridization protocols including, but not limited to nucleic acid based microarrays.

The nucleic extraction methods and reagents described herein are applicable to basic research aimed at the discovery of gene expression profiles relevant to the diagnosis and prognosis of disease. The methods are also applicable to the diagnosis and/or prognosis of disease, the determination particular treatment regiments, monitoring of treatment effectiveness and the like.

The methods described herein simply and efficiently produce extracted nucleic acids well suited for use in RT-PCR systems. While they can be used in any such system, in some embodiments, as illustrated herein in the Examples, the nucleic acids are particularly well suited for use in the GENEXPERT® systems (Cepheid Systems Inc.).

The GENEXPERT® System is a closed, self-contained, fully-integrated and automated platform that represents a paradigm shift in the automation of molecular analysis, producing accurate results in a timely manner with minimal risk of contamination. The GENEXPERT® System combines on-board sample preparation with real-time PCR (polymerase chain reaction) amplification and detection functions for fully integrated and automated nucleic acid analysis. The system is designed to purify, concentrate, detect and identify targeted nucleic acid sequences thereby delivering answers directly from unprocessed samples.

Accordingly, in some embodiments, methods are provided for identification and/or quantitative measurement of a target nucleic acid sequence in a fixed paraffin embedded tissue sample. In some embodiments the methods comprise extracting a nucleic acid (e.g., a DNA, an RNA) from a fixed paraffin embedded biological tissue sample according any of the extraction methods described herein, subjecting the extracted nucleic acid to amplification using a pair of oligonucleotide primers capable of amplifying a region of a target nucleic acid, to obtain an amplified sample; and determining the presence and/or quantity of the target nucleic acid. In some embodiments, the target nucleic acid is a DNA (e.g., a gene). In some embodiments, the target nucleic acid is an RNA (e.g., an mRNA, a non-coding RNA, and the like).

In some embodiments, the nucleic acids extracted using the methods described herein are well suited for use in diagnostic methods, prognostic methods, methods of monitoring treatments (e.g., cancer treatment), and the like. Accordingly, in some illustrative, but non-limiting embodiments, the nucleic acids extracted from fixed paraffin-embedded samples (e.g., from FFPET samples) can be used to identify the presence and/or the expression level of a gene, and/or the mutational status of a gene.

Such methods are particular well suited to identification of the presence, and/or expression level, and/or mutational status of one or more cancer markers. Accordingly, in some embodiments, the nucleic acids extracted using the methods described herein are utilized to detect the presence, and/or copy number, and/or expression level, and/or mutational status of one or more cancer markers. Illustrative, but non-limiting cancer markers are shown in Table 6.

TABLE 6

Illustrative, but non-limiting, cancer markers and associated uses.

| Cancer Marker | Cancer | Uses |
| --- | --- | --- |
| ALK gene rearrangements | Non-small cell lung cancer and anaplastic large cell lymphoma | To help determine treatment and prognosis |

TABLE 6-continued

Illustrative, but non-limiting, cancer markers and associated uses.

| Cancer Marker | Cancer | Uses |
|---|---|---|
| Alpha-fetoprotein (AFP) | Liver cancer and germ cell tumors | To help diagnose liver cancer and follow response to treatment; to assess stage, prognosis, and response to treatment of germ cell tumors |
| Beta-2-microglobulin (B2M) | Multiple myeloma, chronic lymphocytic leukemia, and some lymphomas | To determine prognosis and follow response to treatment |
| Beta-human chorionic gonadotropin (Beta-hCG) | Choriocarcinoma and testicular cancer | To assess stage, prognosis, and response to treatment |
| BCR-ABL fusion gene | Chronic myeloid leukemia | To confirm diagnosis and monitor disease status |
| BRAF mutation V600E | Cutaneous melanoma and colorectal cancer | To predict response to targeted therapies |
| CA15-3/CA27.29 | Breast cancer | To assess whether treatment is working or disease has recurred |
| CA19-9 | Pancreatic cancer, gallbladder cancer, bile duct cancer, and gastric cancer | To assess whether treatment is working |
| CA-125 | Ovarian cancer | To help in diagnosis, assessment of response to treatment, and evaluation of recurrence |
| Calcitonin | Medullary thyroid cancer | To aid in diagnosis, check whether treatment is working, and assess recurrence |
| Carcinoembryonic antigen (CEA) | Colorectal cancer and breast cancer | To check whether colorectal cancer has spread; to look for breast cancer recurrence and assess response to treatment |
| CD20 | Non-Hodgkin lymphoma | To determine whether treatment with a targeted therapy is appropriate |
| Chromogranin A (CgA) | Neuroendocrine tumors | To help in diagnosis, assessment of treatment response, and evaluation of recurrence |
| Chromosomes 3, 7, 17, and 9p21 | Bladder cancer | To help in monitoring for tumor recurrence |
| Cytokeratin fragments 21-1 | Lung cancer | To help in monitoring for recurrence |
| EGFR mutation analysis | Non-small cell lung cancer | To help determine treatment and prognosis |
| Estrogen receptor (ER)/progesterone receptor (PR) | Breast cancer | To determine whether treatment with hormonal therapy (such as tamoxifen) is appropriate |
| Fibrin/fibrinogen | Bladder cancer | To monitor progression and response to treatment |
| HE4 | Ovarian cancer | To assess disease progression and monitor for recurrence |
| HER2/neu | Breast cancer, gastric cancer, and esophageal cancer | To determine whether treatment with trastuzumab is appropriate |
| Immunoglobulins | Multiple myeloma and Waldenström macroglobulinemia | To help diagnose disease, assess response to treatment, and look for recurrence |
| KIT | Gastrointestinal stromal tumor and mucosal melanoma | To help in diagnosing and determining treatment |
| KRAS mutation analysis | Colorectal cancer and non-small cell lung cancer | To determine whether treatment with a particular type of targeted therapy is appropriate |
| Lactate dehydrogenase | Germ cell tumors | To assess stage, prognosis, and response to treatment |
| Nuclear matrix protein 22 | Bladder cancer | To monitor response to treatment |
| Prostate-specific antigen (PSA) | Prostate cancer | To help in diagnosis, assess response to treatment, and look for recurrence |
| Thyroglobulin | Thyroid cancer | To evaluate response to treatment and look for recurrence |
| Urokinase plasminogen activator (uPA) and plasminogen activator inhibitor (PAI-1) | Breast cancer | To determine aggressiveness of cancer and guide treatment |

TABLE 6-continued

Illustrative, but non-limiting, cancer markers and associated uses.

| Cancer Marker | Cancer | Uses |
| --- | --- | --- |
| 5-Protein signature (Oval) | Ovarian cancer | To pre-operatively assess pelvic mass for suspected ovarian cancer |
| 21-Gene signature (Oncotype DX) | Breast cancer | To evaluate risk of recurrence |
| 70-Gene signature (Mammaprint) | Breast cancer | To evaluate risk of recurrence |

In some embodiments, the target nucleic acid comprises a microRNA described in U.S. Patent Publication Nos: 2012/0171686 and 2009/0062135, which are incorporated herein by reference for the target nucleic acid sequences listed therein. In some embodiments the target nucleic acid comprises a nucleic acid marker for the presence and/or severity and/or prognosis of lung cancer. In some embodiments the target nuclei acid comprises a target nucleic acid marker for lung cancer (e.g., non-small cell lung cancer) described in in U.S. Patent Publication No 2010/0233704, which is incorporated herein by reference for the target nucleic acid sequences listed therein. In some embodiments the target nucleic acid comprises a nucleic acid marker for the presence and/or severity and/or prognosis of cervical cancer and/or cervical dysplasia. In some embodiments the target nuclei acid comprises a target nucleic acid marker for cervical dysplasia and/or cervical cancer described in in U.S. Patent Publication No 2010/0240049, which is incorporated herein by reference for the target nucleic acid sequences listed therein.

The foregoing target nucleic acids are illustrative and non-limiting. Using the teaching provided herein, numerous other target nucleic acid sequences will be available to one of skill in the art.

In some, a normal level (a "control") for each target nucleic acid (e.g., RNA) can be determined as an average (or median) level or range that is characteristic of normal cells or other reference material, against which the level measured in the sample can be compared. The determined average (or median) or range of target nucleic acid (e.g., RNA) in normal subjects can be used as a benchmark for detecting above-normal levels of target RNA indicative of a disease state (e.g., the presence of or predilection for a cancer). In some embodiments, normal levels of target nucleic acid can be determined using individual or pooled RNA-containing samples from one or more individuals, such as, in the case of cervical cancer, from patients undergoing hysterectomy for benign gynecologic disease.

In some embodiments, determining a normal level of expression of a target nucleic acid (e.g., RNA) comprises detecting a complex comprising a probe hybridized to a nucleic acid selected from a target RNA, a DNA amplicon of the target RNA, and a complement of the target RNA. That is, in some embodiments, a normal level of expression can be determined by detecting a DNA amplicon of the target RNA, or a complement of the target RNA rather than the target RNA itself. In some embodiments, a normal level of such a complex is determined and used as a control. The normal level of the complex, in some embodiments, correlates to the normal level of the target RNA.

In some embodiments, a control comprises RNA from cells of a single individual, cells known to be healthy from the same subject. In some embodiments, a control comprises RNA from a pool of cells from multiple individuals. In some embodiments, a control is drawn from anatomically and/or cytologically normal areas of the of the individual from whom the test sample was obtained. In some embodiments, a control comprises commercially-available human RNA, such as, for example in the case of cervical cancer, human cervix total RNA (Ambion; AM6992). In some embodiments, a normal level or normal range has already been predetermined prior to testing a sample for an elevated level.

In some embodiments, the normal level of target RNA can be determined from one or more continuous cell lines, typically cell lines previously shown to have expression levels of the at least one target RNA that approximate the level of expression in normal cells.

In some embodiments, a method comprises detecting the level of expression of at least one target RNA. In some embodiments, a method further comprises comparing the level of expression of at least one target RNA to a normal level of expression of the at least one target RNA. In some embodiments, a method further comprises comparing the level of expression of at least one target RNA to a control level of expression of the at least one target RNA. A control level of expression of the at least one target RNA is, in some embodiments, the level of expression of the at least one target RNA in a normal cell. In some such embodiments, a control level may be referred to as a normal level. In some embodiments, a greater level of expression of the at least one target RNA relative to the level of expression of the at least one target RNA in a normal cell indicates cervical dysplasia.

In some embodiments, the level of expression of the at least one target RNA is compared to a reference level of expression, e.g., from a confirmed neoplasia. In some such embodiments, a similar level of expression of the at least one target RNA relative to the reference sample indicates the presence of a neoplasia.

In some embodiments, a level of expression of at least one target RNA that is at least about two-fold greater than a normal level of expression of the respective at least one target RNA indicates the presence of a disease state (e.g., a cancer). In some embodiments, a level of expression of at least one target RNA that is at least about two-fold greater than the level of the respective at least one target RNA in a control sample comprised of normal cells indicates the presence of a cancer. In some embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than the level of expression of the respective at least one target RNA in a control sample comprised of normal cells indicates the presence of a cancer. In some embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than a normal level of expression of the at least one target RNA indicates the presence of a cancer.

In some embodiments, a control level of expression of a target RNA is determined contemporaneously, such as in the same assay or batch of assays, as the level of expression of the target RNA in a sample. In some embodiments, a control level of expression of a target RNA is not determined contemporaneously as the level of expression of the target RNA in a sample. In some such embodiments, the control level of expression has been determined previously.

In some embodiments, the level of expression of a target RNA is not compared to a control level of expression, for example, when it is known that the target RNA is expressed at very low levels, or not at all, in normal cells. In such embodiments, detection of a high level of the target RNA in a sample is indicative of a cancer.

EXAMPLES

The following examples are offered to illustrate, but not to limit the claimed invention.

Example 1

Formalin Fixed Paraffin Embedded Tissue DNA and RNA Extraction for PCR in GeneXpert This example describes the isolation of DNA/RNA from formalin-fixed paraffin embedded (FFPE) samples for PCR-based analysis on the GeneXpert platform. A simple procedure is utilized for extracting genetic material from such samples. In particular the methods described herein are utilized to extract DNA from FFPET tumor tissue samples and the KRAS mutational status of tumor tissue is determined using the extracted DNA in subsequent analysis using the GENEXPERT® cartridge with analysis by the KRAS 2-melt probe assay. In addition, methods described herein are used to extract RNA from FFPET samples using one lysis solution described herein for sample prep and the GeneXpert cartridge to evaluate selected mRNA transcription levels relevant to cancer diagnostics (breast cancer and bladder cancer) by RT-PCR.

DNA was extracted from a formalin-fixed paraffin embedded tissue (FFPET) sample using the lysis solution whose composition is shown in Table 5 (designated as lysis reagent (LR) in this example). Colon cancer tissue samples (10 μm sections) were incubated in 0.75 mL Lysis Reagent (LR) for 30 minutes at 90° C. Then 0.75 ml EtOH was added, the mixture was then vortexed and centrifuged. 1.5 mL of the resulting lysis/EtOH solution were transferred to Chamber 3 of GENEXPERT® Cartridge C. The GeneXpert cartridge was run with the KRAS 2-melt probe assay.

Figure 2A:
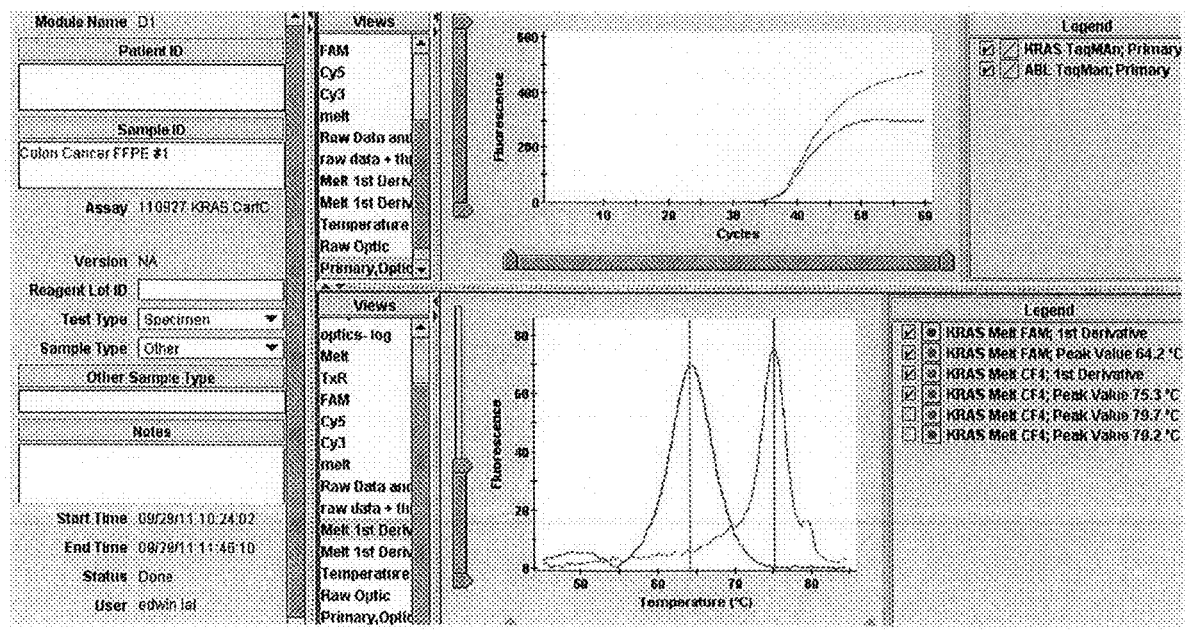
FIGS. 2A and 2B illustrate a KRAS 2-melt probe assay on sample(s) processed using the methods described herein.
Figure 2B:
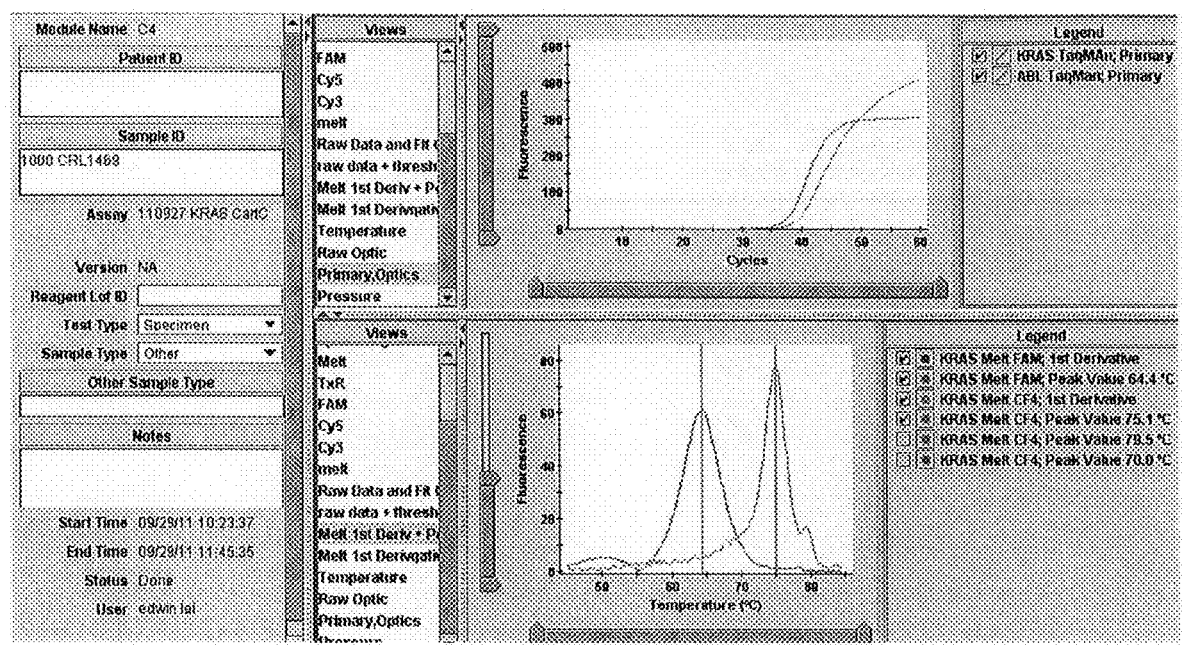

The results of this assay are shown in FIG. 2A. As can be seen therein, a mutation was detected. This mutation was identified as 12ASP from comparison with the melt curve analysis for the various cell lines containing KRAS mutations (reference cell line, CRL-1469) as illustrated in FIG. 2B.

Figure 3:
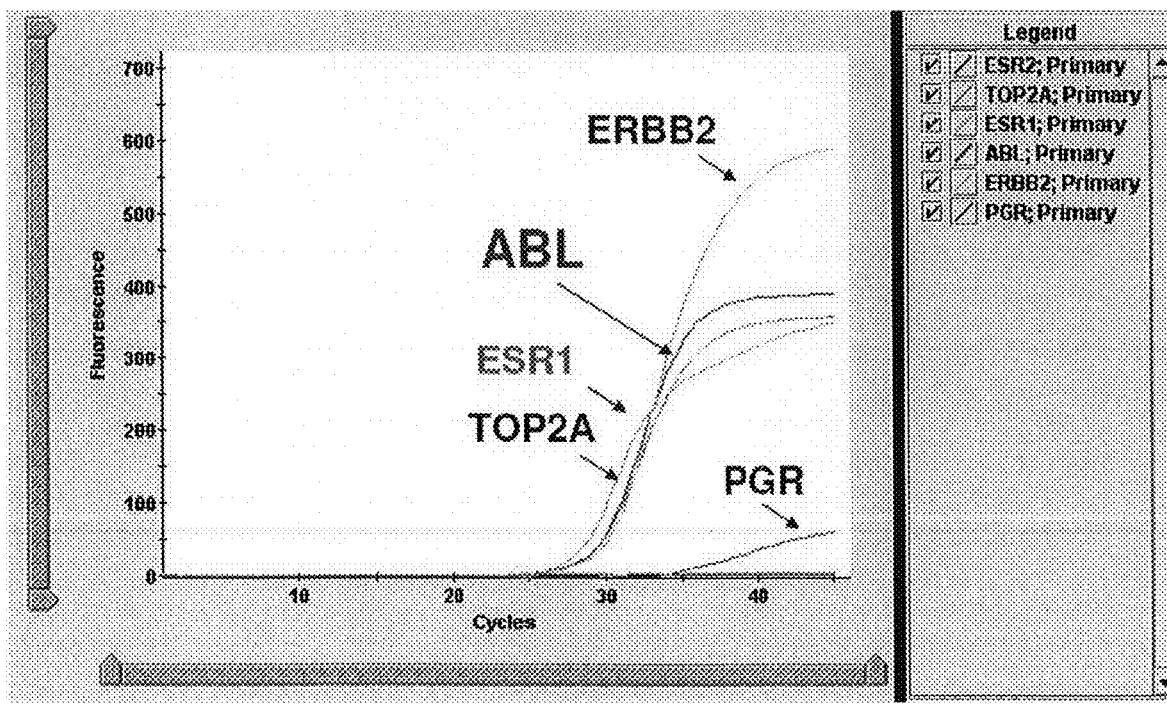
FIG. 3 shows the results of an RT-PCR analysis of a breast cancer FFPET sample processed using the methods described herein.
Figure 4:
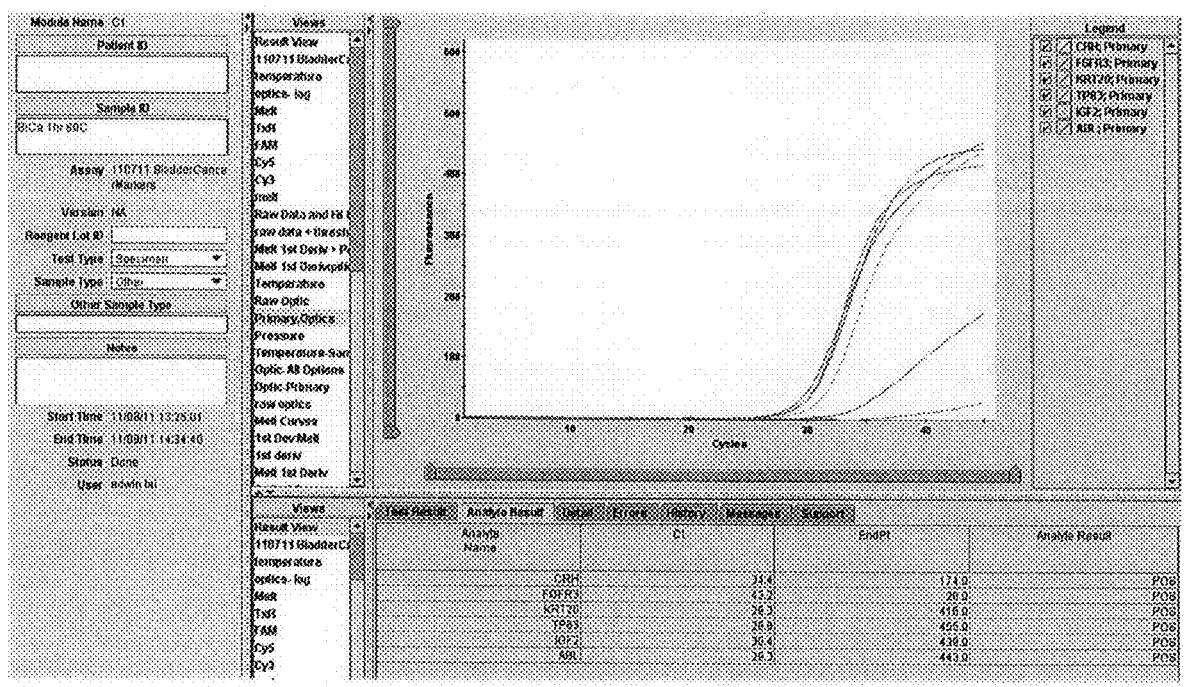
FIG. 4 shows the results of an RT-PCR analysis of a bladder cancer FFPET sample processed using the methods described herein.

RNA was extracted from formalin-fixed paraffin embedded tissue (FFPET) samples using the lysis solution whose composition is shown in Table 5 (designated as lysis reagent (LR) in this example). The isolation protocol is schematically illustrated in FIG. 1. In separate experiments, breast cancer and bladder cancer tissue samples (10 μm sections) were incubated in 0.75 mL Lysis Reagent (LR) for 60 minutes at 80° C. Then 0.75 ml EtOH was added, the mixture vortexed and centrifuged. 1.5 mL of the resulting lysis/EtOH solution were transferred to Chamber 3 of GENEXPERT® Cartridge C for RT-PCR. Markers for breast cancer were clearly identified (see, e.g., FIG. 3) as were markers in the bladder cancer (see, e.g. FIG. 4).

An RNA stability study was performed. Table 7 shows RT-PCR results from bladder cancer FFPET and normal adjacent tissue (NAT). Incubation in lysis reagent (LR) was performed at 60° C. overnight or at 80° C. for 1 hour.

TABLE 7

RNA stability and temperature/time comparison. RT-PCR results from bladder cancer FFPET and normal adjacent tissue (NAT)

| | CRH | | FGFR3 | | KRT20 | | TP63 | | IGF2 | | ABIL, | | Pressure (PSI) | |
| --- | --- | --- | --- | --- | --- | --- | --- | --- | --- | --- | --- | --- | --- | --- |
| | Ct | End Pt | Ct | End Pt | Ct | End Pt | Ct | End Pt | Ct | End Pt | Ct | End Pt | Max | Min |
| BICa 60° C. overnight | 36.6 | 155 | 45 | −4 | 31.4 | 364 | 31.1 | 385 | 30.6 | 483 | 30.5 | 386 | 25.3 | 10 |
| BICa 80° C. 1 hr | 34.4 | 174 | 43.2 | 28 | 29.3 | 416 | 28.8 | 455 | 30.4 | 439 | 29.3 | 443 | 30.1 | −11.3 |
| NAT 60° C. overnight | 45 | 5 | 45 | 0 | 45 | 1 | 45 | 5 | 30.8 | 529 | 31.2 | 456 | 24.5 | −13.9 |
| NAT 80° C. 1 hr | 45 | 3 | 45 | −1 | 41.6 | 53 | 38.8 | 141 | 30.6 | 502 | 30.2 | 443 | 29.1 | −10.8 |

In another experiments, results using the lysis reagent (LR) were compared to those obtained using a proteinase K (PK lysis) protocol. In the PK lysis protocol, 10 µm FFPET sections were placed in a deparaffinization solution (n-hexadecane Deparaffinization Solution, Qiagen) for 3 minutes at 56° C. Then the samples were incubated in a PK lysis solution comprising 100 mm NaCl, 5 mM EDTA, 0.5% SDS, pH 7.0 plus Roche proteinase k, for 15 minutes at 56° C. followed by 15 minutes at 80° C. The results are shown in Table 8.

TABLE 8

RT-PCR results from comparison of BCR-ABL Lysis and with Proteinase K on FFPET samples.

| Assay | Sample ID | ESR2 Ct | ESR2 End Pt | TOP2A Ct | TOP2A End Pt | ESR1 Ct | ESR1 End Pt | ABl Ct | ABl End Pt |
|---|---|---|---|---|---|---|---|---|---|
| 111121 breast cancer 6plex_1 | LR lysis FFPET 2 | 0 | 1 | 33.8 | 250 | 0 | −1 | 29.5 | 333 |
| 111121 breast cancer 6plex_1 | LR lysis FFPET | 0 | 2 | 33.2 | 309 | 0 | 0 | 29.3 | 415 |
| 120113 FFPE BC ROBjc_air | PK lysis FFPET2 | 0 | 1 | 30.4 | 266 | 34.4 | 23 | 28.7 | 354 |
| 120113 FFPE BC ROBjc_air | PK lysis FFPET | 0 | 0 | 32.1 | 240 | 0 | 16 | 29.2 | 319 |

| Assay | Sample | ERBB2 Ct | ERBB2 End Pt | PGR Ct | PGR End Pt | Max Pressure PSI | Min Pressure PSI |
|---|---|---|---|---|---|---|---|
| 111121 breast cancer 6plex_1 | LR lysis FFPET 2 | 32.7 | 511 | 0 | −17 | 728 | −11.1 |
| 111121 breast cancer 6plex_1 | LR lysis FFPET | 32.7 | 603 | 0 | −27 | 505 | −19.3 |
| 120113 FFPE BC ROBjc_air | PK lysis FFPET2 | 31.1 | 518 | 38.3 | 31 | 51.2 | −19.7 |
| 120113 FFPE BC ROBjc_air | PK lysis FFPET | 31.8 | 449 | 0 | 14 | 54.9 | −12.3 |

Example 2

CT/NG Lysis Reagent Compared to BCR-ABL Reagent on Cells

The lysing/deparifinization/delinking steps were studied by testing the BCR-ABL lysis reagent, against the CT/NG Lysis reagent. Two separate experiments were performed that indicate in certain embodiments, a CT/NG lysis reagent (e.g., at pH ~3.5) can yield better results.

In the first experiment (121017), BCR-ABL lysis reagent was tested against 3 different versions of the CT/NG lysis reagent. One CT/NG lysis reagent has a pH of 3.50; another version had a pH of 5.09, and still another version had a pH of about 7.20. One mL aliquots of all four lysis reagent were compared by spiking in equal volumes of UACC 812 cells (10,000 cells per spike); heating for 1 hour at 80° C., adding equal volumes of ethanol and then testing them in 6-plex cartridges. The table below shows one of the cycle threshold results:

TABLE 9

Effect of lysis solution on cycle threshold (Ct).

| | Cycle Threshold | | | | | |
|---|---|---|---|---|---|---|
| sample ID (N = 2) | CF1 TOP2A | FAM MKi67 | CF3 ER1 v2 | CF4 ABL | CF5 HER2 | CF6 PRG v2 |
| BCR-ABL, pH 7.0 | 33.4 | 34.0 | 33.3 | 32.7 | 31.7 | 41.0 |
| CT-NG, pH 3.50 | 28.8 | 30.3 | 28.7 | 31.4 | 26.7 | 35.1 |
| CT-NG, pH 5.09 | 29.3 | 30.6 | 29.0 | 31.7 | 26.7 | 37.0 |
| CT-NG, pH 7.64* | 30.4 | 31.6 | 31.0 | 32.2 | 29.2 | 38.1 |

Is was a surprising result that the CT-NG lysis samples at pH 3.50 (see, Table 14, below) gave much earlier Ct results, sometimes better than 4 Cts, as compared to the BCR-ABL lysis (see Table 11, below) samples. Since all lysis samples received the same number of UACC812 cells, the earlier Ct values may indicate better RNA template recovery (i.e., template quality) by using the CT-NG lysis reagent.

In a second experiment (121018), BCR-ABL lysis reagent (see Table 11, below) was tested against CT/NG lysis reagent at 3.50 (see, Table 14, below) and 5.09 (see, Table 12, below) and using three other cell lines. The same set-up and testing was performed as the first experiment. These results are shown in Table 10 below.

TABLE 10

Cycle threshold (Ct) as a function of cell line and lysis reagent.

| Cell line | Lysis Reagent (N = 2) | CF1 TOP2A | FAM MKi67 | CF3 ER1 v2 | CF4 ABL | CF5 HER2 | CF6 PRG v2 |
|---|---|---|---|---|---|---|---|
| MCF-7 ER+/ PR+/ HER2− | BCR-ABL pH 7.0 | 31.8 | 31.3 | 29.7 | 29.4 | 34.2 | 34.8 |
| | CT-NG pH 3.50 | 27.6 | 28.2 | 25.3 | 28.4 | 29.2 | 31.0 |
| | CT-NG pH 5.09 | 28.8 | 29.0 | 26.3 | 29.0 | 30.2 | 32.2 |
| SKBR-3 ER−/ PR−/ HER2+ | BCR-ABL pH 7.0 | 30.1 | 30.8 | 41.2* | 29.7 | 28.2 | 45.0 |
| | CT-NG pH 3.50 | 24.5 | 26.3 | 40.3* | 27.8 | 22.7 | 45.0 |
| | CT-NG pH 5.09 | 26.3 | 28.1 | 40.5* | 29.3 | 24.0 | 45.0 |
| MDAMB 361 ER+/ PR+/ HER2+ | BCR-ABL pH 7.0 | 38.7 | 45.0 | 32.5 | 28.8 | 32.5 | 44.1 |
| | CT-NG pH 3.50 | 34.2 | 33.9 | 29.1 | 33.3 | 29.6 | 38.4 |
| | CT-NG pH 5.09 | 34.7 | 35.3 | 29.7 | 32.2 | 29.9 | 40.1 |

As in the first experiment, the CT/NG lysis reagent (pH 3.50) gave earlier Ct values when compared against the BCR-ABL lysis reagent.

Materials and Methods

The goal of this experiment was to test for lysis reagents for off-board lyses. The reagents were tested with the GENEXPERT® 6-plex cartridge.

Test Samples

Test samples included UACC 812 cells ($3.3 \times 10^6$ cells/mL), used at ~5000 cells per cartridge. UACC 812 is ER+/PR+/HER2+.

Cartridge Preparation

Revised GENEXPERT® C cartridges were used for the assay. A funnel was inserted into chamber 3 for each cartridge. The Flu combo bead and a 6-plex TSR bead was added to chamber 11. A small retain ball and a large retain ball were also dropped into chamber 11 and pushed down slightly. Dry ROBAL lids were welded onto the cartridges using Dukane welders. Cartridges were packed in fillpack boxes with desiccant pouches, then sealed in re-sealable foil pouches.

Sample Preparation

UACC 812 cells, stored at −80° C., were quickly thawed at room temperature. 1.2 mL of a designated lysis reagent was added to a labeled 1.5 mL tube. 3.03 µL (10,000 cells) was added to each tube. The tubes were vortexed for at least 5 seconds. The tubes were incubated at 80° C. for 30 minutes. The tubes were vortexed for at least 5 seconds to mix. The tubes were incubated at 80° C. for 30 minutes. The contents of each tube was transferred to a labeled 5 mL tube. Approximately 1.2 mL of 100% ethanol was added to each 5 mL tube. The tubes were vortexed for at least 5 seconds. 600 µL of BCR-ABL Rinse Buffer was added to chamber 2 in all cartridges. 2000 µL of BCR-ABL Elution Buffer was added to chamber 5 in all cartridges. 1000 µL aliquots were transferred to chamber 3 in labeled GX cartridge (N=2). All cartridges were tested using the 120628 Breast Cancer 6-plex ADF.

Device Setup

Four lysis reagents were prepared: 1) BCR-ABL lysis reagent at pH 7.00 (see, Table 11 below), 2) CT/NG lysis reagent at pH 5.09 (see, Table 12 below), 3) CT/NG lysis reagent at pH 7.6 (see, Table 13 below), and 4) CT/NG lysis reagent at pH 3.5 (see, Table 14 below).

TABLE 11

BCR-ABL lysis reagent.
BCR-ABL Lysis Reagent

| | |
|---|---|
| Guanidine HCl | 4M |
| Urea | 6M |
| EDTA | 50 mM |
| SDS | 34.7 mM |
| Tris-HCL, pH 6.4 | 50 mM |
| Tween-20 | 10% (v/v) |
| CaCl2 | 10 mM |
| final pH | 7.00 |

TABLE 12

CT/NG Lysis reagent pH 5.09.
CT/NG Lysis Rgt (PN 500-1511, lot DL-1)

| | |
|---|---|
| Guanidine Thiocyanate | 4.5M |
| N-acetyl-L-cysteine | 1% |
| NaCitrate | 25 mM |
| N-Lauroylsarcosine | 0.40% |
| Trizma base | 50 mM |
| final pH | 5.09 |

TABLE 13

CT/NG Lysis reagent pH 7.6.
modified CT/NG Lysis Reagent

| | |
|---|---|
| Guanidine Thiocyanate | 4.5M |
| N-acetyl-L-cysteine | 1% |
| NaCitrate | 25 mM |
| N-Lauroylsarcosine | 0.40% |
| HEPES salt (MW 260.3) | 92 mM |
| HEPES acid (MW 238.3) | 8 mM |
| final pH | ~7.64 |

TABLE 14

CT/NG Lysis reagent pH 3.5.
CT/NG Lysis Reagent (PN 500-1511)

| | |
|---|---|
| Guanidine Thiocyanate | 4.5M |
| N-acetyl-L-cysteine | 1% |
| NaCitrate | 25 mM |
| N-Lauroylsarcosine | 0.40% |
| final pH | ~3.56 |

A GENEXPERT® device was setup as described above and the setup details are summarized in Table 15.

TABLE 15

GENEXPERT ® device setup.

| | | | | |
|---|---|---|---|---|
| revised cart C | 700-3284 | 050412A | N/a | N/a |
| funnel | 300-3463 | 10051811A | chamber 3 | 1 |

TABLE 15-continued

| GENEXPERT ® device setup. | | | | | |
|---|---|---|---|---|---|
| Breast Cancer 6-plex TSR bead | N/a | 120827KH | chamber 11 | 1 | bead |
| Flu A/B combo bead | 500-1453 | 031 | chamber 11 | 1 | bead |
| small retain balls | 300-6099 | 30454435-01 | chamber 11 | 1 | ball |
| large retain balls | 500-0037 | 30456504-03 | chamber 11 | 1 | ball |
| BCR-ABL rinse buffer (Reuel's) | 500-0539 | 111215RBV | chamber 2 | 600 | uL |
| BCR-ABL elution buffer, pH 8.53 | 500-1131 | 120524KH | chamber 5 | 2000 | uL |
| BCR-ABL Lysis buffer (Promega) | MC501V | 29893620 | off board | 1.2 | mL |
| CT-NG Lysis Reagent, pH 3.50 | 500-1511 | DL-5 | off board | 1.2 | mL |
| CT-NG Lysis Reagent, pH 5.09 | 500-1511 | DL-1 | off board | 1.2 | mL |
| CT-NG Lysis Reagent, pH 7.64 | N/a | N/a | off board | 1.2 | mL |
| Ethanol (Sigma-Aldrich) | 459844-1L | SHBC1268V | N/a | 1.2 | mL |

The GENEXPERT® device was operated according to the command sequence shown in Table

TABLE 16

Command sequence for 120828 Breast Cancer 6-plex.
Command Sequence

1. Log Pressure Log Pressure at 500 ms interval.;
2. Pressure Values Min Pressure: −130; Max Pressure: 130; ;
3. Aspirate From Elution; 600 uL @ 50 uL/sec; Direct Path;
4. Dispense To Waste2; 600 uL @ 100 uL/sec; Direct Path;
5. Start Repeat 3 time(s);
6. Aspirate From sample + ethanol; 360 uL @ 50 uL/sec; Direct Path;
7. Dispense To Waste; 360 uL @ 5 uL/sec; Filter Path;
8. Wait 1.0 second(s);
9. End Repeat
10. Aspirate Air From Air1; 100 uL @ 50 uL/sec; Direct Path;
11. Dispense Air To Waste; 100 uL @ 50 uL/sec; Filter Path;
12. Wait 5.0 second(s);
13. Aspirate From Waste2; 500 uL @ 50 uL/sec; Direct Path;
14. Wait 1.0 second(s);
15. Dispense To Waste; 500 uL @ 100 uL/sec; Direct Path;
16. Wait 1.0 second(s);
17. Aspirate From Rinse; 500 uL @ 50 uL/sec; Direct Path;
18. Dispense To Waste; 450 uL @ 10 uL/sec; Filter Path;
19. Wait 1.0 second(s);
20. Dispense To Waste; 50 uL @ 20 uL/sec; Direct Path;
21. Aspirate From Elution; 600 uL @ 50 uL/sec; Direct Path;
22. Wait 30.0 second(s);
23. Dispense To Waste; 300 uL @ 50 uL/sec; Direct Path;
24. Dispense To Chamber 4; 300 uL @ 50 uL/sec; Direct Path;
25. Aspirate From Elution; 120 uL @ 20 uL/sec; Direct Path;
26. Wait 1.0 second(s);
27. Dispense To Waste2; 20 uL @ 5 uL/sec; Filter Path;

TABLE 16-continued

Command sequence for 120828 Breast Cancer 6-plex.
Command Sequence

28. Wait 5.0 second(s);
29. Dispense To RT PCR Beads; 40 uL @ 5 uL/sec; Filter Path;
30. Wait 10.0 second(s);
31. Dispense To RT PCR Beads; 40 uL @ 10 uL/sec; Filter Path;
32. Wait 5.0 second(s);
33. Dispense To Waste2; 20 uL @ 10 uL/sec; Direct Path;
34. Wait 1.0 second(s);
35. Aspirate Air From Air2; 30 uL @ 10 uL/sec; Direct Path;
36. Dispense Air To Waste; 10 uL @ 5 uL/sec; Direct Path;
37. Wait 5.0 second(s);
38. Dispense Air To Chamber 4; 20 uL @ 10 uL/sec; Filter Path;
39. Wait 5.0 second(s);
40. Toggle To RT PCR Beads; 5x Asp: 65@10 Disp: 65@10; Direct Path;
41. Wait 10.0 second(s);
42. Aspirate From RT PCR Beads; 75 uL @10 uL/sec; Direct Path;
43. Wait 1.0 second(s);
44. Dispense To MM; 75 uL @ 10 uL/sec; Direct Path;
45. Wait 1.0 second(s);
46. Aspirate Air From Air2; 40 uL @ 40 uL/sec; Direct Path;
47. Aspirate Into Tube; 70 uL @ 20 uL/sec; Direct Path;
48. Wait 3.0 second(s);
49. Pressurize Tube 40 uL @ 40 uL/sec; Block Tube Ports After Pressurization;
50. Log Pressure Off
51. Protocol 1: Hold; 2: Hold; ;
52. Protocol 1: Probe Check; 2: 3-Temperature Cycle;
53. Depressurize Tube 40 uL @ 40 uL/sec; Filter Path;

Results of lysis reagent testing (cycle threshold (Ct) and endpoint fluorescence (EPF) are shown in Table 17.

TABLE 17

Cycle threshold (Ct) and endpoint fluorescence.

| | Cycle Threshold | | | | | | | |
|---|---|---|---|---|---|---|---|---|
| sample ID | CF1 TOP2A | FAM MKi67 | CF3 ER1 v2 | CF4 ABL | CF5 HER2 | CF6 PRG v2 | Max press | Min press |
| BCR-ABL, 01 | 33.4 | 34.2 | 33.1 | 32.6 | 31.9 | 42.4 | 18 | −12 |
| BCR-ABL, 02 | 33.4 | 33.8 | 33.5 | 32.7 | 31.4 | 39.6 | 25 | −13 |
| mean | 33.4 | 34.0 | 33.3 | 32.7 | 31.7 | 41.0 | 22 | −12 |
| CT-NG, pH 3.50, 01 | 28.5 | 29.9 | 28.2 | 31.0 | 26.2 | 34.7 | 21 | −11 |
| CT-NG, pH 3.50, 02 | 29.1 | 30.6 | 29.1 | 31.7 | 27.2 | 35.4 | 23 | −10 |
| mean | 28.8 | 30.3 | 28.7 | 31.4 | 26.7 | 35.1 | 22 | −10 |
| CT-NG, pH 5.09, 01 | 29.4 | 30.6 | 29.1 | 31.8 | 26.8 | 37.3 | 21 | −13 |
| CT-NG, pH 5.09, 02 | 29.1 | 30.5 | 28.9 | 31.5 | 26.6 | 36.7 | 19 | −7 |

TABLE 17-continued

Cycle threshold (Ct) and endpoint fluorescence.

| mean | 29.3 | 30.6 | 29.0 | 31.7 | 26.7 | 37.0 | 20 | −10 |
|---|---|---|---|---|---|---|---|---|
| CT-NG, pH 7.64, 01 | 0.0* | 0.0* | 0.0* | 0.0* | 0.0* | 0.0* | 0.0* | 0.0* |
| CT-NG, pH 7.64, 02 | 30.4 | 31.6 | 31.0 | 32.2 | 29.2 | 38.1 | 17 | −11 |

| End Point Fluorescence | | | | | | | | |
|---|---|---|---|---|---|---|---|---|
| BCR-ABL, 01 | 284 | 82 | 384 | 103 | 320 | 52 | | |
| BCR-ABL, 02 | 271 | 75 | 289 | 119 | 283 | 104 | | |
| mean | 278 | 79 | 337 | 111 | 302 | 78 | | |
| CT-NG, pH 3.50, 01 | 265 | 307 | 595 | 244 | 370 | 186 | | |
| CT-NG, pH 3.50, 02 | 280 | 274 | 542 | 230 | 329 | 178 | | |
| mean | 273 | 291 | 569 | 237 | 350 | 182 | | |
| CT-NG, pH 5.09, 01 | 260 | 236 | 522 | 213 | 405 | 148 | | |
| CT-NG, pH 5.09, 02 | 285 | 244 | 561 | 230 | 406 | 168 | | |
| mean | 273 | 240 | 542 | 222 | 406 | 158 | | |
| CT-NG, pH 7.64, 01 | 0.0* | 0.0* | 0.0* | 0.0* | 0.0* | 0.0* | | |
| CT-NG, pH 7.64, 02 | 306 | 215 | 509 | 206 | 401 | 116 | | |

*Error 2037: The cartridge integrity test failed at valve position 0. The pressure change of 0.6 PSI did not exceed the requirement of 4.0 PSI. The pressure increased from 1.3 PSI to 1.9 PSI during the test.

Example 3

CT/NG Lysis Reagent Compared to BCR-ABL Reagent on FFPE Samples

Six formalin fixed paraffin embedded (FFPE) tissue scrolls were tested over 4 time points (0 hr, 4 hr, day 3 and day 5) with the Cepheid Breast Cancer Stratifier assay. The six scrolls came from one Cureline sample (#10142) and happened to be in sequential order (scroll #11 thru 16).

Figure 5:
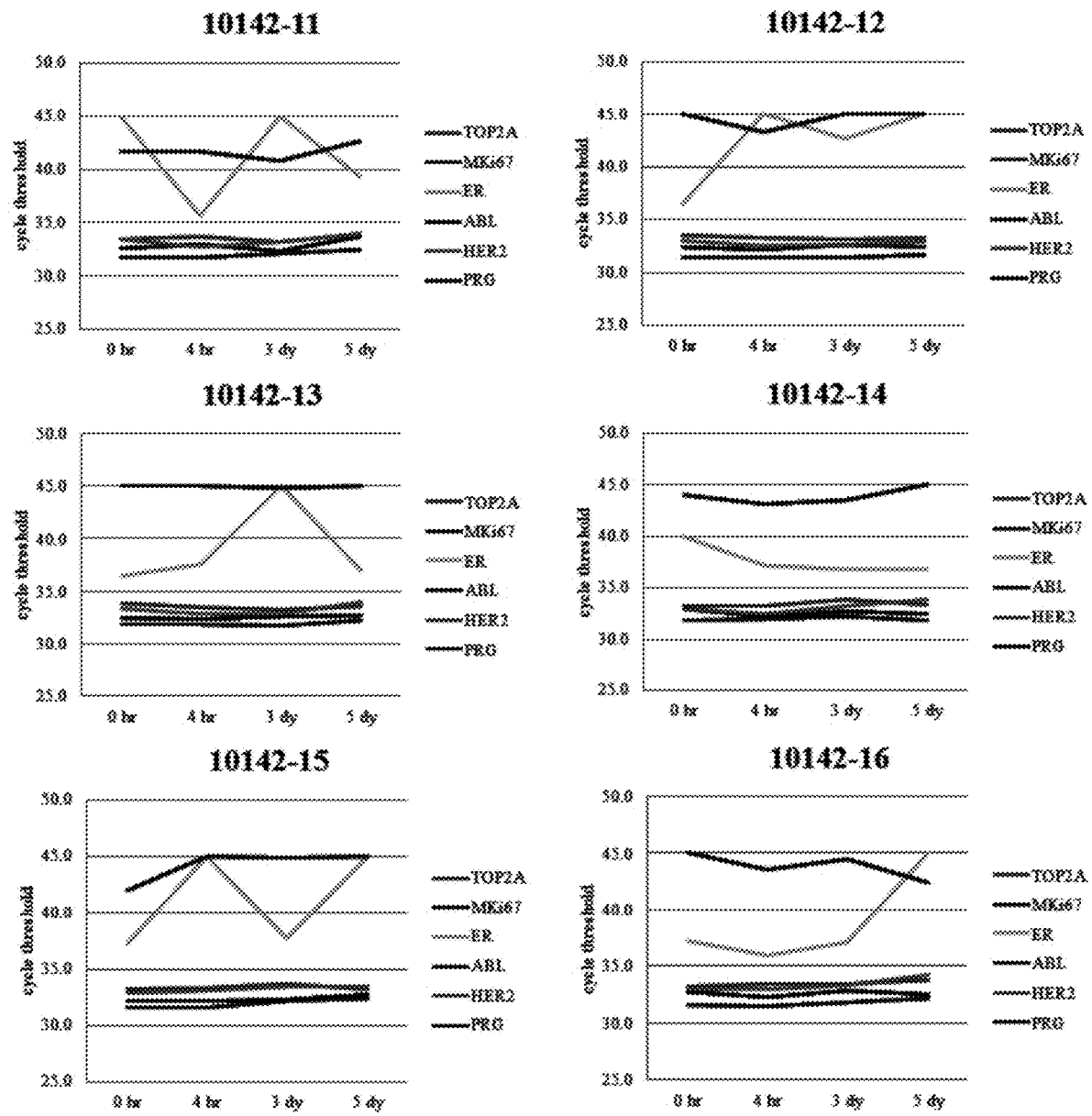
FIG. 5 shows the sample stability over a period of 4 hrs, 3 days, and 5 days for different samples processed using the methods and lysis solutions described herein.

As shown in FIG. 5, and Table 18, below, it was surprisingly discovered that the Ct values for TOP2a, MKi67, HER2 and ABL, were highly consistent across the six scrolls. The base sample (#10142) apparently had little ER and PR signal so those particular Ct values tended to "jump" around.

While the samples were in our CT/NG lysis reagent with PEG 200, they gave consistent results across time (0 hr, 4 hr, day 3, and day 5) meaning the samples were stable in this condition and it was possible to measure multiple pulls from the original lysed scroll to perform either a repeat test (if needed) or reflex cartridge test(s).

TABLE 18

Cycle threshold (Ct) and endpoint fluorescence.

| Sample ID (N = 4 time points) | CF1 TOP2A | FAM MKi67 | CF3 ER1 v2 | CF4 ABL | CF5 HER2 | CF6 PRG v2 |
|---|---|---|---|---|---|---|
| Cycle Threshold | | | | | | |
| 10142-11 | 33.6 | 32.1 | 41.2 | 32.9 | 33.3 | 41.7 |
| 10142-12 | 33.3 | 31.5 | 42.3 | 32.4 | 32.8 | 44.6 |
| 10142-13 | 33.5 | 31.9 | 39.0 | 32.5 | 33.3 | 45.0 |
| 10142-14 | 33.4 | 32.0 | 37.7 | 32.6 | 33.2 | 43.9 |
| 10142-15 | 33.4 | 32.0 | 41.3 | 32.4 | 33.2 | 44.2 |
| 10142-16 | 33.4 | 31.7 | 38.8 | 32.6 | 33.4 | 43.9 |

TABLE 18-continued

Cycle threshold (Ct) and endpoint fluorescence.

| Sample ID (N = 4 time points) | CF1 TOP2A | FAM MKi67 | CF3 ER1 v2 | CF4 ABL | CF5 HER2 | CF6 PRG v2 |
|---|---|---|---|---|---|---|
| End Point Fluorescence | | | | | | |
| 10142-11 | 328 | 166 | 55 | 138 | 224 | 51 |
| 10142-12 | 302 | 184 | 45 | 140 | 227 | 6 |
| 10142-13 | 314 | 180 | 81 | 146 | 211 | 11 |
| 10142-14 | 339 | 188 | 90 | 151 | 225 | 24 |
| 10142-15 | 304 | 157 | 43 | 155 | 199 | 18 |
| 10142-16 | 326 | 211 | 93 | 149 | 221 | 28 |

Materials and Methods

Sample Preparation

Test samples. Six formalin fixed paraffin embedded (FFPE) tissue scrolls were tested over 4 time points (0 hr, 4 hr, day 3 and day 5) with the Cepheid Breast Cancer Stratifier assay. The six scrolls came from one Cureline sample (#10142). FFPE scrolls were sliced and placed in individually labeled 1.5 mL tubes and stored at room temperature.

1.2 mL of CT-NG lysis reagent (Table 14, supra, pH ~3.56) was added to each tube. The tubes were vortexed for at least 5 seconds. The tubes were incubated at 80° C. for 30 minutes. The tubes were vortexed for at least 5 seconds to mix. The tubes were incubated at 80° C. for 30 minutes. The contents of each tube was transferred to a labeled 5 mL tube. Approximately 1.2 mL of PEG 200 was added to each 5 mL tube. The tubes were vortexed for at least 5 seconds. 600 μL of BCR-ABL Rinse Buffer was added to chamber 2 in all cartridges. 2000 μL of BCR-ABL Elution Buffer was added to chamber 5 in all cartridges. A single 500 μL aliquot was transferred to chamber 3 in labeled GX cartridges. Additional 500 μL aliquots from each scroll sample was tested after 4 hours, 3 days and 5 days.

All lysed samples (with PEG 200) were stored at room temperature. All cartridges were tested using the 130107 Stratifier, 0.5 mL ADF as described below.

Cartridge Preparation

Revised GENEXPERT® C cartridges were used for the assay. A funnel was inserted into chamber 3 for each cartridge. A MLV-RT/Taq combo bead and a 6-plex TSR bead was added to chamber 11. A small retain ball and a large retain ball were also dropped into chamber 11 and pushed down slightly.

Device Setup

A GENEXPERT® device was setup as described above and the setup details are summarized in Table 19.

TABLE 19

GENEXPERT ® device setup.

| component | part number | lot number | location | amt/vol |
|---|---|---|---|---|
| revised cart C | 700-3284 | 050412A | N/a | N/a |
| funnel | 300-3463 | 10051811A | chamber 3 | 1 |
| 6-plex TSR bead | N/a | 121204KH | chamber 11 | 1 bead |
| MLV-RT/Taq combo bead | N/a | 121212KH | chamber 11 | 1 bead |
| small retain balls | 300-6099 | 30454435-01 | chamber 11 | 1 ball |
| large retain balls | 500-0037 | 30456504-03 | chamber 11 | 1 ball |
| BCR-ABL rinse buffer (Reuel's) | 500-0539 | 111215RBV | chamber 2 | 600 uL |
| BCR-ABL elution buffer, pH 8.61 | 500-1131 | | chamber 5 | 2000 uL |
| CT-NG Lysis Reagent, pH 3.56 | 500-1511 | 121214KH | off board | 1.2 mL |
| PEG 200 (Sigma-Aldrich) | P3015 | MKBH6605V | N/a | 1.2 mL |

The GENEXPERT® device was operated according to the command sequence shown in Table 20.

TABLE 20

Command sequence.

1. Log Pressure Log Pressure at 500 ms interval.;
2. Pressure Values Min Pressure: −130; Max Pressure: 130; ;
3. Aspirate From Elution; 600 uL @ 50 uL/sec; Direct Path;
4. Dispense To Waste2; 600 uL @ 100 uL/sec; Direct Path;
5. Start Repeat 2 time(s);
6. Aspirate From sample + ethanol; 250 uL @ 50 uL/sec; Direct Path;
7. Dispense To Waste; 250 uL @ 5 uL/sec; Filter Path;
8. Wait 1.0 second(s);
9. End Repeat
10. Aspirate Air From Air1; 100 uL @50 uL/sec; Direct Path;
11. Dispense Air To Waste; 100 uL @ 50 uL/sec; Filter Path;
12. Wait 5.0 second(s);
13. Aspirate From Waste2; 500 uL @ 50 uL/sec; Direct Path;
14. Wait 1.0 second(s);
15. Dispense To Waste; 500 uL @ 100 uL/sec; Direct Path;
16. Wait 1.0 second(s);
17. Aspirate From Rinse; 500 uL @ 50 uL/sec; Direct Path;
18. Dispense To Waste; 450 uL @ 10 uL/sec; Filter Path;
19. Wait 1.0 second(s);
20. Dispense To Waste; 50 uL @ 20 uL/sec; Direct Path;
21. Aspirate From Elution; 600 uL @ 50 uL/sec; Direct Path;
22. Wait 30.0 second(s);
23. Dispense To Waste; 300 uL @ 50 uL/sec; Direct Path;
24. Dispense To Chamber 4; 300 uL @ 50 uL/sec; Direct Path;
25. Aspirate From Elution; 120 uL @ 20 uL/sec; Direct Path;
26. Wait 1.0 second(s);
27. Dispense To Waste2; 20 uL @ 5 uL/sec; Filter Path;
28. Wait 5.0 second(s);
29. Dispense To RT PCR Beads; 40 uL @ 5 uL/sec; Filter Path;
30. Wait 10.0 second(s);
31. Dispense To RT PCR Beads; 40 uL @ 10 uL/sec; Filter Path;
32. Wait 5.0 second(s);
33. Dispense To Waste2; 20 uL @ 10 uL/sec; Direct Path;
34. Wait 1.0 second(s);
35. Aspirate Air From Air2; 30 uL @ 10 uL/sec; Direct Path;
36. Dispense Air To Waste; 10 uL @ 5 uL/sec; Direct Path;
37. Wait 5.0 second(s);
38. Dispense Air To Chamber 4; 20 uL @ 10 uL/sec; Filter Path;
39. Wait 5.0 second(s);
40. Toggle To RT PCR Beads; 5x Asp: 65@10 Disp: 65@10; Direct Path;

TABLE 20-continued

Command sequence.

41. Wait 10.0 second(s);
42. Aspirate From RT PCR Beads; 75 uL @ 10 uL/sec; Direct Path;
43. Wait 1.0 second(s);
44. Dispense To MM; 75 uL @ 10 uL/sec; Direct Path;
45. Wait 1.0 second(s);
46. Aspirate Air From Air2; 40 uL @ 40 uL/sec; Direct Path;

TABLE 20-continued

Command sequence.

47. Aspirate Into Tube; 70 uL @ 20 uL/sec; Direct Path;
48. Wait 3.0 second(s);
49. Pressurize Tube 40 uL @ 40 uL/sec; Block Tube Ports After Pressurization;
50. Log Pressure Off
51. Protocol 1: Hold; 2: Hold; ;
52. Protocol 1: Probe Check; 2: 3-Temperature Cycle; ;
53. Depressurize Tube 40 uL @ 40 uL/sec; Filter Path;

Example 4

Evaluation of Stability of Extracted Nucleic Acid in CT/NG and BCR-ABL Lysis Solution with PEG 200 or Ethanol The purpose of this experiment was to test DLS FFPE scrolls using PEG 200 or ethanol as binding reagents. Tests were performed at days 0, 3, 7 and 14. Lysed samples were mixed with either ethanol or PEG 200 at room temperature and at −80° C. The −80° C. samples were aliquoted for a one time freeze thaw per test date.

Figure 6:
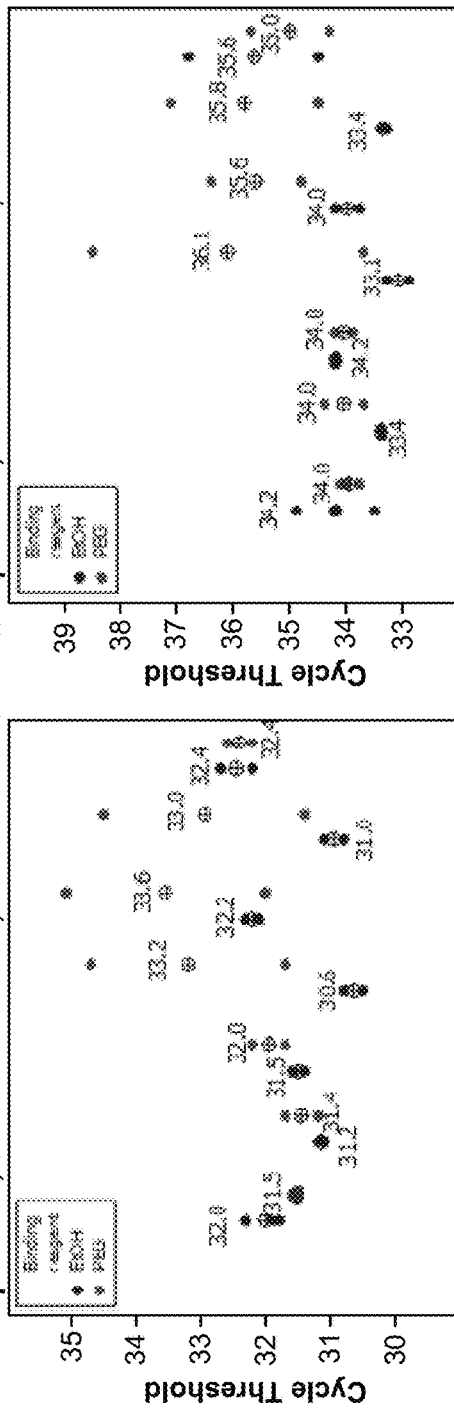
FIG. 6 shows Ct values for each of the samples under all test conditions.
Figure 6:
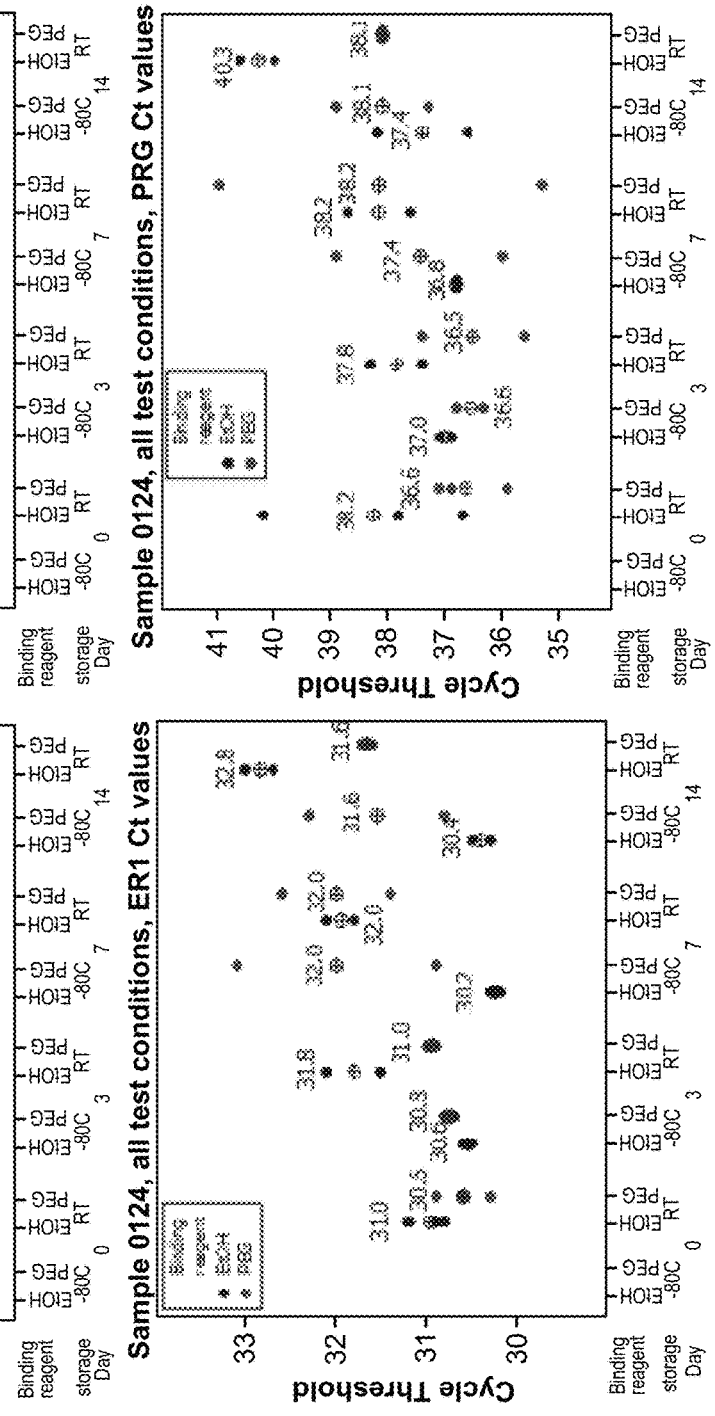
Figure 6:
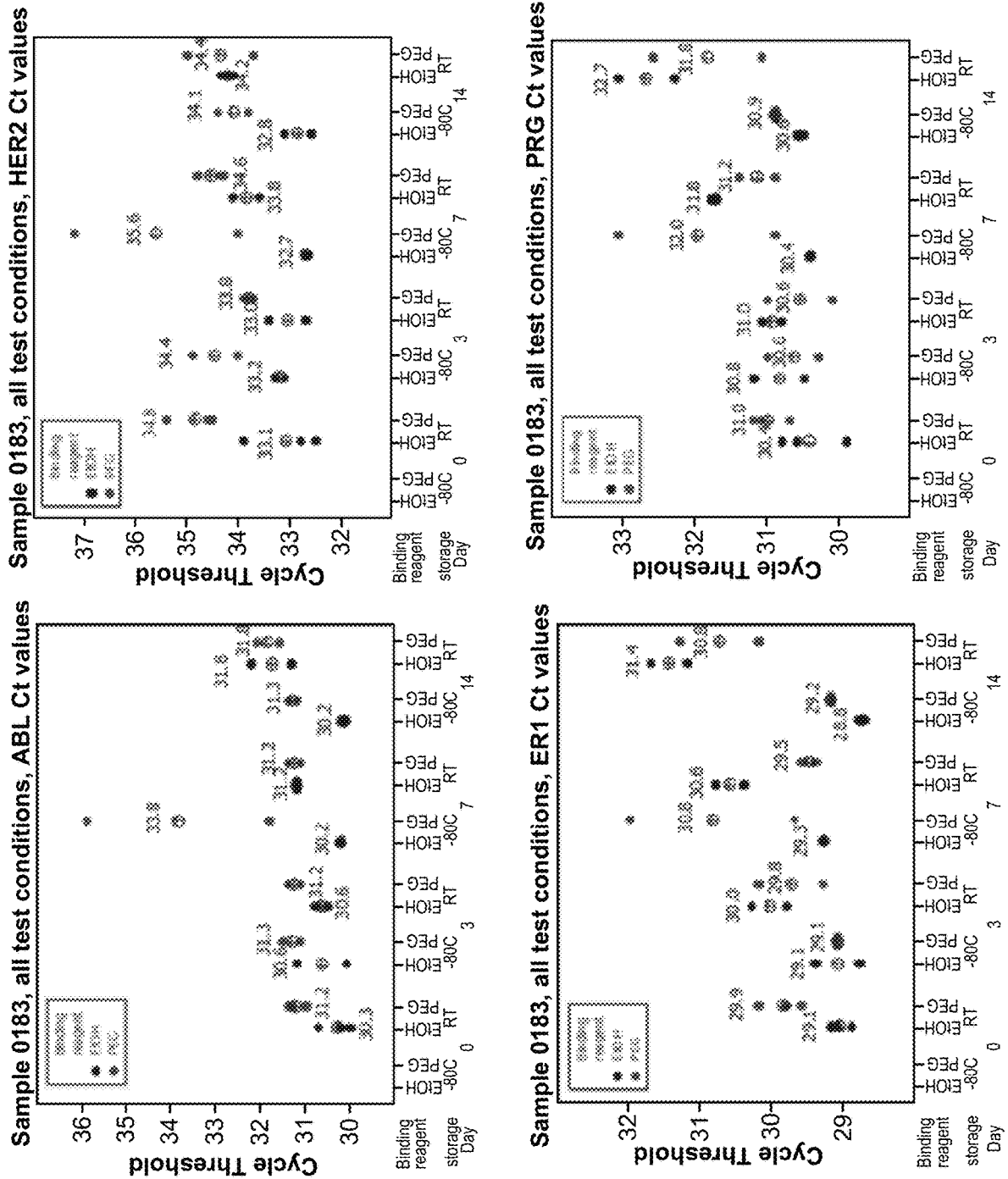
Figure 6:
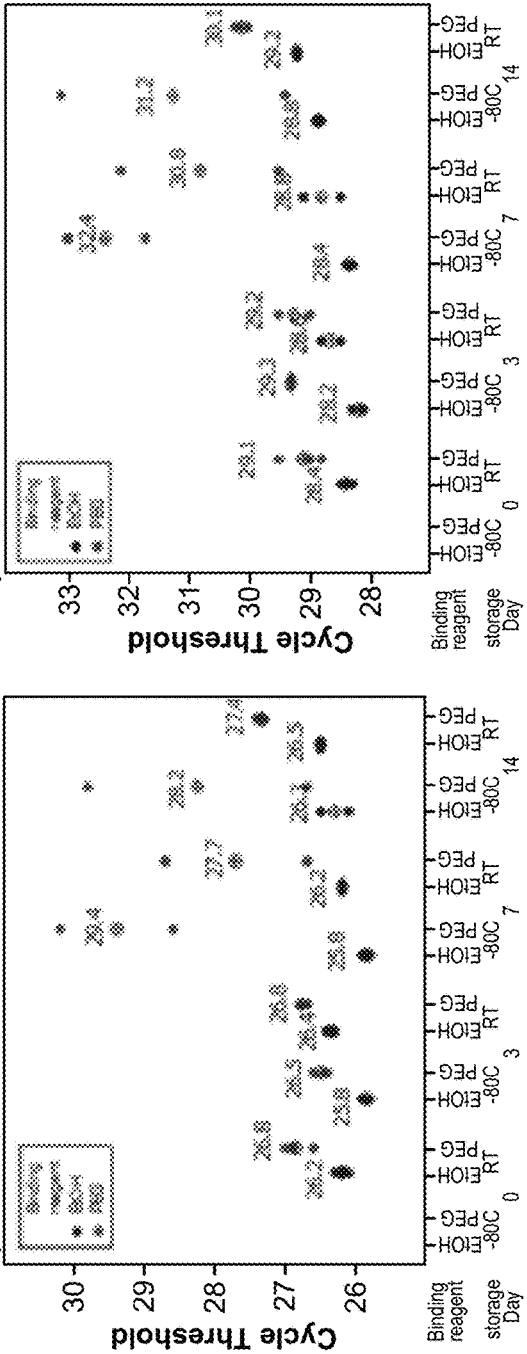
Figure 6:
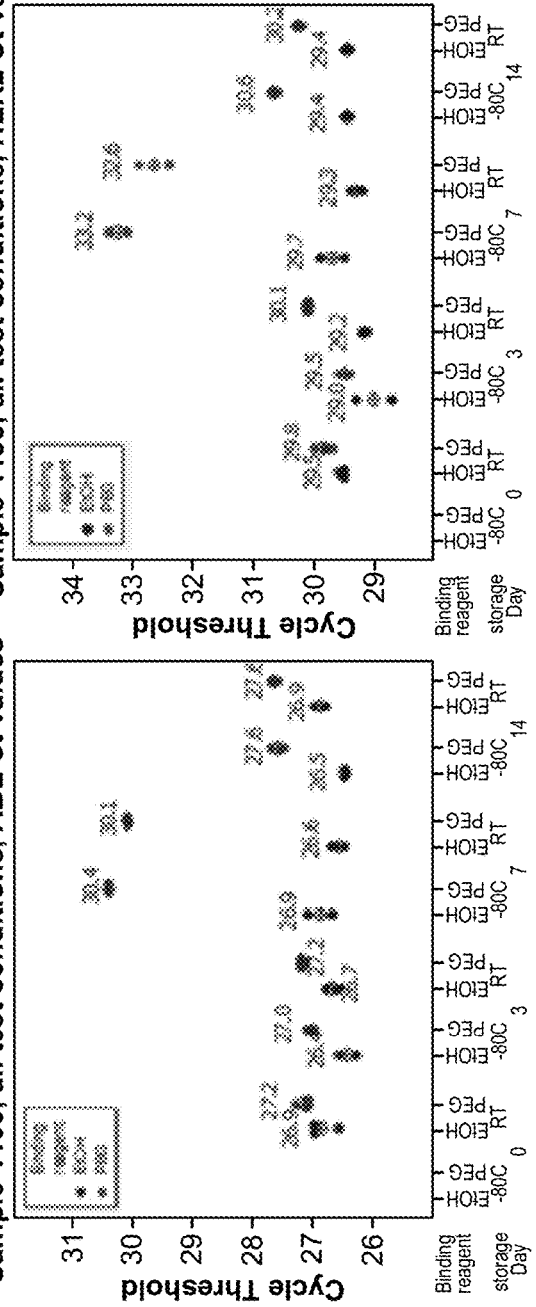
Figure 6:
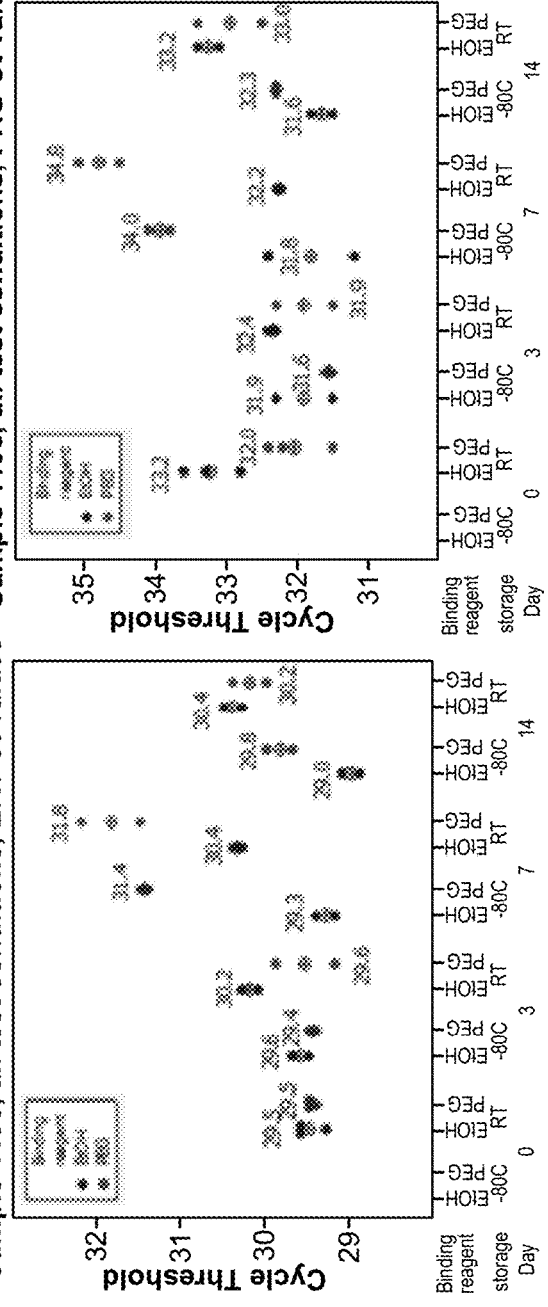

Samples that were stored at −80° C. gave more consistent results versus samples that were stored at room temperature (see, e.g. Tables 21 and 22, and FIG. 6).

Samples that used ethanol as the binding reagent generated typically generated earlier cycle threshold values with less deviations around a mean (see, e.g. Tables 21 and 22, and FIG. 6).

TABLE 21

Cycle threshold (Ct) as a function of storage temperature, storage media, and time of storage.

| Sample | Binding Reagent | Storage temp | Time (Days) | TOP2A | MKi67 | ER1 v2 | ABL | HER2 | PRG v2 |
|---|---|---|---|---|---|---|---|---|---|
| 0124 | EtOH | RT | 0 | 35.6 | 37.5 | 31.0 | 32.0 | 34.2 | 38.2 |
| 0124 | PEG | RT | 0 | 35.5 | 35.3 | 30.6 | 31.5 | 34.0 | 36.6 |
| 0124 | EtOH | −80° C. | 3 | 35.1 | 35.0 | 30.6 | 31.2 | 33.4 | 37.0 |
| 0124 | EtOH | RT | 3 | 35.8 | 35.2 | 31.8 | 31.5 | 34.2 | 37.9 |
| 0124 | PEG | −80° C. | 3 | 35.7 | 34.9 | 30.8 | 31.5 | 34.1 | 36.6 |
| 0124 | PEG | RT | 3 | 35.3 | 34.9 | 31.0 | 32.0 | 34.1 | 36.5 |
| 0124 | EtOH | −80° C. | 7 | 35.2 | 34.3 | 30.3 | 30.7 | 33.1 | 36.8 |
| 0124 | EtOH | RT | 7 | 36.7 | 35.7 | 32.0 | 32.2 | 34.0 | 38.2 |
| 0124 | PEG | −80° C. | 7 | 36.0 | 36.3 | 32.0 | 33.2 | 36.1 | 37.5 |
| 0124 | PEG | RT | 7 | 36.0 | 35.7 | 32.0 | 33.6 | 35.6 | 38.2 |
| 0124 | EtOH | −80° C. | 14 | 34.7 | 34.3 | 30.4 | 31.0 | 33.4 | 37.4 |
| 0124 | EtOH | RT | 14 | 36.7 | 36.3 | 32.9 | 32.5 | 35.7 | 40.3 |
| 0124 | PEG | −80° C. | 14 | 37.2 | 35.6 | 31.6 | 33.0 | 35.8 | 38.1 |
| 0124 | PEG | RT | 14 | 36.6 | 35.7 | 31.7 | 32.4 | 35.0 | 38.1 |
| 0183 | EtOH | RT | 0 | 32.3 | 32.2 | 29.1 | 30.3 | 33.1 | 30.4 |
| 0183 | PEG | RT | 0 | 33.1 | 32.9 | 29.9 | 31.2 | 34.8 | 31.0 |
| 0183 | EtOH | −80° C. | 3 | 32.4 | 32.5 | 29.1 | 30.7 | 33.2 | 30.9 |
| 0183 | EtOH | RT | 3 | 32.7 | 33.0 | 30.1 | 30.7 | 33.1 | 31.0 |
| 0183 | PEG | −80° C. | 3 | 32.6 | 32.5 | 29.1 | 31.3 | 34.5 | 30.7 |
| 0183 | PEG | RT | 3 | 32.7 | 33.0 | 29.8 | 31.3 | 33.8 | 30.6 |
| 0183 | EtOH | −80° C. | 7 | 32.3 | 32.3 | 29.3 | 30.2 | 32.7 | 30.4 |
| 0183 | EtOH | RT | 7 | 32.9 | 33.3 | 30.6 | 31.2 | 33.9 | 31.8 |
| 0183 | PEG | −80° C. | 7 | 34.3 | 33.4 | 30.9 | 33.9 | 35.6 | 32.0 |
| 0183 | PEG | RT | 7 | 33.0 | 32.8 | 29.5 | 31.3 | 34.6 | 31.2 |
| 0183 | EtOH | −80° C. | 14 | 31.8 | 32.1 | 28.8 | 30.2 | 32.9 | 30.6 |
| 0183 | EtOH | RT | 14 | 34.0 | 33.9 | 31.5 | 31.8 | 34.2 | 32.7 |
| 0183 | PEG | −80° C. | 14 | 32.6 | 32.5 | 29.2 | 31.3 | 34.1 | 30.9 |
| 0183 | PEG | RT | 14 | 33.8 | 33.3 | 30.8 | 31.9 | 34.4 | 31.9 |
| 0194 | EtOH | RT | 0 | 25.9 | 25.2 | 27.4 | 26.2 | 28.4 | 35.4 |
| 0194 | PEG | RT | 0 | 26.1 | 25.5 | 27.6 | 26.8 | 29.1 | 34.3 |
| 0194 | EtOH | −80° C. | 3 | 25.3 | 24.9 | 26.9 | 25.9 | 28.2 | 34.1 |
| 0194 | EtOH | RT | 3 | 25.9 | 25.5 | 28.2 | 26.4 | 28.7 | 36.0 |
| 0194 | PEG | −80° C. | 3 | 26.2 | 25.4 | 27.4 | 26.5 | 29.3 | 34.3 |
| 0194 | PEG | RT | 3 | 26.2 | 25.6 | 27.9 | 26.8 | 29.3 | 34.2 |
| 0194 | EtOH | −80° C. | 7 | 25.4 | 25.1 | 27.3 | 25.9 | 28.4 | 34.3 |
| 0194 | EtOH | RT | 7 | 25.5 | 25.4 | 27.7 | 26.2 | 28.8 | 34.8 |
| 0194 | PEG | −80° C. | 7 | 28.3 | 26.9 | 29.6 | 29.4 | 32.4 | 36.1 |
| 0194 | PEG | RT | 7 | 26.9 | 26.0 | 28.3 | 27.7 | 30.8 | 34.9 |
| 0194 | EtOH | −80° C. | 14 | 25.5 | 25.3 | 27.4 | 26.3 | 28.9 | 36.9 |
| 0194 | EtOH | RT | 14 | 26.2 | 25.8 | 28.7 | 26.5 | 29.2 | 37.3 |
| 0194 | PEG | −80° C. | 14 | 26.9 | 26.2 | 28.5 | 28.3 | 31.3 | 36.7 |
| 0194 | PEG | RT | 14 | 26.6 | 26.3 | 28.6 | 27.4 | 30.1 | 36.1 |
| 1193 | EtOH | RT | 0 | 26.0 | 25.7 | 29.5 | 26.9 | 29.5 | 33.2 |
| 1193 | PEG | RT | 0 | 26.1 | 25.7 | 29.5 | 27.2 | 29.8 | 32.0 |
| 1193 | EtOH | −80° C. | 3 | 25.3 | 25.2 | 29.6 | 26.5 | 29.0 | 31.9 |
| 1193 | EtOH | RT | 3 | 25.6 | 25.6 | 30.2 | 26.7 | 29.2 | 32.4 |
| 1193 | PEG | −80° C. | 3 | 26.1 | 25.7 | 29.5 | 27.1 | 29.5 | 31.6 |
| 1193 | PEG | RT | 3 | 26.3 | 25.9 | 29.6 | 27.2 | 30.1 | 31.9 |
| 1193 | EtOH | −80° C. | 7 | 25.6 | 25.9 | 29.3 | 26.9 | 29.7 | 31.8 |
| 1193 | EtOH | RT | 7 | 25.6 | 25.6 | 30.4 | 26.6 | 29.3 | 32.3 |
| 1193 | PEG | −80° C. | 7 | 28.4 | 27.5 | 31.5 | 30.4 | 33.3 | 34.0 |
| 1193 | PEG | RT | 7 | 28.4 | 27.4 | 31.9 | 30.1 | 32.7 | 34.8 |
| 1193 | EtOH | −80° C. | 14 | 25.6 | 25.4 | 29.0 | 26.5 | 29.5 | 31.7 |
| 1193 | EtOH | RT | 14 | 25.8 | 25.7 | 30.4 | 26.9 | 29.5 | 33.3 |
| 1193 | PEG | −80° C. | 14 | 26.7 | 26.1 | 29.9 | 27.6 | 30.7 | 32.3 |
| 1193 | PEG | RT | 14 | 26.6 | 26.1 | 30.2 | 27.7 | 30.3 | 33.0 |

TABLE 22

PEG versus ethanol stability -- cycle threshold (Ct) and endpoint fluorescence.

| sample ID | TOP2A | MKi67 | ER1 v2 | ABL | HER2 | PRG v2 |
|---|---|---|---|---|---|---|
| | | | Cycle Threshold | | | |
| 0124 Day 0, EtOH-a | 35.0 | 37.9 | 30.9 | 31.9 | 33.5 | 36.7 |
| 0124 Day 0, EtOH-b | 35.8 | 36.1 | 30.8 | 31.8 | 34.2 | 37.8 |
| 0124 Day 0, EtOH-c | 35.9 | 38.4 | 31.2 | 32.3 | 34.9 | 40.2 |
| mean | 35.6 | 37.5 | 31.0 | 32.0 | 34.2 | 38.2 |
| 0124 Day 0, PEG-a | 35.2 | 34.8 | 30.6 | 31.5 | 34.0 | 37.1 |
| 0124 Day 0, PEG-b | 35.7 | 35.0 | 30.3 | 31.5 | 34.1 | 35.9 |

TABLE 22-continued

PEG versus ethanol stability -- cycle threshold (Ct) and endpoint fluorescence.

| sample ID | TOP2A | MKi67 | ER1 v2 | ABL | HER2 | PRG v2 |
|---|---|---|---|---|---|---|
| 0124 Day 0, PEG-c | 35.7 | 36.1 | 30.9 | 31.6 | 33.8 | 36.9 |
| mean | 35.5 | 35.3 | 30.6 | 31.5 | 34.0 | 36.6 |
| 0124 Day 3, EtOH -80-a | 34.9 | 35.1 | 30.6 | 31.1 | 33.4 | 36.9 |
| 0124 Day 3, EtOH -80-b | 35.3 | 34.9 | 30.5 | 31.2 | 33.4 | 37.1 |
| mean | 35.1 | 35.0 | 30.6 | 31.2 | 33.4 | 37.0 |
| 0124 Day 3, EtOH RT-a | 35.3 | 35.1 | 31.5 | 31.6 | 34.2 | 37.4 |
| 0124 Day 3, EtOH RT-b | 36.3 | 35.3 | 32.1 | 31.4 | 34.2 | 38.3 |
| mean | 35.8 | 35.2 | 31.8 | 31.5 | 34.2 | 37.9 |
| 0124 Day 3, PEG -80-a | 35.6 | 34.8 | 30.7 | 31.2 | 33.7 | 36.8 |
| 0124 Day 3, PEG -80-b | 35.7 | 35.0 | 30.8 | 31.7 | 34.4 | 36.3 |
| mean | 35.7 | 34.9 | 30.8 | 31.5 | 34.1 | 36.6 |
| 0124 Day 3, PEG RT-a | 35.3 | 35.3 | 30.9 | 32.2 | 34.2 | 37.4 |
| 0124 Day 3, PEG RT-b | 35.2 | 34.5 | 31.0 | 31.7 | 33.9 | 35.6 |
| mean | 35.3 | 34.9 | 31.0 | 32.0 | 34.1 | 36.5 |
| 0124 Day 7, EtOH -80-a | 34.9 | 34.1 | 30.3 | 30.8 | 32.9 | 36.8 |
| 0124 Day 7, EtOH -80-b | 35.4 | 34.5 | 30.2 | 30.5 | 33.3 | 36.8 |
| mean | 35.2 | 34.3 | 30.3 | 30.7 | 33.1 | 36.8 |
| 0124 Day 7, EtOH RT-a | 36.5 | 35.6 | 31.8 | 32.1 | 33.8 | 38.7 |
| 0124 Day 7, EtOH RT-b | 36.9 | 35.8 | 32.1 | 32.3 | 34.2 | 37.6 |
| mean | 36.7 | 35.7 | 32.0 | 32.2 | 34.0 | 38.2 |
| 0124 Day 7, PEG -80-a | 35.4 | 35.5 | 30.9 | 31.7 | 33.7 | 36.0 |
| 0124 Day 7, PEG -80-b | 36.6 | 37.1 | 33.1 | 34.7 | 38.5 | 38.9 |
| mean | 36.0 | 36.3 | 32.0 | 33.2 | 36.1 | 37.5 |
| 0124 Day 7, PEG RT-a | 36.6 | 36.5 | 32.6 | 35.1 | 36.4 | 41.0 |
| 0124 Day 7, PEG RT-b | 35.4 | 34.9 | 31.4 | 32.0 | 34.8 | 35.3 |
| mean | 36.0 | 35.7 | 32.0 | 33.6 | 35.6 | 38.2 |
| 0124 Day 14, EtOH -80-a | 35.1 | 34.0 | 30.5 | 31.1 | 33.4 | 38.2 |
| 0124 Day 14, EtOH -80-b | 34.3 | 34.5 | 30.3 | 30.8 | 33.3 | 36.6 |
| mean | 34.7 | 34.3 | 30.4 | 31.0 | 33.4 | 37.4 |
| 0124 Day 14, EtOH RT-a | 37.9 | 37.1 | 32.7 | 32.7 | 36.8 | 40.6 |
| 0124 Day 14, EtOH RT-b | 35.5 | 35.5 | 33.0 | 32.2 | 34.5 | 40.0 |
| mean | 36.7 | 36.3 | 32.9 | 32.5 | 35.7 | 40.3 |
| 0124 Day 14, PEG -80-a | 38.9 | 36.3 | 32.3 | 34.5 | 37.1 | 38.9 |
| 0124 Day 14, PEG -80-b | 35.4 | 34.8 | 30.8 | 31.4 | 34.5 | 37.3 |
| mean | 37.2 | 35.6 | 31.6 | 33.0 | 35.8 | 38.1 |
| 0124 Day 14, PEG RT-a | 36.1 | 35.3 | 31.7 | 32.2 | 34.3 | 38.1 |
| 0124 Day 14, PEG RT-b | 37.1 | 36.0 | 31.6 | 32.6 | 35.7 | 38.1 |
| mean | 36.6 | 35.7 | 31.7 | 32.4 | 35.0 | 38.1 |
| 0183 Day 0, EtOH-a | 32.5 | 32.3 | 29.2 | 30.7 | 33.9 | 30.8 |
| 0183 Day 0, EtOH-b | 32.3 | 31.9 | 28.9 | 30.0 | 32.5 | 29.9 |
| 0183 Day 0, EtOH-c | 32.2 | 32.3 | 29.1 | 30.2 | 32.8 | 30.6 |
| mean | 32.3 | 32.2 | 29.1 | 30.3 | 33.1 | 30.4 |
| 0183 Day 0, PEG-a | 33.0 | 32.7 | 29.8 | 31.3 | 35.4 | 31.1 |
| 0183 Day 0, PEG-b | 33.1 | 32.6 | 29.6 | 31.0 | 34.6 | 30.7 |
| 0183 Day 0, PEG-c | 33.3 | 33.3 | 30.2 | 31.4 | 34.5 | 31.2 |
| mean | 33.1 | 32.9 | 29.9 | 31.2 | 34.8 | 31.0 |
| 0183 Day 3, EtOH -80-a | 31.8 | 32.0 | 28.8 | 30.1 | 33.1 | 30.5 |
| 0183 Day 3, EtOH -80-b | 33.0 | 32.9 | 29.4 | 31.2 | 33.3 | 31.2 |
| mean | 32.4 | 32.5 | 29.1 | 30.7 | 33.2 | 30.9 |
| 0183 Day 3, EtOH RT-a | 32.9 | 32.8 | 30.3 | 30.8 | 33.4 | 31.1 |
| 0183 Day 3, EtOH RT-b | 32.4 | 33.2 | 29.8 | 30.5 | 32.7 | 30.8 |
| mean | 32.7 | 33.0 | 30.1 | 30.7 | 33.1 | 31.0 |
| 0183 Day 3, PEG -80-a | 32.7 | 32.4 | 29.1 | 31.1 | 34.0 | 30.3 |
| 0183 Day 3, PEG -80-b | 32.5 | 32.5 | 29.1 | 31.5 | 34.9 | 31.0 |
| mean | 32.6 | 32.5 | 29.1 | 31.3 | 34.5 | 30.7 |
| 0183 Day 3, PEG RT-a | 32.8 | 33.3 | 30.2 | 31.4 | 33.7 | 31.0 |
| 0183 Day 3, PEG RT-b | 32.5 | 32.6 | 29.3 | 31.1 | 33.9 | 30.1 |
| mean | 32.7 | 33.0 | 29.8 | 31.3 | 33.8 | 30.6 |
| 0183 Day 7, EtOH -80-b | 32.3 | 32.3 | 29.3 | 30.2 | 32.7 | 30.4 |
| 0183 Day 7, EtOH RT-a | 33.0 | 33.7 | 30.4 | 31.2 | 34.1 | 31.7 |
| 0183 Day 7, EtOH RT-b | 32.7 | 32.9 | 30.8 | 31.2 | 33.6 | 31.8 |
| mean | 32.9 | 33.3 | 30.6 | 31.2 | 33.9 | 31.8 |
| 0183 Day 7, PEG -80-a | 33.4 | 32.5 | 29.7 | 31.8 | 34.0 | 30.9 |
| 0183 Day 7, PEG -80-b | 35.1 | 34.2 | 32.0 | 35.9 | 37.2 | 33.1 |
| mean | 34.3 | 33.4 | 30.9 | 33.9 | 35.6 | 32.0 |
| 0183 Day 7, PEG RT-a | 32.7 | 32.5 | 29.6 | 31.1 | 34.3 | 30.9 |
| 0183 Day 7, PEG RT-b | 33.2 | 33.1 | 29.4 | 31.4 | 34.8 | 31.4 |
| mean | 33.0 | 32.8 | 29.5 | 31.3 | 34.6 | 31.2 |
| 0183 Day 14, EtOH -80-a | 32.0 | 32.0 | 28.8 | 30.2 | 33.1 | 30.6 |
| 0183 Day 14, EtOH -80-b | 31.6 | 32.2 | 28.7 | 30.1 | 32.6 | 30.5 |
| mean | 31.8 | 32.1 | 28.8 | 30.2 | 32.9 | 30.6 |
| 0183 Day 14, EtOH RT-a | 34.4 | 33.8 | 31.7 | 32.2 | 34.1 | 33.1 |
| 0183 Day 14, EtOH RT-b | 33.6 | 33.9 | 31.2 | 31.3 | 34.3 | 32.3 |
| mean | 34.0 | 33.9 | 31.5 | 31.8 | 34.2 | 32.7 |
| 0183 Day 14, PEG -80-a | 32.7 | 32.6 | 29.2 | 31.4 | 33.8 | 30.9 |
| 0183 Day 14, PEG -80-b | 32.4 | 32.4 | 29.2 | 31.2 | 34.4 | 30.9 |

TABLE 22-continued

PEG versus ethanol stability -- cycle threshold (Ct) and endpoint fluorescence.

| sample ID | TOP2A | MKi67 | ER1 v2 | ABL | HER2 | PRG v2 |
|---|---|---|---|---|---|---|
| mean | 32.6 | 32.5 | 29.2 | 31.3 | 34.1 | 30.9 |
| 0183 Day 14, PEG RT-a | 34.1 | 34.0 | 31.3 | 32.1 | 35.0 | 32.6 |
| 0183 Day 14, PEG RT-b | 33.4 | 32.6 | 30.2 | 31.6 | 33.7 | 31.1 |
| mean | 33.8 | 33.3 | 30.8 | 31.9 | 34.4 | 31.9 |
| 0194 Day 0, EtOH-a | 25.9 | 25.3 | 27.4 | 26.1 | 28.5 | 34.4 |
| 0194 Day 0, EtOH-b | 25.8 | 25.1 | 27.2 | 26.3 | 28.4 | 36.6 |
| 0194 Day 0, EtOH-c | 25.9 | 25.2 | 27.6 | 26.2 | 28.3 | 35.2 |
| mean | 25.9 | 25.2 | 27.4 | 26.2 | 28.4 | 35.4 |
| 0194 Day 0, PEG-a | 26.1 | 25.5 | 27.5 | 26.9 | 29.0 | 33.6 |
| 0194 Day 0, PEG-b | 26.0 | 25.3 | 27.5 | 26.6 | 28.8 | 34.3 |
| 0194 Day 0, PEG-c | 26.3 | 25.6 | 27.9 | 27.0 | 29.5 | 35.0 |
| mean | 26.1 | 25.5 | 27.6 | 26.8 | 29.1 | 34.3 |
| 0194 Day 3, EtOH -80-a | 25.3 | 24.9 | 27.1 | 25.8 | 28.3 | 33.8 |
| 0194 Day 3, EtOH -80-b | 25.2 | 24.9 | 26.7 | 25.9 | 28.1 | 34.4 |
| mean | 25.3 | 24.9 | 26.9 | 25.9 | 28.2 | 34.1 |
| 0194 Day 3, EtOH RT-a | 26.1 | 25.5 | 28.2 | 26.4 | 28.8 | 36.7 |
| 0194 Day 3, EtOH RT-b | 25.7 | 25.4 | 28.1 | 26.3 | 28.5 | 35.2 |
| mean | 25.9 | 25.5 | 28.2 | 26.4 | 28.7 | 36.0 |
| 0194 Day 3, PEG -80-a | 26.2 | 25.3 | 27.4 | 26.4 | 29.3 | 33.1 |
| 0194 Day 3, PEG -80-b | 26.1 | 25.4 | 27.4 | 26.6 | 29.3 | 35.5 |
| mean | 26.2 | 25.4 | 27.4 | 26.5 | 29.3 | 34.3 |
| 0194 Day 3, PEG RT-a | 26.2 | 25.6 | 27.9 | 26.8 | 29.5 | 35.0 |
| 0194 Day 3, PEG RT-b | 26.2 | 25.5 | 27.8 | 26.7 | 29.0 | 33.3 |
| mean | 26.2 | 25.6 | 27.9 | 26.8 | 29.3 | 34.2 |
| 0194 Day 7, EtOH -80-a | 25.5 | 25.2 | 27.3 | 25.8 | 28.3 | 34.1 |
| 0194 Day 7, EtOH -80-b | 25.2 | 24.9 | 27.3 | 25.9 | 28.4 | 34.4 |
| mean | 25.4 | 25.1 | 27.3 | 25.9 | 28.4 | 34.3 |
| 0194 Day 7, EtOH RT-a | 25.6 | 25.5 | 27.9 | 26.2 | 29.1 | 34.7 |
| 0194 Day 7, EtOH RT-b | 25.4 | 25.3 | 27.5 | 26.2 | 28.5 | 34.9 |
| mean | 25.5 | 25.4 | 27.7 | 26.2 | 28.8 | 34.8 |
| 0194 Day 7, PEG -80-a | 27.7 | 26.4 | 29.1 | 28.6 | 31.7 | 36.1 |
| 0194 Day 7, PEG -80-b | 28.8 | 27.3 | 30.0 | 30.2 | 33.0 | 36.0 |
| mean | 28.3 | 26.9 | 29.6 | 29.4 | 32.4 | 36.1 |
| 0194 Day 7, PEG RT-a | 26.3 | 25.5 | 27.7 | 26.7 | 29.5 | 34.1 |
| 0194 Day 7, PEG RT-b | 27.5 | 26.5 | 28.9 | 28.7 | 32.1 | 35.7 |
| mean | 26.9 | 26.0 | 28.3 | 27.7 | 30.8 | 34.9 |
| 0194 Day 14, EtOH -80-a | 25.2 | 25.2 | 27.1 | 26.1 | 28.8 | 36.0 |
| 0194 Day 14, EtOH -80-b | 25.7 | 25.4 | 27.6 | 26.5 | 28.9 | 37.7 |
| mean | 25.5 | 25.3 | 27.4 | 26.3 | 28.9 | 36.9 |
| 0194 Day 14, EtOH RT-a | 26.2 | 25.8 | 28.6 | 26.5 | 29.2 | 37.5 |
| 0194 Day 14, EtOH RT-b | 26.1 | 25.7 | 28.8 | 26.5 | 29.2 | 37.1 |
| mean | 26.2 | 25.8 | 28.7 | 26.5 | 29.2 | 37.3 |
| 0194 Day 14, PEG -80-a | 27.9 | 27.1 | 29.3 | 29.8 | 33.1 | 38.0 |
| 0194 Day 14, PEG -80-b | 25.8 | 25.3 | 27.6 | 26.7 | 29.4 | 35.3 |
| mean | 26.9 | 26.2 | 28.5 | 28.3 | 31.3 | 36.7 |
| 0194 Day 14, PEG RT-a | 26.5 | 26.1 | 28.2 | 27.3 | 30.0 | 35.9 |
| 0194 Day 14, PEG RT-b | 26.6 | 26.4 | 28.9 | 27.4 | 30.2 | 36.2 |
| mean | 26.6 | 26.3 | 28.6 | 27.4 | 30.1 | 36.1 |
| 1193 Day 0, EtOH-a | 26.1 | 25.8 | 29.6 | 27.0 | 29.6 | 33.3 |
| 1193 Day 0, EtOH-b | 25.8 | 25.7 | 29.3 | 26.6 | 29.5 | 32.8 |
| 1193 Day 0, EtOH-c | 26.0 | 25.7 | 29.6 | 27.0 | 29.5 | 33.6 |
| mean | 26.0 | 25.7 | 29.5 | 26.9 | 29.5 | 33.2 |
| 1193 Day 0, PEG-a | 26.1 | 25.7 | 29.5 | 27.1 | 29.8 | 31.5 |
| 1193 Day 0, PEG-b | 26.2 | 25.8 | 29.4 | 27.3 | 30.0 | 32.4 |
| 1193 Day 0, PEG-c | 25.9 | 25.6 | 29.5 | 27.1 | 29.7 | 32.2 |
| mean | 26.1 | 25.7 | 29.5 | 27.2 | 29.8 | 32.0 |
| 1193 Day 3, EtOH -80-a | 25.3 | 25.2 | 29.5 | 26.3 | 28.7 | 31.5 |
| 1193 Day 3, EtOH -80-b | 25.3 | 25.2 | 29.7 | 26.6 | 29.3 | 32.3 |
| mean | 25.3 | 25.2 | 29.6 | 26.5 | 29.0 | 31.9 |
| 1193 Day 3, EtOH RT-a | 25.7 | 25.6 | 30.3 | 26.6 | 29.1 | 32.3 |
| 1193 Day 3, EtOH RT-b | 25.5 | 25.5 | 30.1 | 26.8 | 29.2 | 32.4 |
| mean | 25.6 | 25.6 | 30.2 | 26.7 | 29.2 | 32.4 |
| 1193 Day 3, PEG -80-a | 26.2 | 25.9 | 29.5 | 27.1 | 29.6 | 31.6 |
| 1193 Day 3, PEG -80-b | 26.0 | 25.5 | 29.4 | 27.0 | 29.4 | 31.5 |
| mean | 26.1 | 25.7 | 29.5 | 27.1 | 29.5 | 31.6 |
| 1193 Day 3, PEG RT-a | 26.3 | 26.0 | 29.9 | 27.2 | 30.1 | 32.3 |
| 1193 Day 3, PEG RT-b | 26.2 | 25.7 | 29.2 | 27.2 | 30.1 | 31.5 |
| mean | 26.3 | 25.9 | 29.6 | 27.2 | 30.1 | 31.9 |
| 1193 Day 7, EtOH -80-a | 25.8 | 26.0 | 29.4 | 27.1 | 29.9 | 32.4 |
| 1193 Day 7, EtOH -80-b | 25.4 | 25.7 | 29.2 | 26.7 | 29.5 | 31.2 |
| mean | 25.6 | 25.9 | 29.3 | 26.9 | 29.7 | 31.8 |
| 1193 Day 7, EtOH RT-a | 25.4 | 25.5 | 30.3 | 26.5 | 29.2 | 32.2 |
| 1193 Day 7, EtOH RT-b | 25.7 | 25.7 | 30.4 | 26.7 | 29.4 | 32.3 |
| mean | 25.6 | 25.6 | 30.4 | 26.6 | 29.3 | 32.3 |
| 1193 Day 7, PEG -80-a | 28.2 | 27.5 | 31.5 | 30.4 | 33.4 | 33.8 |
| 1193 Day 7, PEG -80-b | 28.6 | 27.4 | 31.4 | 30.4 | 33.1 | 34.1 |

TABLE 22-continued

PEG versus ethanol stability -- cycle threshold (Ct) and endpoint fluorescence.

| sample ID | TOP2A | MKi67 | ER1 v2 | ABL | HER2 | PRG v2 |
|---|---|---|---|---|---|---|
| mean | 28.4 | 27.5 | 31.5 | 30.4 | 33.3 | 34.0 |
| 1193 Day 7, PEG RT-a | 28.5 | 27.5 | 31.5 | 30.1 | 32.9 | 35.1 |
| 1193 Day 7, PEG RT-b | 28.2 | 27.2 | 32.2 | 30.1 | 32.4 | 34.5 |
| mean | 28.4 | 27.4 | 31.9 | 30.1 | 32.7 | 34.8 |
| 1193 Day 14, EtOH -80-a | 25.6 | 25.5 | 28.9 | 26.5 | 29.5 | 31.8 |
| 1193 Day 14, EtOH -80-b | 25.5 | 25.3 | 29.1 | 26.5 | 29.4 | 31.5 |
| mean | 25.6 | 25.4 | 29.0 | 26.5 | 29.5 | 31.7 |
| 1193 Day 14, EtOH RT-a | 25.6 | 25.6 | 30.3 | 26.8 | 29.4 | 33.1 |
| 1193 Day 14, EtOH RT-b | 25.9 | 25.8 | 30.5 | 27.0 | 29.5 | 33.4 |
| mean | 25.8 | 25.7 | 30.4 | 26.9 | 29.5 | 33.3 |
| 1193 Day 14, PEG -80-a | 26.6 | 25.9 | 30.0 | 27.5 | 30.7 | 32.3 |
| 1193 Day 14, PEG -80-b | 26.7 | 26.2 | 29.7 | 27.7 | 30.6 | 32.3 |
| mean | 26.7 | 26.1 | 29.9 | 27.6 | 30.7 | 32.3 |
| 1193 Day 14, PEG RT-a | 26.8 | 26.3 | 30.4 | 27.7 | 30.2 | 33.4 |
| 1193 Day 14, PEG RT-b | 26.4 | 25.9 | 30.0 | 27.6 | 30.3 | 32.5 |
| mean | 26.6 | 26.1 | 30.2 | 27.7 | 30.3 | 33.0 |
| End Point Fluorescence | | | | | | |
| 0124 Day 0, EtOH-a | 259 | 55 | 478 | 171 | 282 | 108 |
| 0124 Day 0, EtOH-b | 207 | 89 | 514 | 182 | 206 | 91 |
| 0124 Day 0, EtOH-c | 181 | 39 | 448 | 145 | 203 | 58 |
| mean | 216 | 61 | 480 | 166 | 230 | 86 |
| 0124 Day 0, PEG-a | 225 | 113 | 515 | 175 | 218 | 99 |
| 0124 Day 0, PEG-b | 190 | 104 | 473 | 171 | 233 | 120 |
| 0124 Day 0, PEG-c | 216 | 77 | 503 | 186 | 271 | 102 |
| mean | 210 | 98 | 497 | 177 | 241 | 107 |
| 0124 Day 3, EtOH -80-a | 227 | 100 | 426 | 180 | 246 | 99 |
| 0124 Day 3, EtOH -80-b | 228 | 105 | 484 | 188 | 220 | 94 |
| mean | 228 | 103 | 455 | 184 | 233 | 97 |
| 0124 Day 3, EtOH RT-a | 231 | 143 | 435 | 173 | 211 | 91 |
| 0124 Day 3, EtOH RT-b | 179 | 120 | 383 | 170 | 201 | 90 |
| mean | 205 | 132 | 409 | 172 | 206 | 91 |
| 0124 Day 3, PEG -80-a | 211 | 116 | 429 | 188 | 249 | 96 |
| 0124 Day 3, PEG -80-b | 189 | 111 | 471 | 160 | 209 | 108 |
| mean | 200 | 114 | 450 | 174 | 229 | 102 |
| 0124 Day 3, PEG RT-a | 247 | 103 | 504 | 159 | 228 | 102 |
| 0124 Day 3, PEG RT-b | 234 | 159 | 478 | 177 | 255 | 115 |
| mean | 241 | 131 | 491 | 168 | 242 | 109 |
| 0124 Day 7, EtOH -80-a | 226 | 130 | 490 | 184 | 238 | 97 |
| 0124 Day 7, EtOH -80-b | 203 | 109 | 506 | 185 | 244 | 96 |
| mean | 215 | 120 | 498 | 185 | 241 | 97 |
| 0124 Day 7, EtOH RT-a | 188 | 125 | 402 | 153 | 213 | 72 |
| 0124 Day 7, EtOH RT-b | 181 | 137 | 408 | 160 | 196 | 101 |
| mean | 185 | 131 | 405 | 157 | 205 | 87 |
| 0124 Day 7, PEG -80-a | 187 | 88 | 392 | 148 | 218 | 96 |
| 0124 Day 7, PEG -80-b | 238 | 71 | 413 | 143 | 123 | 75 |
| mean | 213 | 80 | 403 | 146 | 171 | 86 |
| 0124 Day 7, PEG RT-a | 236 | 102 | 454 | 119 | 148 | 50 |
| 0124 Day 7, PEG RT-b | 230 | 155 | 443 | 160 | 196 | 116 |
| mean | 233 | 129 | 449 | 140 | 172 | 83 |
| 0124 Day 14, EtOH -80-a | 210 | 135 | 429 | 170 | 231 | 76 |
| 0124 Day 14, EtOH -80-b | 267 | 102 | 502 | 176 | 221 | 98 |
| mean | 239 | 119 | 466 | 173 | 226 | 87 |
| 0124 Day 14, EtOH RT-a | 138 | 67 | 376 | 133 | 128 | 57 |
| 0124 Day 14, EtOH RT-b | 230 | 95 | 296 | 132 | 168 | 63 |
| mean | 184 | 81 | 336 | 133 | 148 | 60 |
| 0124 Day 14, PEG -80-a | 112 | 81 | 446 | 131 | 155 | 71 |
| 0124 Day 14, PEG -80-b | 226 | 118 | 476 | 188 | 221 | 88 |
| mean | 169 | 100 | 461 | 160 | 188 | 80 |
| 0124 Day 14, PEG RT-a | 210 | 117 | 442 | 157 | 222 | 75 |
| 0124 Day 14, PEG RT-b | 169 | 99 | 458 | 143 | 174 | 76 |
| mean | 190 | 108 | 450 | 150 | 198 | 76 |
| 0183 Day 0, EtOH-a | 281 | 194 | 484 | 166 | 155 | 173 |
| 0183 Day 0, EtOH-b | 295 | 212 | 480 | 181 | 196 | 191 |
| 0183 Day 0, EtOH-c | 261 | 177 | 449 | 163 | 170 | 161 |
| mean | 279 | 194 | 471 | 170 | 174 | 175 |
| 0183 Day 0, PEG-a | 289 | 187 | 510 | 161 | 109 | 185 |
| 0183 Day 0, PEG-b | 289 | 198 | 498 | 184 | 130 | 192 |
| 0183 Day 0, PEG-c | 217 | 129 | 343 | 134 | 130 | 151 |
| mean | 265 | 171 | 450 | 160 | 123 | 176 |
| 0183 Day 3, EtOH -80-a | 421 | 237 | 649 | 186 | 189 | 193 |
| 0183 Day 3, EtOH -80-b | 372 | 214 | 620 | 164 | 192 | 176 |
| mean | 397 | 226 | 635 | 175 | 191 | 185 |
| 0183 Day 3, EtOH RT-a | 295 | 204 | 461 | 185 | 179 | 197 |
| 0183 Day 3, EtOH RT-b | 307 | 175 | 504 | 180 | 176 | 183 |
| mean | 301 | 190 | 483 | 183 | 178 | 190 |

TABLE 22-continued

PEG versus ethanol stability -- cycle threshold (Ct) and endpoint fluorescence.

| sample ID | TOP2A | MKi67 | ER1 v2 | ABL | HER2 | PRG v2 |
|---|---|---|---|---|---|---|
| 0183 Day 3, PEG -80-a | 388 | 230 | 729 | 186 | 188 | 219 |
| 0183 Day 3, PEG -80-b | 366 | 201 | 732 | 176 | 145 | 199 |
| mean | 377 | 216 | 731 | 181 | 167 | 209 |
| 0183 Day 3, PEG RT-a | 276 | 156 | 407 | 155 | 164 | 185 |
| 0183 Day 3, PEG RT-b | 332 | 207 | 561 | 176 | 200 | 229 |
| mean | 304 | 182 | 484 | 166 | 182 | 207 |
| 0183 Day 7, EtOH -80-b | 310 | 180 | 457 | 172 | 171 | 185 |
| 0183 Day 7, EtOH RT-a | 388 | 172 | 535 | 173 | 163 | 173 |
| 0183 Day 7, EtOH RT-b | 410 | 220 | 546 | 169 | 171 | 167 |
| mean | 399 | 196 | 541 | 171 | 167 | 170 |
| 0183 Day 7, PEG -80-a | 285 | 198 | 477 | 150 | 161 | 176 |
| 0183 Day 7, PEG -80-b | 225 | 143 | 372 | 81 | 105 | 156 |
| mean | 255 | 171 | 425 | 116 | 133 | 166 |
| 0183 Day 7, PEG RT-a | 377 | 222 | 618 | 177 | 162 | 185 |
| 0183 Day 7, PEG RT-b | 299 | 200 | 629 | 168 | 145 | 162 |
| mean | 338 | 211 | 624 | 173 | 154 | 174 |
| 0183 Day 14, EtOH -80-a | 391 | 216 | 611 | 168 | 201 | 156 |
| 0183 Day 14, EtOH -80-b | 432 | 193 | 636 | 171 | 197 | 155 |
| mean | 412 | 205 | 624 | 170 | 199 | 156 |
| 0183 Day 14, EtOH RT-a | 234 | 172 | 367 | 136 | 185 | 141 |
| 0183 Day 14, EtOH RT-b | 269 | 146 | 420 | 167 | 141 | 142 |
| mean | 252 | 159 | 394 | 152 | 163 | 142 |
| 0183 Day 14, PEG -80-a | 329 | 185 | 607 | 146 | 142 | 150 |
| 0183 Day 14, PEG -80-b | 355 | 202 | 609 | 148 | 127 | 147 |
| mean | 342 | 194 | 608 | 147 | 135 | 149 |
| 0183 Day 14, PEG RT-a | 228 | 146 | 313 | 120 | 128 | 117 |
| 0183 Day 14, PEG RT-b | 299 | 217 | 456 | 143 | 167 | 169 |
| mean | 264 | 182 | 385 | 132 | 148 | 143 |
| 0194 Day 0, EtOH-a | 322 | 364 | 449 | 214 | 327 | 137 |
| 0194 Day 0, EtOH-b | 322 | 420 | 460 | 204 | 336 | 104 |
| 0194 Day 0, EtOH-c | 270 | 346 | 383 | 181 | 329 | 116 |
| mean | 305 | 377 | 431 | 200 | 331 | 119 |
| 0194 Day 0, PEG-a | 335 | 328 | 507 | 205 | 332 | 155 |
| 0194 Day 0, PEG-b | 320 | 361 | 492 | 200 | 327 | 134 |
| 0194 Day 0, PEG-c | 313 | 338 | 443 | 204 | 344 | 134 |
| mean | 323 | 342 | 481 | 203 | 334 | 141 |
| 0194 Day 3, EtOH -80-a | 397 | 409 | 488 | 236 | 334 | 133 |
| 0194 Day 3, EtOH -80-b | 351 | 357 | 551 | 202 | 320 | 145 |
| mean | 374 | 383 | 520 | 219 | 327 | 139 |
| 0194 Day 3, EtOH RT-a | 326 | 399 | 405 | 199 | 347 | 104 |
| 0194 Day 3, EtOH RT-b | 348 | 392 | 406 | 205 | 338 | 125 |
| mean | 337 | 396 | 406 | 202 | 343 | 115 |
| 0194 Day 3, PEG -80-a | 274 | 322 | 472 | 196 | 265 | 123 |
| 0194 Day 3, PEG -80-b | 387 | 396 | 541 | 220 | 328 | 123 |
| mean | 331 | 359 | 507 | 208 | 297 | 123 |
| 0194 Day 3, PEG RT-a | 343 | 358 | 448 | 199 | 282 | 114 |
| 0194 Day 3, PEG RT-b | 310 | 349 | 456 | 184 | 326 | 143 |
| mean | 327 | 354 | 452 | 192 | 304 | 129 |
| 0194 Day 7, EtOH -80-a | 300 | 303 | 393 | 213 | 300 | 122 |
| 0194 Day 7, EtOH -80-b | 408 | 394 | 406 | 199 | 293 | 111 |
| mean | 354 | 349 | 400 | 206 | 297 | 117 |
| 0194 Day 7, EtOH RT-a | 372 | 393 | 466 | 233 | 304 | 129 |
| 0194 Day 7, EtOH RT-b | 379 | 390 | 540 | 210 | 318 | 131 |
| mean | 376 | 392 | 503 | 222 | 311 | 130 |
| 0194 Day 7, PEG -80-a | 303 | 318 | 438 | 204 | 270 | 103 |
| 0194 Day 7, PEG -80-b | 290 | 298 | 432 | 178 | 218 | 102 |
| mean | 297 | 308 | 435 | 191 | 244 | 103 |
| 0194 Day 7, PEG RT-a | 324 | 394 | 488 | 215 | 305 | 126 |
| 0194 Day 7, PEG RT-b | 333 | 345 | 496 | 203 | 250 | 112 |
| mean | 329 | 370 | 492 | 209 | 278 | 119 |
| 0194 Day 14, EtOH -80-a | 428 | 335 | 518 | 189 | 268 | 88 |
| 0194 Day 14, EtOH -80-b | 408 | 360 | 432 | 177 | 289 | 70 |
| mean | 418 | 348 | 475 | 183 | 279 | 79 |
| 0194 Day 14, EtOH RT-a | 275 | 303 | 323 | 164 | 258 | 73 |
| 0194 Day 14, EtOH RT-b | 294 | 310 | 343 | 180 | 250 | 76 |
| mean | 285 | 307 | 333 | 172 | 254 | 75 |
| 0194 Day 14, PEG -80-a | 459 | 320 | 512 | 172 | 203 | 72 |
| 0194 Day 14, PEG -80-b | 437 | 401 | 448 | 206 | 289 | 92 |
| mean | 448 | 361 | 480 | 189 | 246 | 82 |
| 0194 Day 14, PEG RT-a | 377 | 382 | 464 | 182 | 263 | 91 |
| 0194 Day 14, PEG RT-b | 340 | 349 | 393 | 200 | 272 | 94 |
| mean | 359 | 366 | 429 | 191 | 268 | 93 |
| 1193 Day 0, EtOH-a | 313 | 362 | 349 | 204 | 129 | 137 |
| 1193 Day 0, EtOH-b | 329 | 347 | 355 | 220 | 128 | 151 |
| 1193 Day 0, EtOH-c | 327 | 346 | 295 | 184 | 131 | 116 |

TABLE 22-continued

PEG versus ethanol stability -- cycle threshold (Ct) and endpoint fluorescence.

| sample ID | TOP2A | MKi67 | ER1 v2 | ABL | HER2 | PRG v2 |
|---|---|---|---|---|---|---|
| mean | 323 | 352 | 333 | 203 | 129 | 135 |
| 1193 Day 0, PEG-a | 323 | 334 | 391 | 208 | 136 | 169 |
| 1193 Day 0, PEG-b | 315 | 324 | 364 | 188 | 134 | 154 |
| 1193 Day 0, PEG-c | 375 | 359 | 351 | 196 | 144 | 167 |
| mean | 338 | 339 | 369 | 197 | 138 | 163 |
| 1193 Day 3, EtOH -80-a | 426 | 419 | 339 | 227 | 169 | 173 |
| 1193 Day 3, EtOH -80-b | 313 | 336 | 311 | 188 | 129 | 150 |
| mean | 370 | 378 | 325 | 208 | 149 | 162 |
| 1193 Day 3, EtOH RT-a | 348 | 363 | 247 | 204 | 150 | 149 |
| 1193 Day 3, EtOH RT-b | 370 | 379 | 263 | 171 | 129 | 137 |
| mean | 359 | 371 | 255 | 188 | 140 | 143 |
| 1193 Day 3, PEG -80-a | 315 | 326 | 363 | 185 | 125 | 148 |
| 1193 Day 3, PEG -80-b | 352 | 386 | 371 | 198 | 134 | 158 |
| mean | 334 | 356 | 367 | 192 | 130 | 153 |
| 1193 Day 3, PEG RT-a | 322 | 350 | 333 | 207 | 129 | 154 |
| 1193 Day 3, PEG RT-b | 317 | 365 | 369 | 199 | 124 | 154 |
| mean | 320 | 358 | 351 | 203 | 127 | 154 |
| 1193 Day 7, EtOH -80-a | 353 | 313 | 347 | 186 | 104 | 127 |
| 1193 Day 7, EtOH -80-b | 378 | 295 | 338 | 188 | 117 | 134 |
| mean | 366 | 304 | 343 | 187 | 111 | 131 |
| 1193 Day 7, EtOH RT-a | 415 | 406 | 295 | 228 | 144 | 150 |
| 1193 Day 7, EtOH RT-b | 315 | 348 | 283 | 195 | 126 | 145 |
| mean | 365 | 377 | 289 | 212 | 135 | 148 |
| 1193 Day 7, PEG -80-a | 327 | 250 | 301 | 155 | 80 | 107 |
| 1193 Day 7, PEG -80-b | 304 | 271 | 354 | 162 | 88 | 126 |
| mean | 316 | 261 | 328 | 159 | 84 | 117 |
| 1193 Day 7, PEG RT-a | 304 | 295 | 293 | 173 | 91 | 104 |
| 1193 Day 7, PEG RT-b | 315 | 323 | 266 | 163 | 113 | 116 |
| mean | 310 | 309 | 280 | 168 | 102 | 110 |
| 1193 Day 14, EtOH -80-a | 371 | 343 | 369 | 198 | 120 | 124 |
| 1193 Day 14, EtOH -80-b | 397 | 351 | 349 | 194 | 136 | 147 |
| mean | 384 | 347 | 359 | 196 | 128 | 136 |
| 1193 Day 14, EtOH RT-a | 380 | 363 | 240 | 183 | 126 | 116 |
| 1193 Day 14, EtOH RT-b | 335 | 359 | 245 | 178 | 136 | 112 |
| mean | 358 | 361 | 243 | 181 | 131 | 114 |
| 1193 Day 14, PEG -80-a | 307 | 308 | 307 | 185 | 106 | 117 |
| 1193 Day 14, PEG -80-b | 354 | 309 | 345 | 201 | 120 | 131 |
| mean | 331 | 309 | 326 | 193 | 113 | 124 |
| 1193 Day 14, PEG RT-a | 308 | 329 | 278 | 167 | 116 | 109 |
| 1193 Day 14, PEG RT-b | 356 | 372 | 298 | 179 | 111 | 114 |
| mean | 332 | 351 | 288 | 173 | 114 | 112 |

Materials and Methods

Sample Preparation

Each FFPE block was cut to generate 7 sequential 10 μm scrolls. Scrolls were transferred to individually labeled 1.5 mL tubes. 1.2 mL of CT-NG lysis reagent (see Table 14) was added to each 1.5 mL tube. The tubes were vortexed for at least 3 seconds. The tubes were incubated for 30 min at 80° C. After 30 minutes of lysing, the samples were vortexed for about 3-5 seconds. After lysing, the samples were pooled together by sample number in labeled 15 mL tubes and vortexed to mix. Two 4.2 mL aliquots per sample were transferred to labeled 15 mL tubes. One tube was for Ethanol, the other was for PEG 200. 4.2 mL of Ethanol or PEG 200 was added to designated tubes. The tubes were vortexed for at least 10 seconds to mix.

Three 0.5 mL aliquots were used as Day 0 test samples using the 130213 BC Stratifier, 0.5 mL ADF. Three 1.1 mL aliquots were transferred to labeled 1.5 mL tubes from each test condition. These aliquots were stored at −80° C. and were tested at Day 3, 7 and 14 time points. The remaining material in each tube was stored at room temperature and tested at Days 3, 7 and 14.

Cartridge Preparation

Revised GENEXPERT® C cartridges were used for the assay. A funnel was inserted into chamber 3 for each cartridge. A MLV-RT/Taq combo bead and a 6-plex TSR bead were added to chamber 11. A small retain ball and a large retain ball were also dropped into chamber 11 and pushed down slightly.

On each day of testing 700 L of BCR-ABL Rinse Buffer was added to chamber 2 in all cartridges and 2000 μL of BCR-ABL Elution Buffer was added to chamber 5 in all cartridges.

Device Setup

The GENEXPERT® device was operated according to the command sequence shown in Table 23.

TABLE 23

Command sequence.

1  Log Pressure Log Pressure at 500 ms interval.;
2  Pressure Values Min Pressure: −130; Max Pressure: 130; ;
3  Aspirate From Elution; 600 uL @ 50 uL/sec; Direct Path;
4  Wait 3.0 second(s);
5  Dispense To Waste2; 600 uL @ 50 uL/sec; Direct Path;
6  Start Repeat 2 time(s);
7  Aspirate From sample + binding; 250 uL @ 50 uL/sec; Direct Path;
8  Wait 5.0 second(s);
9  Dispense To Waste; 250 uL @ 5 uL/sec; Filter Path;
10 Wait 1.0 second(s);
11 End Repeat
12 Aspirate Air From Air1; 100 uL @ 50 uL/sec; Direct Path;
13 Dispense Air To Waste; 100 uL @ 50 uL/sec; Filter Path;

TABLE 23-continued

Command sequence.

| | |
|---|---|
| 14 | Wait 5.0 second(s); |
| 15 | Aspirate From Waste2; 500 uL @ 50 uL/sec; Direct Path; |
| 16 | Wait 1.0 second(s); |
| 17 | Dispense To Waste; 500 uL @ 100 uL/sec; Direct Path; |
| 18 | Wait 1.0 second(s); |
| 19 | Aspirate From Rinse; 500 uL @ 50 uL/sec; Direct Path; |
| 20 | Dispense To Waste; 450 uL @ 10 uL/sec; Filter Path; |
| 21 | Wait 1.0 second(s); |
| 22 | Dispense To Waste; 50 uL @ 20 uL/sec; Direct Path; |
| 23 | Aspirate From Elution; 600 uL @ 50 uL/sec; Direct Path; |
| 24 | Wait 3.0 second(s); |
| 25 | Dispense To Waste; 300 uL @ 50 uL/sec; Direct Path; |
| 26 | Dispense To Chamber 4; 300 uL @ 50 uL/sec; Direct Path; |
| 27 | Aspirate From Elution; 120 uL @ 20 uL/sec; Direct Path; |
| 28 | Wait 1.0 second(s); |
| 29 | Dispense To Waste2; 20 uL @ 5 uL/sec; Filter Path; |
| 30 | Wait 5.0 second(s); |
| 31 | Dispense To RT PCR Beads; 40 uL @ 5 uL/sec; Filter Path; |
| 32 | Wait 10.0 second(s); |
| 33 | Dispense To RT PCR Beads; 40 uL @ 10 uL/sec; Filter Path; |
| 34 | Wait 5.0 second(s); |
| 35 | Dispense To Waste2; 20 uL @ 10 uL/sec; Direct Path; |
| 36 | Wait 1.0 second(s); |
| 37 | Aspirate Air From Air2; 30 uL @ 10 uL/sec; Direct Path; |
| 38 | Dispense Air To Waste; 10 uL @ 5 uL/sec; Direct Path; |
| 39 | Wait 5.0 second(s); |
| 40 | Dispense Air To Chamber 4; 20 uL @ 10 uL/sec; Filter Path; |
| 41 | Wait 5.0 second(s); |
| 42 | Toggle To RT PCR Beads; 5x Asp: 65@10 Disp: 65@10; Direct Path; |
| 43 | Wait 10.0 second(s); |
| 44 | Aspirate From RT PCR Beads; 75 uL @ 10 uL/sec; Direct Path; |
| 45 | Wait 1.0 second(s); |
| 46 | Dispense To MM; 75 uL @ 10 uL/sec; Direct Path; |
| 47 | Wait 1.0 second(s); |
| 48 | Aspirate Air From Air2; 40 uL @ 40 uL/sec; Direct Path; |
| 49 | Aspirate Into Tube; 70 uL @ 20 uL/sec; Direct Path; |
| 50 | Wait 3.0 second(s); |
| 51 | Pressurize Tube 40 uL @ 40 uL/sec; Block Tube Ports After Pressurization; |
| 52 | Log Pressure Off |
| 53 | Protocol 1: Hold; 2: Hold; ; |
| 54 | Protocol 1: Probe Check; 2: 3-Temperature Cycle; ; |

Example 5

Measurements from Stained Slides

The purpose of this example was to determine if it was possible to detect our RNA targets from Hematoxylin and Eosin stained slides using the Breast Cancer Stratifier assay. Test samples were DLS 1176 (4 µm), Proteogenix 013330T2 (4 µm), and Proteogenix 014470T2 (4 µm). The stained tissue sections were scrapped off the glass slide and then treated with the lysis reagent as described above. The results are shown in Table 24.

TABLE 24

Results of stained slide assay..

| | cycle threshold | | | | | | area (mm$^2$) | | | Vendor's |
|---|---|---|---|---|---|---|---|---|---|---|
| Sample (N = 3) | TOP2A | MKi67 | ER1 v2 | ABL | HER2 | PRG v2 | whole | tumor | non-tumor | call |
| DLS 1176, stained, whole A | 28.3 | 28.0 | 30.8 | 28.3 | 27.9 | 36.7 | 286 | 208 | 77 | ER−, PR− |
| DLS 1176, stained, whole B | 28.2 | 27.9 | 30.8 | 28.2 | 28.1 | 37.0 | 303 | 210 | 94 | |
| DLS 1176, unstained, whole | 27.7 | 27.6 | 30.1 | 28.0 | 27.4 | 37.5 | 251 | N/a | N/a | |
| Pro 330T, MD- DCIS | 29.3 | 29.5 | 25.6 | 29.4 | 30.8 | 31.7 | 154 | N/a | 47 | ER+, PR+, HER2− |
| Pro 330T, MD- Tumor | 29.5 | 29.8 | 25.9 | 29.2 | 31.3 | 33.2 | | 100 | N/a | |
| Pro 330T, stained, whole | 28.1 | 28.4 | 24.6 | 28.3 | 30.3 | 31.1 | 152 | 65 | 45 | |
| Pro 330T, unstained, whole | 27.5 | 28.4 | 24.0 | 27.8 | 29.4 | 30.8 | 148 | N/a | N/a | |
| Pro 470T, stained, whole-A | 32.7 | 32.9 | 30.5 | 32.2 | 32.5 | 33.5 | 185 | 132 | 37 | not available |
| Pro 470T, stained, whole-B | 32.5 | 33.2 | 30.3 | 31.9 | 32.4 | 32.9 | 176 | 139 | 38 | |
| Pro 470T, unstained, whole | 33.0 | 33.3 | 30.9 | 32.1 | 32.3 | 33.6 | 177 | N/a | N/a | |

* Because cover slips were not applied to the stained slides in a timely manner, the tissue samples likely became dried out.

As shown in Table 24, stained samples gave comparable results to the parallel unstained samples. The H&E staining does not appear to affect the Stratifier's ability to detect the target RNA.

Being able to use a stained (and Pathologist scored) H&E slide may give us an advantage over having to use an unstained slide or scroll. A stained and scored slide may also be beneficial if it is desired to macro-dissect away unwanted portions to increase the percent-tumor content of a sample.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A lysis solution for extracting a nucleic acid from a fixed paraffin-embedded biological tissue sample, said lysis solution comprising:
   a buffer sufficient to maintain the pH of said solution at a pH ranging from about pH 3 to about pH 9;
   a chaotropic agent;
   an antioxidant and/or chelating agent; and
   a detergent;
   wherein said lysis solution does not comprise a protease, an organic solvent, or any additional reagents for deparaffinization.

2. The lysis solution of claim 1, wherein said buffer comprises a buffer selected from the group consisting of Tris, phosphate buffer, PBS, citrate buffer, TAPS, Bicine, Tricine, TAPSO, HEPES, TES, MOPS, PIPES, Cacodylate, SSC, and IVIES.

3. The lysis solution of claim 1, wherein said chaotropic agent comprises an agent selected from the group consisting of a guanidinium compound, formamide, lithium perchlorate, magnesium chloride, urea, and thiourea.

4. The lysis solution of claim 1, wherein said chaotropic agent comprises a guanidinium compound selected from the group consisting of guanidinium hydrochloride, and guanidinium isothiocyanate.

5. The lysis solution of claim 1, wherein the concentration of said chaotropic agent in said solution ranges from about 1 M to about 10 M.

6. The lysis solution of claim 1, wherein said antioxidant and/or chelating agent comprises an agent selected from the group consisting of N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N,N',N'-tetraacetic acid (BAPTA), and a phosphonate chelating agent.

7. The lysis solution of claim 1, wherein the concentration of said antioxidant and/or chelating agent in said solution ranges from about 10 mM to about 100 mM and/or said antioxidant and/or chelating agent comprises about 0.5% to about 5% of said solution.

8. The lysis solution of claim 1, wherein said detergent is an ionic detergent or a non-ionic detergent.

9. The lysis solution of claim 1, wherein said detergent comprises a detergent selected from the group consisting of N-lauroylsarcosine, BRIJ® 35, sodium dodecyl sulfate (SDS), cetyl methyl ammonium bromide (CTAB), TRITON®-X-100, n-octyl-β-D-glucopyranoside, CHAPS, n-octanoylsucrose, n-octyl-β-D-maltopyranoside, n-octyl-β-D-thioglucopyranoside, PLURONIC® F-127, TWEEN® 20, and n-heptyl-β-D-glucopyranoside.

10. The lysis solution of claim 1, wherein said detergent comprises about 0.1% to about 2% of said solution, and/or ranges from about 10 mM up to about 100 mM.

11. The lysis solution of claim 1, wherein said solution further comprises a second detergent.

12. The lysis solution of claim 1, wherein said solution comprises a second chaotrope and/or reducing agent.

13. The lysis solution of claim 1, wherein said solution further comprises calcium chloride.

14. The lysis solution of claim 1, wherein said solution comprises:
   Tris buffer;
   EDTA;
   guanidine hydrochloride;
   SDS;
   Tween 20;
   urea; and
   calcium chloride.

15. The lysis solution of claim 14, wherein
   said Tris buffer is at about pH 7 and is present at a concentration of about 50 mM;
   said EDTA is present at a concentration of about 50 mM;
   said guanidine hydrochloride is present at a concentration of about 4 M;
   said SDS is present at a concentration of about 34.7 mM;
   said urea is present at a concentration of about 6 M;
   said Tween is present at about 10% (v/v); and
   said calcium chloride is present at a concentration of about 10 mM.

16. The lysis solution of claim 1, wherein said solution comprises:
   guanidine thiocyanate;
   N-acetyl-L-cysteine;
   sodium citrate;
   N-Lauroylsarcosine; and
   the pH of said solution ranges from about pH 3.0 to about pH 5.5.

17. The lysis solution of claim 16, wherein said solution comprises:
   guanidine thiocyanate at about 4.5 M;
   about 1% N-acetyl-L-cysteine;
   about 25 mM sodium citrate; and
   about 0.40% N-Lauroylsarcosine.

18. The lysis solution of claim 16, wherein said solution comprises:
   guanidine thiocyanate at about 4.5 M;
   about 1% N-acetyl-L-cysteine;
   about 25 mM sodium citrate; and
   about 50 mM Trizma base.

19. The lysis solution of claim 1, wherein said solution comprises:
   Tris buffer;
   guanidinium hydrochloride;
   EDTA; and
   BRIJ® 35.

* * * * *